US008114875B2

(12) United States Patent
Geneste et al.

(10) Patent No.: US 8,114,875 B2
(45) Date of Patent: Feb. 14, 2012

(54) SUBSTITUTED N-HETEROCYCLIC COMPOUNDS AND THEIR USE AS DOPAMINE D₃ RECEPTOR LIGANDS

(75) Inventors: Herve Geneste, Neuhofen (DE); Daryl R. Sauer, Trevor, WI (US)

(73) Assignee: Abbott GmbH & Co. KG, Wiesbaden (DE)

( * ) Notice: Subject to any disclaimer, the term of this patent is extended or adjusted under 35 U.S.C. 154(b) by 301 days.

(21) Appl. No.: 11/793,633

(22) PCT Filed: Dec. 20, 2005

(86) PCT No.: PCT/EP2005/013737
§ 371 (c)(1),
(2), (4) Date: Mar. 7, 2008

(87) PCT Pub. No.: WO2006/066885
PCT Pub. Date: Jun. 29, 2006

(65) Prior Publication Data
US 2009/0054449 A1    Feb. 26, 2009

(30) Foreign Application Priority Data
Dec. 21, 2004 (DE) .................. 10 2004 061 593

(51) Int. Cl.
  A61K 31/513   (2006.01)
  C07D 239/36   (2006.01)
  C07D 237/54   (2006.01)
  A61K 31/496   (2006.01)
  C07D 213/64   (2006.01)
  C07D 213/69   (2006.01)
(52) U.S. Cl. .............. 514/252.14; 514/253.12; 544/295; 544/365
(58) Field of Classification Search .................. None
See application file for complete search history.

(56) References Cited

FOREIGN PATENT DOCUMENTS

| EP | 0 711 763 A | 5/1996 |
|---|---|---|
| GB | 2 369 616 A | 6/2002 |
| WO | WO 91/09594 A | 7/1991 |
| WO | WO 95/00131 A | 1/1995 |
| WO | WO 97/23216 A | 7/1997 |
| WO | WO 98/08842 A | 3/1998 |
| WO | WO 00/53596 A | 9/2000 |
| WO | WO 2004/080981 A | 9/2004 |

OTHER PUBLICATIONS

Cha, Mi Young et al., "QSAR Studies on Piperazinylalkylisoxazole Analogues Selectively Acting on Dopamine D3 Receptor by HQSAR and CoMFA", Bioorganic & Medicinal Chemistry, 11(7), 1293-1298, 2003, XP002373147.
Database WPI, Section Cb, Week 199202, Derwent Publications Ltd., London, GB; Class B03, AN 1992-013607 XP002373164, (1991).
Guzikowski, Anthony P. et al.; "Synthesis of N-Substituted 4-(4-Hydroxyphenyl)piperidines, 4-(4-Hydroxybenzyl)piperidines, and (±)-3-(4-Hydroxyphenyl)pyrrolidines: Selective Antagonists at the 1A/2B NMDA Receptor Subtype", Journal of Medicinal Chemistry, 43(5), 984-994 Coden: JMCMAR; Issn: 0022-2623, 2000, XP002373148.
Ismaiel A M et al.; "Ketanserin Analogues: The Effect of Structural Modification on S-HT2 Serotonin Receptor Binding" Journal of Medicinal Chemistry, American Chemical Society, Washington, U.S., Bd. 38, Nr. 7, 1995.
Baziard-Mouysset G. et al., "Syntheses and Structure-activity relationships of novel 2-amino alkyl chromones and related derivatives as sigma site-selective ligands", European Journal of Medicinal Chemistry, Editions Scientifique Elsevier, Paris, Fr., Bd 33, Nr. 5, Jun. 1998, XP004127366.
Jeffrey N. Joyce; "Dopamine D3 Receptor a a Therapeutic Target for Antipsychotic and Antiparkinsonian Drugs" Pharmacology & Therapeutics 90 (2001) 231-259.
Jean-Charles Schwartz et at.; "The Dopamine D3 Receptor as a Target for Antipsychotics" Novel Antipsychotic Drugs, 1992 pp. 135-144.
Pierre Sokoloff et at.; "Molecular Cloning and Characterization of a Novel Dopamine Reeceptor (d3) as a Target for Neuroleptics" Nature vol. 347 Sep. 13, 1990, pp. 146-151.
P. Sokoioff et al.; "Localization and Function of the D3 Dopamine Receptor" Arzneim.-Forsch./Drgu Res. 42 (1), Nr. 2a 1992, pp. 224-230.
Heidbreder, C.A., et al. The role of central dopamine D3 receptors in drug addiction: a review of pharmacological evidence. Brain Research Reviews, 2005;49:77-105.
Muhlbauer B., et al. . . Dopamine D3 receptors in the rat kidney: role in physiology and pathophysiology. Acta Physiologica Scandinavica, 2000;168(1):219-23.
Xi, Z. et al., "Selective dopamine D3 receptor antagonism by SB-277011A attenuates cocaine reinforcement as assessed by progressive-ratio and variable-cost-variable-payoff fixed-ratio cocaine self-administration in rats," European Journal of Neuroscience, 2005;21:3427-38.

(Continued)

*Primary Examiner* — Emily Bernhardt
(74) *Attorney, Agent, or Firm* — Lisa V. Mueller; Michael Best & Friedrich LLP

(57) ABSTRACT

The invention relates to substituted N-heterocyclic compounds of general formula (I.A)

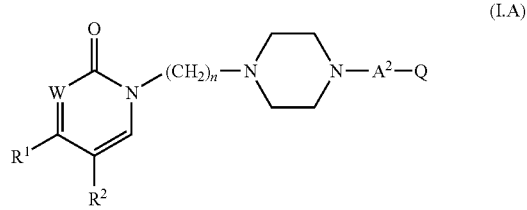

(I.A)

and to the tautomers of the compounds the physiologically acceptable salts of the compounds and the physiologically acceptable salts of the tautomers of the compounds. The invention also relates to the use of these compounds and their pharmacologically acceptable salts in the production of a pharmaceutical agent for treating diseases that respond to the influence exerted by dopamine D³ receptor ligands, especially for treating diseases of the central nervous system, especially schizophrenia and/or depression.

9 Claims, No Drawings

OTHER PUBLICATIONS

Vorel, S.R., et al., "Dopamine D3 receptor antagonism inhibits cocaine-seeking and cocaine-enhanced brain rewards in rats," The Journal of Neuroscience, 2002;22(21):9595-9603.

Xi, Z., et al., "Blockade of mesolimbic dopamine D3 receptors inhibits stress-induced reinstatement of cocaine-seeking in rats," Psychopharmacology, 2004;176:57-65.

Staley, J.K., "Adaptive increase in D3 dopamine receptors in the brain reward circuits of human cocaine fatalities," The Journal of Neuroscience, 1996;16(19):6100-6.

Gilbert, J., et al., "The dopamine D3 receptor antagonists SB277011A and NGB2904 inhibit cocaine-associated cue-induced reinstatement of drug-seeking behavior in rat," Program No. 691.7, 2004, Abstract Viewer/Itinerary Planner, Washington., D.C., Society for Neuroscience.

Heidbreder, C.A., et al., "Role of dopamine D3 receptors in the addictive properties of ethanol," Drugs of Today, 2004;40(4):355-65.

Thanos, P.K., "The selective dopamine D3 receptor antagonist SB-277011-A attenuates ethanol consumption in ethanol preferring (P) and non-preferring (NP) rats," Pharmacology, Biochemistry, and Behavior, 2005;81:190-7.

Andreoli, M., et al., "Selective antagonism at dopamine D3 receptors prevents nicotine-triggered relapse to nicotine-seeking behavior," Neuropsychopharmacology, 2003;28:1272-80.

Luippold, G., et al., "Effect of dopamine D3 receptor blockade on renal function and glomerular size in diabetic rats," Naunyn-Schmiedeberg's Arch. Pharmacol., 2005;371:420-7.

SUBSTITUTED N-HETEROCYCLIC COMPOUNDS AND THEIR USE AS DOPAMINE $D_3$ RECEPTOR LIGANDS

The present invention relates to novel substituted N-heterocyclic compounds. These compounds have valuable therapeutic properties and are suitable in particular for the treatment of disorders which respond to modulation of the dopamine $D_3$ receptor.

Neurons receive their information inter alia via G protein-coupled receptors. There are numerous substances which exert their effect via these receptors. One of these is dopamine. Confirmed findings about the presence of dopamine and its physiological function as neurotransmitter have been published. Disturbances in the dopaminergic transmitter system result in disorders of the central nervous system which include, for example, schizophrenia, depression or Parkinson's disease. These and other disorders are treated with medicaments which interact with the dopamine receptors.

Until 1990, two subtypes of dopamine receptors were clearly defined pharmacologically, namely the $D_1$ and $D_2$ receptors. More recently, a third subtype has been found, namely the $D_3$ receptor, which appears to mediate some effects of antipsychotics and antiparkinsonian drugs (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-259 "The Dopamine $D_3$-Receptor as a Therapeutic Target for Antipsychotic and Antiparkinsonian Drugs").

Dopamine receptors are now divided into two families. Firstly the $D_2$ group consisting of $D_2$, $D_3$ and $D_4$ receptors, and secondly the $D_1$ group consisting of $D_1$ and $D_5$ receptors. Whereas $D_1$ and $D_2$ receptors are widespread, the expression of $D_3$ receptors by contrast appears to be regioselective. Thus, these receptors are preferentially found in the limbic system, the projecting regions of the mesolimbic dopamine system, especially in the nucleus accumbens, but also in other regions such as amygdala. Because of this comparatively regioselective expression, $D_3$ receptors are regarded as a target with few side effects, and it is assumed that a selective $D_3$ ligand ought to have the properties of known antipsychotics but not their dopamine $D_2$ receptor-mediated neurological side effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

Pyrimidine compounds having dopamine $D_3$ receptor affinity are disclosed in WO 03/002543 and WO 96/02519. Some of these compounds exhibit high affinities for the $D_3$ receptor. They are therefore proposed for the treatment of disorders of the central nervous system. However, the selectivity in relation to other receptors is unsatisfactory.

PCT/EP04/002609 relates to pyrimidinones, and the earlier patent application DE 102004027359.6 relates to pyridinones, each of which binds with high selectivity to the dopamine $D_3$ receptor.

There is a need for further compounds which show very high affinity for the $D_3$ receptor and moreover bind with high selectivity to this receptor. The invention is therefore based on the object of providing compounds which act as selective dopamine $D_3$ receptor ligands.

This object is achieved by substituted N-heterocyclic compounds of the general formula (I)

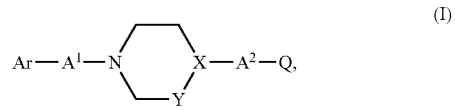

in which

Ar is phenyl, pyridinone, pyrimidinone or a 5- or 6-membered heteroaromatic radical which has 1 N atom as ring member and 0, 1, 2 or 3 further heteroatoms selected independently of one another from O, S and N as ring members;
  where Ar is optionally substituted by 1, 2 or 3 groups $R^a$ which are selected independently of one another from CN, $NO_2$, halogen, $OR^3$, $NR^4R^5$, $C(O)NR^4R^5$, O—C(O)$NR^4R^5$, $SR^6$, $SOR^6$, $SO_2R^6$, $SO_2NR^4R^5$, $COOR^7$, O—C(O)$R^8$, $COR^8$, $C_1$-$C_6$-alkyl, $C_2$-$C_6$-alkenyl, $C_2$-$C_6$-alkynyl, $C_3$-$C_6$-cycloalkyl; where $C_1$-$C_6$-alkyl and $C_2$-$C_6$-alkenyl are optionally substituted by 1, 2 or 3 radicals which are selected independently of one another from halogen, $OR^3$, $NR^4R^5$, $C(O)NR^4R^5$, O—C(O)$NR^4R^5$, $SR^6$, $SOR^6$, $SO_2R^6$, $SO_2NR^4R^5$, $COOR^7$, O—C(O)$R^8$, $COR^8$, $C_3$-$C_6$-cycloalkyl, phenyl and 4- to 6-membered heterocyclyl having 1, 2 or 3 heteroatoms selected from O, S and N; where phenyl and heterocyclyl in turn may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl and halogen; and
  where Ar may carry as substituent $R^{a1}$ also a phenyl radical or a 4- to 6-membered heterocyclyl radical which has 1, 2, 3 or 4 heteroatoms selected independently of one another from O, S and N as ring members; where the phenyl radical and the heterocyclyl radical is optionally substituted by 1, 2, 3 or 4 groups $R^a$ selected independently of one another;
$A^1$ is a 3- to 6-membered hydrocarbon chain which may have a double bond or a triple bond and/or a $C_1$-$C_4$-alkyl group and/or a group Z which is selected from O, S, C(O), $NR^3$, C(O)$NR^3$, $NR^3$C(O), OC(O) and C(O)O;
X is CH or N;
Y is $CH_2$ or $CH_2CH_2$; or
X—Y together are C=CH, C=CH—$CH_2$ or CH—CH=CH; and
$A^2$ is a 1- to 2-membered hydrocarbon chain which may have 1 or 2 methyl groups as substituents, in which 1 carbon atom may be replaced by a carbonyl group;
Q is 5- or 6-membered carbocyclyl or heterocyclyl having 1, 2 or 3 heteroatoms selected from O, N and S;
  where carbocyclyl and heterocyclyl may each be completely saturated, partly unsaturated or aromatic, and may have 1, 2 or 3 substituents which are selected independently of one another from
  $C_1$-$C_6$-alkyl which is optionally substituted one or more times by OH, $C_1$-$C_4$-alkoxy, halogen or phenyl which may in turn carry 1, 2 or 3 substituents selected from $C_1$-$C_4$-alkyl, $C_1$-$C_4$-alkoxy, $NR^4R^5$, OH, CN, $C_1$-$C_2$-fluoroalkyl and halogen;
  $C_2$-$C_6$-alkenyl, $C_2$-$C_6$-alkynyl, $C_3$-$C_6$-cycloalkyl, $C_4$-$C_{10}$-bicycloalkyl, $C_6$-$C_{10}$-tricycloalkyl, where the last five groups mentioned may optionally be substituted by halogen or $C_1$-$C_4$-alkyl;
  halogen, CN, $OR^3$, $NR^4R^5$, $NO_2$, $SR^6$, $SO_2R^6$, $SO_2NR^4R^5$, $COOR^7$, $COR^8$;

phenyl, 5- or 6-membered heterocyclyl having 1, 2 or 3 heteroatoms selected from O, S and N, where phenyl and heterocyclyl optionally carry 1 or 2 substituents which are selected independently of one another from $C_1$-$C_4$-alkyl, $C_1$-$C_4$-alkoxy, $NR^4R^5$, OH, CN, $C_1$-$C_2$-fluoroalkyl and halogen; and where 2 substituents bonded to adjacent C atoms of the 5- or 6-membered carbocyclyl or heterocyclyl may together be $C_3$- or $C_4$-alkylene, or together with the C atoms to which they are bonded may be a fused, unsaturated 4-, 5- or 6-membered carbocycle or a 4-, 5- or 6-membered heterocycle having 1 or 2 heteroatoms selected from O, N and S as ring members;

$R^3$, $R^4$, $R^5$, $R^6$, $R^7$, $R^8$ are independently of one another H, $C_1$-$C_6$-alkyl which is optionally substituted by OH, $C_1$-$C_4$-alkoxy or phenyl which in turn may have 1, 2 or 3 substituents selected from $C_1$-$C_4$-alkyl, $C_1$-$C_4$-alkoxy, $NR^4R^5$, OH, CN, $C_1$-$C_2$-fluoroalkyl or halogen, or $COR^{11}$, $C_1$-$C_6$-haloalkyl or phenyl which in turn may have 1, 2 or 3 substituents selected from $C_1$-$C_4$-alkyl, $C_1$-$C_4$-alkoxy, $NR^4R^5$, OH, CN, $C_1$-$C_2$-fluoroalkyl or halogen; where $R^5$ may also be a group $COR^9$; and where $R^4$ with $R^5$ also together with the nitrogen atom to which they are bonded may form a 4-, 5- or 6-membered, saturated or unsaturated heterocycle which may have a further heteroatom selected from O, S and $NR^{10}$ as ring member, where the heterocycle is unsubstituted or carries one or two $C_1$-$C_4$-alkyl groups;

$R^9$ is hydrogen, $C_1$-$C_4$-alkyl or phenyl which is optionally substituted by 1, 2 or 3 radicals which are selected independently of one another from $C_1$-$C_4$-alkyl, $C_1$-$C_4$-alkoxy, $NR^4R^5$, CN, $C_1$-$C_2$-fluoroalkyl or halogen;

$R^{10}$ is hydrogen or $C_1$-$C_4$-alkyl, and $R^{11}$ is H, $C_1$-$C_6$-alkyl which is optionally substituted by OH, $C_1$-$C_4$-alkoxy or phenyl which in turn may have 1, 2 or 3 substituents selected from $C_1$-$C_4$-alkyl, $C_1$-$C_4$-alkoxy, $NR^4R^5$, OH, CN, $C_1$-$C_2$-fluoroalkyl or halogen, or $C_1$-$C_6$-haloalkyl or phenyl which in turn may have 1, 2 or 3 substituents selected from $C_1$-$C_4$-alkyl, $C_1$-$C_4$-alkoxy, $NR^4R^5$, OH, CN, $C_1$-$C_2$-fluoroalkyl or halogen;

and the tautomers of the compounds I, the physiologically acceptable salts of the compounds I and the physiologically acceptable salts of the tautomers of the compounds I.

The present invention therefore relates to the compounds of the general formula I, their tautomers and the physiologically tolerated salts of the compounds I and the physiologically acceptable salts of the tautomers of I.

The present invention additionally relates to a pharmaceutical composition comprising at least one pyri(mi)dinone compound of the formula I, the tautomers thereof, the physiologically acceptable acid addition salts thereof and/or the physiologically acceptable acid addition salts of the tautomers and, where appropriate, one or more physiologically acceptable carriers.

The present invention also relates to the use of a substituted N-heterocyclic compound of the formula I and of the tautomers thereof, and of the salts thereof or the salts of its tautomers for producing a pharmaceutical composition for the treatment of disorders which respond to modulation by dopamine $D_3$ receptor ligands.

The disorders which respond to modulation by dopamine $D_3$ receptor ligands include for example impairments and disorders of the central nervous system, especially schizophrenia and depression, Parkinsonism and epilepsy, also addictive disorders and renal functional impairments.

The aforementioned indications are treated by using according to the invention at least one compound of the general formula I with the meanings mentioned at the outset. If the compounds of the formula I have one or more centers of asymmetry, it is also possible to employ mixtures of enantiomers, especially racemates, mixtures of diastereomers, mixtures of tautomers, but preferably the respective substantially pure enantiomers, diastereomers and tautomers.

It is likewise possible to use physiologically acceptable salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid and benzoic acid. Further acids which can be used are described in Fortschritte der Arzneimittelforschung, volume 10, pages 224 et seq., Birkhäuser Verlag, Basle and Stuttgart, 1966.

Halogen here and hereinafter is fluorine, chlorine, bromine or iodine, especially fluorine or chlorine.

$C_n$-$C_m$-Alkyl (also in radicals such as alkoxy, alkylthio, alkylamino, etc.) means a straight-chain or branched alkyl group having n to m carbon atoms, e.g. 1 to 6 carbon atoms and in particular 1 to 4 carbon atoms. Examples of an alkyl group are methyl, ethyl, n-propyl, isopropyl, n-butyl, 2-butyl, isobutyl, tert-butyl, n-pentyl, 2-pentyl, neopentyl, n-hexyl and the like.

The alkyl group may have one or more substituents which are selected independently of one another from halogen, $OR^3$, $NR^4R^5$, $C(O)NR^4R^5$, O—$C(O)NR^4R^5$, $SR^6$, $SOR^6$, $SO_2R^6$, $SO_2NR^4R^5$, $COOR^7$, O—$C(O)R^8$, $COR^8$, $C_3$-$C_6$-cycloalkyl, 4-, 5- or 6-membered heterocyclyl having 1, 2 or 3 heteroatoms selected from O, S and N, and phenyl, where phenyl and heterocyclyl may be substituted by one or two radicals which are selected independently of one another from $C_1$-$C_4$-alkyl, $C_1$-$C_4$-alkoxy, $NR^4R^5$, CN, OH, $C_1$-$C_2$-fluoroalkyl or halogen.

In the case of a halogen substituent, the alkyl group may include in particular 1, 2, 3 or 4 halogen atoms, specifically fluorine or chlorine, which may be located on one or more C atoms, preferably in the α or ω position. Groups of this type are also referred to hereinafter as haloalkyl. Preferred haloalkyl is $C_1$-$C_2$-fluoroalkyl or $C_1$-$C_2$-fluorochloroalkyl, in particular $CF_3$, $CHF_2$, $CF_2Cl$, $CH_2F$, $CH_2CF_3$.

In the case of hydroxy-substituted alkyl, the alkyl group has in particular one hydroxy group, such as, for example, hydroxymethyl, 2-hydroxyeth-1-yl, 2-hydroxyprop-1-yl, 3-hydroxyprop-1-yl, 1-hydroxyprop-2-yl, 2-hydroxyprop-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl.

In the case of alkoxy-substituted alkyl, the alkyl group has in particular one alkoxy substituent. These radicals are referred to, depending on the number of carbon atoms, also as $C_n$-$C_m$-alkoxy-$C_n$-$C_m$-alkyl and are, for example, methoxymethyl, ethoxymethyl, 2-methoxyethyl, 1-methoxyethyl, 2-ethoxyethyl, 1-ethoxyethyl, n-propoxymethyl, isopropoxymethyl, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably methoxymethyl, ethoxymethyl, 2-methoxyethyl, 2-ethoxyethyl, 2-(methoxy)propyl, 2-(ethoxy)propyl or 3-(methoxy)propyl, 3-(ethoxy)propyl.

Cycloalkyl is in particular $C_3$-$C_6$-cycloalkyl such as cyclopropyl, cyclobutyl, cyclopentyl and cyclohexyl.

The term "alkylene" comprises in principle straight-chain or branched radicals having preferably 3 to 10 and particularly preferably 3 to 8 carbon atoms, such as prop-1,2-ylene, prop-1,3-ylene, but-1,2-ylene, but-1,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, hex-1,3-ylene, hex-2,4-ylene, hex-1,4-ylene, hex-1,5-ylene, hex-1,6-ylene and the like. $C_0$-Alkylene is a single bond, $C_1$-alkylene is methylene and $C_2$-alkylene is 1,1-ethylene or 1,2-ethylene.

The term "1- to 2-membered hydrocarbon chain" comprises a chain having 1 or 2 carbon atoms each having a free valency on the terminal atoms of the hydrocarbon chain. If a carbon atom in the 1- to 2-membered hydrocarbon chain is replaced by a carbonyl group, examples thereof are —C(O)—, —CH$_2$C(O)— or —C(O)CH$_2$—. The hydrocarbon chain may additionally carry one or two methyl groups. Examples thereof are —C(CH$_3$)H—, —CH(CH$_3$)CH$_2$—, —CH$_2$C(CH$_3$)H—, —CH(CH$_3$)CH(CH$_3$)$_2$—, —CH(CH$_3$)C(O)—, —C(O)CH(CH$_3$)— and the like.

The term "3- to 6-membered hydrocarbon chain" comprises a chain having 3, 4, 5 or 6 carbon atoms, with the two terminal atoms of the hydrocarbon chain each having a free valency. If the 3- to 6-membered hydrocarbon chain does not comprise a group Z or comprises a non-terminal group Z, the two terminal carbon atoms of the hydrocarbon chain each have a free valency. If the 3- to 6-membered hydrocarbon chain comprises a terminal group Z, one free valency is located on group Z and the second free valency is located on the terminal carbon atom of the chain. In addition, the 3- to 6-membered hydrocarbon chain may have a double bond or triple bond at any position, and/or carry a $C_1$-$C_4$-alkyl group. Examples thereof are —CH$_2$CH(CH$_3$)CH$_2$—, —CH$_2$CH(CH$_3$)CH$_2$CH$_2$—, —CH$_2$CH$_2$CH$_2$—CH(CH$_3$)—, —CH$_2$C(H)=C(H)CH$_2$—, —CH$_2$C(CH$_3$)=C(H)CH$_2$— and the like.

4-, 5- or 6-membered heterocyclyl comprises both aromatic heterocyclyl (hetaryl or heteroaryl) and completely saturated or partly unsaturated heterocyclic radicals. Heterocyclyl has 1, 2 or 3 heteroatoms selected from O, S and N, e.g. 1, 2 or 3 nitrogen atoms, 1 or 2 oxygen atoms, or 1 oxygen atom and 1 or 2 nitrogen atoms or 1 sulfur atom and 1 or 2 nitrogen atoms.

Heterocyclyl may be unsubstituted or have 1 or 2 substituents selected from $C_1$-$C_4$-alkyl, $C_1$-$C_4$-alkoxy, OH, CN, NR$^4$R$^5$, $C_1$-$C_2$-fluoroalkyl and halogen. Heterocyclyl may also have a fused 5- or 6-membered carbocycle, e.g. a benzene, cyclopentane or cyclohexene ring or a fused heterocycle, e.g. a fused pyrrolyl, furan, thiophene, thiazole, pyridine, pyrimidine or pyridazine ring.

Examples of saturated heterocyclyl are azetidin-1-yl, azetidin-2-yl, azetidin-3-yl, oxetan-2-yl, oxetan-3-yl, thietan-2-yl, thietan-3-yl, pyrrolidinyl, piperidyl, piperazinyl, morpholinyl, oxolanyl, 1,3-dioxolanyl, 1,3- and 1,4-dioxanyl, 1,3-oxothiolanyl, oxazolidinyl and the like.

Examples of 5- or 6-membered aromatic heterocyclic radicals (5- or 6-membered aromatic heterocyclyl) having 1, 2 or 3 heteroatoms which are selected from O, S and N are in particular pyridinyl, pyrimidinyl, pyrazinyl, triazinyl, imidazolyl, pyrrotyl, pyrazolyl, thienyl, furyl, oxazolyl, thiazolyl, isoxazolyl, tetrazolyl, thiadiazolyl and triazolyl. These may have 1 or 2 of the aforementioned substituents on the nitrogen atoms and on the carbon atoms. If one of the substituents is hydroxy, the radicals may also be in a tautomeric form with carbonyl groups. Examples of 5- or 6-membered heterocyclic radicals having a fused carbocycle comprise benzofuranyl, benzothienyl, indolyl, benzothiazolyl, benzoxazolyl, benzimidazolyl, benzopyrazolyl, 1,3-benzodioxolyl, quinolinyl, isoquinolinyl, quinoxalinyl, quinazolinyl, cinnolinyl, and the corresponding partly hydrogenated groups.

Examples of a fused 5 or 6-membered carbocycle are cyclopentene, cyclopentadiene, cyclohexene, cyclohexadiene and benzene. Examples of a fused 5- or 6-membered heterocycle having 1 or 2 nitrogen atoms as ring members are pyridine, 1,2,3,4- and 1,2,5,6-tetrahydropyridine, 1,2- and 1,4-dihydropyridine, pyrimidine, pyrazine and pyridazine.

In the group $A^1$, the carbon atoms of the chain, optionally together with the group Z, form a chain having at least three, and preferably at least four, members, which separates the ring of the group Ar from the nitrogen atom of the central (partly) saturated N-heterocycle of the formula (I) by at least 4 and preferably by at least 5 bonds. If $A^1$ does not have a group Z, then $A^1$ comprises 3 to 6 and preferably 4 or 5 and specifically 4 carbon atoms. If $A^1$ has at least one of said groups Z, then $A^1$ comprises 3 to 6, in particular 3 or 4 carbon atoms and the group Z. Preferred groups Z are O, S and NR$^3$. The heteroatoms of group Z are usually not connected to the nitrogen atom of the N-heterocycle carrying the group $A^2$-Q. The heteroatoms of the group Z are, if Ar is linked via a heteroatom to $A^1$, preferably bonded neither to the atom of the ring of group Ar nor to the nitrogen atom of the central (partly) saturated heterocycle. The hydrocarbon chain may carry a $C_1$-$C_4$-alkyl group. The saturated linkages in the carbon chain (alkylene) may be replaced by unsaturated linkages (alkenylene; alkynylene). Possible results are thus straight-chain or branched unsaturated groups $A^1$ whose number and arrangement of the carbon atoms corresponds to that of the aforementioned alkylene radicals, but where a single bond is replaced by an unsaturated double or triple bond.

Where the group $A^2$ is ethylene, the bonding sites are not located on the same atom, but form a two-membered chain which separates the ring of the group Q from the atom X of the central (partly) saturated N-heterocycle of the formula (I) by 3 bonds.

With a view to the use of the compounds of the invention as dopamine D$_3$ receptor ligands, Ar is preferably a radical of the formulae (a) to (m)

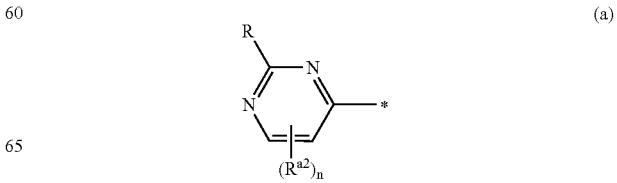

(a)

-continued

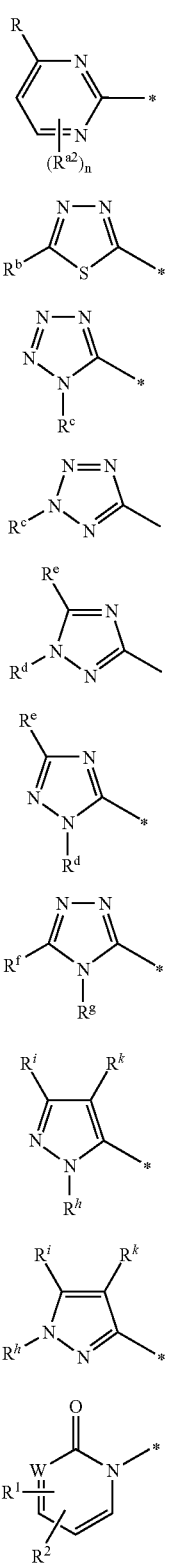

in which
* marks the position at which Ar is connected to A¹;
n in the formulae a and b is 0 or 1;
R is H, OH or halogen;
$R^{a2}$ has the meanings previously mentioned for $R^a$ or $R^{a1}$;

$R^b$, $R^e$, $R^f$, $R^i$, $R^k$ are each independently of one another H or a substituent $R^a$ or $R^{a1}$ as defined above;
$R^c$, $R^d$, $R^g$, $R^h$ are each independently of one another H, $C_1$-$C_4$-alkyl, $C_3$-$C_6$-cycloalkyl, $C_1$-$C_4$-alkoxymethyl or $C_1$-$C_2$-fluoroalkyl;
W is CH or N;
$R^1$ is hydrogen or a group $R^a$ or $R^{a1}$ as defined above; and
$R^2$ is hydrogen or a group $R^a$ as defined above.

It is self-evident to the skilled worker that in the case of the substituted N-heterocyclic compounds of the formula I where Ar is a radical of the formula (m), in the case where W=CH one of the substituents $R^1$ or $R^2$ may also be linked to the C atom located at the position of W.

The variables Ar, W, $A^1$, X, Y, $A^2$, $R^1$, $R^2$ and Q have independently of one another preferably the meanings indicated below:

Ar is a pyridinone or pyrimidinone residue of the formula (m), particularly preferably pyrimidinone (i.e. W=N), where the pyri(mi)dinone ring is optionally substituted by 1, 2 or 3 groups $R^a$ as defined above, and/or one group $R^{a1}$ as defined above, where the number of groups $R^a$ and $R^{a1}$ does not exceed 3.

$A^1$ is a 3- to 6-membered, in particular 4- to 6-membered, hydrocarbon chain which includes no group Z, where the hydrocarbon chain may have a double bond and/or a methyl group. In particularly preferred compounds of the formula I, $A^1$ is —$(CH_2)_{a1}$— in which a1 is 4, 5 or 6 and in particular 4, or $A^1$ is trans-$CH_2$—CH=CH—$CH_2$—, trans-$CH_2$—C($CH_3$)=CH—$CH_2$—, —$CH_2$—CH($CH_3$)—$CH_2$—$CH_2$— or —$CH_2$—$CH_2$—$CH_2$—CH($CH_3$)—. $A^1$ is particularly preferably —$(CH_2)_4$—;

X is CH or N, in particular N; and
Y is $CH_2$; or
X—Y together are C=CH; in particular, X is N and Y is $CH_2$;
$A^2$ is $CH_2$, $CH_2CH_2$, CO, $CH_2CO$ or $COCH_2$, in particular $CH_2$.

$R^1$ is a group halogen, $OR^3$, $NR^4R^5$, $SR^6$, $C_3$-$C_6$-cycloalkyl, $C_1$-$C_6$-alkyl which is optionally substituted by 1, 2, 3 or 4 radicals OH, $C_1$-$C_4$-alkoxy, halogen or phenyl, which are selected independently of one another, is phenyl or 5- or 6-membered aromatic heterocyclyl having 1, 2 or 3 heteroatoms selected from O, S and N, where heterocyclyl and phenyl may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen.

$R^1$ is in particular $C_1$-$C_6$-alkyl, specifically $C_1$-$C_4$-alkyl, halogen, optionally substituted phenyl or 2-furyl, $C_1$-$C_2$-fluoroalkyl, in particular trifluoromethyl, $C_4$-$C_6$-cycloalkyl, a group $OR^3$, a group $SR^6$ or a radical $NR^4R^5$. In this connection, $R^3$ is in particular hydrogen, $C_1$-$C_4$-alkyl, phenyl or benzyl and specifically hydrogen.

$R^4$ is preferably hydrogen or alkyl. $R^5$ is preferably hydrogen, $C_1$-$C_4$-alkyl, phenyl or benzyl or forms together with the nitrogen atom and the radical $R^4$ a 4-, 5- or 6-membered saturated heterocycle such as azetidinyl, pyrrolidinyl, piperidinyl, morpholinyl or piperazinyl. $R^6$ in this connection is preferably hydrogen, $C_1$-$C_4$-alkyl, phenyl or benzyl and in particular hydrogen. Substituted phenyl means here that the phenyl radical may be substituted by one or two radicals, e.g. by $C_1$-$C_4$-alkyl, $C_1$-$C_4$-alkoxy, $NR^4R^5$, OH, CN, $C_1$-$C_2$-fluoroalkyl and/or halogen.

In a particularly preferred embodiment of the invention, $R^1$ is $C_1$-$C_6$-alkyl, in particular $C_1$-$C_4$-alkyl and specifically methyl, isopropyl or tert-butyl, $C_1$-$C_2$-fluoroalkyl, in particular $CF_3$, $C_4$-$C_6$-cycloalkyl, in particular cyclobutyl or cyclohexyl, 2-furyl, phenyl which may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen, in particular p-fluorophenyl, m-fluorophenyl, o-fluorophenyl, p-methylphenyl, m-methylphenyl, o-methylphenyl, or is a radical $OR^3$. In this, $R^3$ has the aforementioned meanings and is in particular H, $C_1$-$C_4$-alkyl, phenyl or benzyl and specifically H. In this connection, the phenyl ring in phenyl and in benzyl may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen.

$R^2$ is preferably disposed in 5-position of the pyri(mi)din-2-one ring. $R^2$ is preferably selected from H, $C_1$-$C_4$-alkyl, in particular methyl, $C_1$-$C_2$-fluoroalkyl, in particular trifluoromethyl, halogen, in particular fluorine, and CN. In a particularly preferred embodiment, $R^2$ is $C_1$-$C_4$-alkyl, specifically methyl. In another particularly preferred embodiment, $R^2$ is hydrogen.

A very particularly preferred embodiment of the invention relates to compounds of the formula I in which $R^1$ is $OR^3$ and in particular OH, or is methyl, isopropyl, tert-butyl, $CF_3$, cyclobutyl, cyclohexyl, phenyl, p-fluorophenyl, m-fluorophenyl, o-fluorophenyl, p-methylphenyl, m-methylphenyl, o-methylphenyl or 2-furyl, and $R^2$ is in particular selected from H, halogen, CN, $CF_3$ and $C_1$-$C_4$-alkyl and specifically hydrogen, methyl, fluorine or chlorine.

A further very particularly preferred embodiment of the invention relates to compounds of the formula I in which $R^1$ is OH, phenyl, p-fluorophenyl, m-fluorophenyl, o-fluorophenyl, p-methylphenyl, m-methylphenyl, o-methylphenyl, in particular OH, and $R^2$ is in particular selected from H, fluorine, chlorine and $C_1$-$C_4$-alkyl and specifically is hydrogen, fluorine or methyl.

Q is preferably phenyl which optionally has 1, 2 or 3 substituents $R^Q$ which are selected independently of one another from OH, $C_1$-$C_6$-alkyl which is optionally completely or partly substituted by halogen, or halogen, cyano, $C_1$-$C_4$-alkoxy, $C_1$-$C_2$-haloalkoxy, $NR^4R^5$, $C_3$-$C_6$-cycloalkyl, or where 2 substituents bonded to adjacent C atoms of the phenyl are, together with the C atoms to which they are bonded, a fused, unsaturated 4-, 5- or 6-membered carbocycle or are a 4-, 5- or 6-membered heterocycle having 1 or 2 heteroatoms selected from O, N and S as ring members. $R^Q$ may also be $COOR^7$.

In a particularly preferred embodiment, Q is phenyl which has 1, 2 or 3 substituents $R^Q$ which are selected independently of one another from methyl, ethyl, n-propyl, isopropyl, tert-butyl, cyclopropyl, cyclobutyl, hydroxyl, chlorine, fluorine, trifluoromethyl, $OCF_3$, $OCHF_2$, CN, dimethylamino, methoxy or ethoxy.

In this embodiment, Q is for example 2-chlorophenyl, 2-fluorophenyl, 3-chlorophenyl, 3-fluorophenyl, 4-chlorophenyl, 4-fluorophenyl, 2-chloro-6-fluorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2-trifluoromethoxyphenyl, 3-trifluoromethoxyphenyl, 2-methoxycarbonylphenyl, 3-methoxycarbonylphenyl, 4-methoxycarbonylphenyl, 2-ethylphenyl, 3-ethylphenyl, 4-ethylphenyl, 2-ethoxyphenyl, 3-ethoxyphenyl, 4-ethoxyphenyl, 2-n-propylphenyl, 3-n-propylphenyl, 4-n-propylphenyl, 2-isopropylphenyl, 3-isopropylphenyl, 4-isopropylphenyl, 2-cyclopropylphenyl, 3-cyclopropylphenyl, 4-cyclopropylphenyl, 2-cyclobutylphenyl, 3-cyclobutylphenyl, 4-cyclobutylphenyl, 2-tert-butylphenyl, 3-tert-butylphenyl, 4-tert-butylphenyl, 4-trifluoromethoxyphenyl, 2-hydroxyphenyl, 3-hydroxyphenyl, 4-hydroxyphenyl, 2-cyanophenyl, 3-cyanophenyl, 4-cyanophenyl, 2-dimethylaminophenyl, 3-dimethylaminophenyl, 4-dimethylaminophenyl, 2,4,6-trimethylphenyl, 2,3,4-trimethoxyphenyl, 2,4,5-trimethoxyphenyl.

If Q is phenyl, it has in particular two substituents $R^Q$. The two substituents $R^Q$ are then particularly preferably located in position 2,3; 2,4 or 3,4 on the phenyl ring. Examples thereof are 2,3-dichlorophenyl, 2,4-dichlorophenyl, 3,4-dichlorophenyl, 2,3-difluorophenyl, 2,4-difluorophenyl, 3,4-difluorophenyl, 2-chloro-3-fluorophenyl, 2-chloro-4-fluorophenyl, 3-chloro-4-fluorophenyl, 3-chloro-2-fluorophenyl, 4-chloro-2-fluorophenyl, 4-chloro-3-fluorophenyl, 2-chloro-3-methylphenyl, 2-chloro-4-methylphenyl, 3-chloro-4-methylphenyl, 3-chloro-2-methylphenyl, 4-chloro-2-methylphenyl, 4-chloro-3-methylphenyl, 2-chloro-3-methoxyphenyl, 2-chloro-4-methoxyphenyl, 3-chloro-4-methoxyphenyl, 3-chloro-2-methoxyphenyl, 4-chloro-2-methoxyphenyl, 4-chloro-3-methoxyphenyl, 2-chloro-3-trifluormethoxyphenyl, 2-chloro-4-trifluormethoxyphenyl, 3-chloro-4-trifluormethoxyphenyl, 3-chloro-2-trifluormethoxyphenyl, 4-chloro-2-trifluormethoxyphenyl, 4-chloro-3-trifluormethoxyphenyl, 2,3-dimethylphenyl, 2,4-dimethylphenyl, 3,4-dimethylphenyl, 2,3-dimethoxyphenyl, 2,4-dimethoxyphenyl and 3,4-dimethoxyphenyl.

In a further particularly preferred embodiment, Q is phenyl which has 1 or, in particular, 2 substituents selected from halogen, specifically fluorine and chlorine, where preferably 1 halogen atom is disposed in the para position relative to the binding site to $A^2$. Q is in particular preferably 2,4-dichlorophenyl or 3,4-dichlorophenyl.

In another embodiment, Q is naphthyl or phenyl which carries a fused 5-membered heterocycle having 1 or 2 O atoms as ring members. In this embodiment, Q is for example naphth-1-yl, naphth-2-yl, 2-methyl-α-naphthyl, 1,3-benzodioxol-4-yl or 1,3-benzodioxol-5-yl.

In another embodiment, Q is 5- or 6-membered aromatic heterocyclyl having 1 or 2 heteroatoms selected from O, N and S, which may have 1 or 2 substituents. The substituents are preferably selected from chlorine and methyl. In this embodiment, Q is for example 2-pyridinyl, 3-pyridinyl, 4-pyridinyl, 4,6-dimethoxypyrimidin-2-yl, 2-thienyl, 3-thienyl, 4-thienyl, 2-furyl, 3-furyl, 4-furyl, 2-chlorothiazol-5-yl, 6-chloropyridin-2-yl, 1-methylimidazol-2-yl, 2-methylthiazol-5-yl.

In another embodiment, Q is 5- or 6-membered aromatic heterocyclyl having 1 or 2 heteroatoms selected from O, N and S, which carries a fused, unsaturated six-membered carbocycle and in particular a fused benzene ring. In this embodiment, Q is for example benzimidazol-2-yl, benzoxazol-2-yl or benzothiazol-2-yl.

Otherwise, the groups $R^3$, $R^4$, $R^5$, $R^6$, $R^7$ and $R^8$ preferably have the meanings indicated below:

$R^3$ is preferably H, $C_1$-$C_4$-alkyl, phenyl-substituted $C_1$-$C_4$-alkyl or $COR^{11}$. In this, $R^{11}$ has the meanings indicated for $R^8$ and is in particular $C_1$-$C_4$-alkyl. $R^3$ in groups $NR^3$ is preferably H, $C_1$-$C_4$-alkyl, phenyl-substituted $C_1$-$C_4$-alkyl or $COR^{11}$. $NR^3$ is particularly preferably NH, $NCH_3$, $NCOCH_3$ or $NCH_2$-phenyl. $R^3$ in the groups $C(O)NR^3$ and $NR^3C(O)$ is preferably H, $C_1$-$C_4$-alkyl, phenyl-substituted $C_1$-$C_4$-alkyl or $COR^{11}$. $C(O)NR^3$ is particularly preferably CONH, $CONCH_3$ or $CONCH_2$-phenyl. $NR^3C(O)$ is particularly preferably NHCO, $NCH_3CO$ or $N(CH_2$-phenyl$)CO$.

$R^3$ is preferably H, $C_1$-$C_4$-alkyl, $CF_3$, $CHF_2$ or phenyl. $OR^3$ is particularly preferably methoxy, trifluoromethoxy or phenoxy.

$R^4$ is preferably hydrogen or $C_1$-$C_4$-alkyl. $R^5$ is preferably hydrogen, $C_1$-$C_4$-alkyl, phenyl, benzyl or a group. $COR^{11}$. $R^4$ in substituents $CONR^4R^5$ is preferably H or $C_1$-$C_4$-alkyl, and $R^5$ is preferably H, $C_1$-$C_4$-alkyl or $COR^{11}$. $CONR^4R^5$ is particularly preferably CONH$_2$, CONHCH$_3$, CON(CH$_3$)$_2$ or C(O)NHC(O)CH$_3$. R$^4$ in substituents NR$^4$R$^5$ is preferably H, C$_1$-C$_4$-alkyl or phenyl-substituted C$_1$-C$_4$-alkyl and R$^5$ is H, C$_1$-C$_4$-alkyl or COR$^{11}$. NR$^4$R$^5$ is particularly preferably NH$_2$, NHCH$_3$, N(CH$_3$)$_2$, NH-benzyl or NHCOCH$_3$. R$^4$ in substituents SO$_2$NR$^4$R$^5$ is preferably H or C$_1$-C$_4$-alkyl and R$^5$ is preferably H, C$_1$-C$_4$-alkyl or COR$^{11}$. SO$_2$NR$^4$R$^5$ is particularly preferably sulfamoyl. R$^4$ and R$^5$ in the aforementioned groups may also form together with the nitrogen atom to which they are bonded a saturated or unsaturated 4-, 5- or 6-membered, preferably saturated nitrogen heterocycle which may have a further heteroatom such as N, S or O and which may be substituted by 1, 2, 3 or 4 alkyl groups. Examples of such heterocycles are piperidinyl, morpholinyl, pyrrolidinyl, 4-methylpiperazinyl and 4-methylpiperidinyl.

R$^6$ is preferably H, C$_1$-C$_4$-alkyl, phenyl or benzyl. R$^6$ in substituents SR$^6$ is preferably H, C$_1$-C$_4$-alkyl, phenyl or benzyl. R$^6$ in substituents SOR$^6$ is preferably phenyl or C$_1$-C$_4$-alkyl. R$^6$ in substituents SO$_2$R$^6$ is preferably H or C$_1$-C$_4$-alkyl. SO$_2$R$^6$ is particularly preferably methylsulfonyl.

R$^7$ in substituents COOR$^7$ is H or C$_1$-C$_4$-alkyl. COOR$^7$ is particularly preferably C$_1$-C$_4$-alkoxycarbonyl such as methoxycarbonyl, ethoxycarbonyl, n-propoxycarbonyl, i-propoxycarbonyl, n-butoxycarbonyl or t-butoxycarbonyl.

R$^8$ in the substituents COR$^8$ and OC(O)R$^8$ is preferably H, C$_1$-C$_4$-alkyl or phenyl. CORE is particularly preferably formyl, acetyl or benzoyl.

Among the substituted N-heterocyclic compounds of the invention, preference is given to the compounds of the general formula I.A

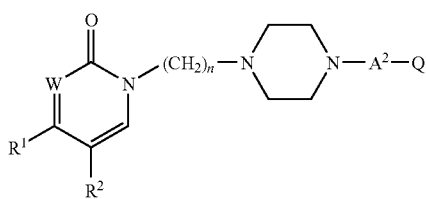

(I.A)

in which W, R$^1$, R$^2$, A$^2$ and Q have the aforementioned meanings, and n is 4, 5 or 6, in particular 4; and the tautomers of the compounds I.A, the physiologically acceptable salts of the compounds I.A and the physiologically acceptable salts of the tautomers of the compounds I.A.

Compounds of the formula I.A which may in particular be in the form of tautomers are those in which one or both of the radicals R$^1$ or R$^2$ are OH or NHR$^4$ in which R$^4$ has the aforementioned meanings.

Among the compounds of the general formula I.A, particular preference is given to the compounds of the general formula I.A-1

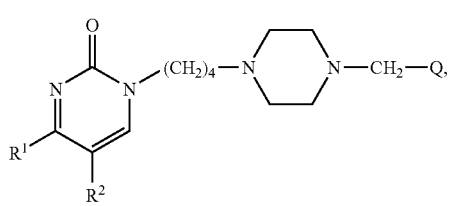

(I.A-1)

in which R$^1$ and R$^2$ have the aforementioned meanings, in particular the meanings indicated as preferred; and Q is phenyl which is substituted by 1 or 2 groups R$^a$ as defined above, which may in each case be identical or different and also be linked to each other.

Examples of such compounds are the compounds I.A-1.1 to I.A-1.1386 detailed in the following Table 1, where the variables R$^1$, R$^2$ and Q in each case together have the meaning indicated in one line of Table 1, and for R$^1$=OH the tautomers of these compounds.

TABLE 1

| | R$^1$ | R$^2$ | Q |
|---|---|---|---|
| 1 | phenyl | H | 2-chloro-4-fluorophenyl |
| 2 | phenyl | CH$_3$ | 2-chloro-4-fluorophenyl |
| 3 | H | CH$_3$ | 2-chloro-4-fluorophenyl |
| 4 | CH$_3$ | H | 2-chloro-4-fluorophenyl |
| 5 | OH | H | 2-chloro-4-fluorophenyl |
| 6 | C(CH$_3$)$_3$ | H | 2-chloro-4-fluorophenyl |
| 7 | CF$_3$ | H | 2-chloro-4-fluorophenyl |
| 8 | CH(CH$_3$)$_2$ | H | 2-chloro-4-fluorophenyl |
| 9 | 2-furyl | H | 2-chloro-4-fluorophenyl |
| 10 | cyclohexyl | H | 2-chloro-4-fluorophenyl |
| 11 | cyclobutyl | H | 2-chloro-4-fluorophenyl |
| 12 | 4-methylphenyl | H | 2-chloro-4-fluorophenyl |
| 13 | 2-methylphenyl | H | 2-chloro-4-fluorophenyl |
| 14 | 2-fluorophenyl | H | 2-chloro-4-fluorophenyl |
| 15 | 3-fluorophenyl | H | 2-chloro-4-fluorophenyl |
| 16 | 4-fluorophenyl | H | 2-chloro-4-fluorophenyl |
| 17 | OH | CH$_3$ | 2-chloro-4-fluorophenyl |
| 18 | OH | CF$_3$ | 2-chloro-4-fluorophenyl |
| 19 | OH | F | 2-chloro-4-fluorophenyl |
| 20 | OH | CN | 2-chloro-4-fluorophenyl |
| 21 | OH | Cl | 2-chloro-4-fluorophenyl |
| 22 | OH | C$_2$H$_5$ | 2-chloro-4-fluorophenyl |
| 23 | phenyl | H | 2-chloro-3-fluorophenyl |
| 24 | phenyl | CH$_3$ | 2-chloro-3-fluorophenyl |
| 25 | H | CH$_3$ | 2-chloro-3-fluorophenyl |
| 26 | CH$_3$ | H | 2-chloro-3-fluorophenyl |
| 27 | OH | H | 2-chloro-3-fluorophenyl |
| 28 | C(CH$_3$)$_3$ | H | 2-chloro-3-fluorophenyl |
| 29 | CF$_3$ | H | 2-chloro-3-fluorophenyl |
| 30 | CH(CH$_3$)$_2$ | H | 2-chloro-3-fluorophenyl |
| 31 | 2-furyl | H | 2-chloro-3-fluorophenyl |
| 32 | cyclohexyl | H | 2-chloro-3-fluorophenyl |
| 33 | cyclobutyl | H | 2-chloro-3-fluorophenyl |
| 34 | 4-methylphenyl | H | 2-chloro-3-fluorophenyl |
| 35 | 2-methylphenyl | H | 2-chloro-3-fluorophenyl |
| 36 | 2-fluorophenyl | H | 2-chloro-3-fluorophenyl |
| 37 | 3-fluorophenyl | H | 2-chloro-3-fluorophenyl |
| 38 | 4-fluorophenyl | H | 2-chloro-3-fluorophenyl |
| 39 | OH | CH$_3$ | 2-chloro-3-fluorophenyl |
| 40 | OH | CF$_3$ | 2-chloro-3-fluorophenyl |
| 41 | OH | F | 2-chloro-3-fluorophenyl |
| 42 | OH | CN | 2-chloro-3-fluorophenyl |
| 43 | OH | Cl | 2-chloro-3-fluorophenyl |
| 44 | OH | C$_2$H$_5$ | 2-chloro-3-fluorophenyl |
| 45 | phenyl | H | 3-chloro-4-fluorophenyl |
| 46 | phenyl | CH$_3$ | 3-chloro-4-fluorophenyl |
| 47 | H | CH$_3$ | 3-chloro-4-fluorophenyl |
| 48 | CH$_3$ | H | 3-chloro-4-fluorophenyl |
| 49 | OH | H | 3-chloro-4-fluorophenyl |
| 50 | C(CH$_3$)$_3$ | H | 3-chloro-4-fluorophenyl |
| 51 | CF$_3$ | H | 3-chloro-4-fluorophenyl |
| 52 | CH(CH$_3$)$_2$ | H | 3-chloro-4-fluorophenyl |
| 53 | 2-furyl | H | 3-chloro-4-fluorophenyl |
| 54 | cyclohexyl | H | 3-chloro-4-fluorophenyl |
| 55 | cyclobutyl | H | 3-chloro-4-fluorophenyl |
| 56 | 4-methylphenyl | H | 3-chloro-4-fluorophenyl |
| 57 | 2-methylphenyl | H | 3-chloro-4-fluorophenyl |
| 58 | 2-fluorophenyl | H | 3-chloro-4-fluorophenyl |
| 59 | 3-fluorophenyl | H | 3-chloro-4-fluorophenyl |
| 60 | 4-fluorophenyl | H | 3-chloro-4-fluorophenyl |
| 61 | OH | CH$_3$ | 3-chloro-4-fluorophenyl |
| 62 | OH | CF$_3$ | 3-chloro-4-fluorophenyl |
| 63 | OH | F | 3-chloro-4-fluorophenyl |
| 64 | OH | CN | 3-chloro-4-fluorophenyl |
| 65 | OH | Cl | 3-chloro-4-fluorophenyl |
| 66 | OH | C$_2$H$_5$ | 3-chloro-4-fluorophenyl |
| 67 | phenyl | H | 2,4-dichlorophenyl |

TABLE 1-continued

| | R¹ | R² | Q |
|---|---|---|---|
| 68 | phenyl | CH₃ | 2,4-dichlorophenyl |
| 69 | H | CH₃ | 2,4-dichlorophenyl |
| 70 | CH₃ | H | 2,4-dichlorophenyl |
| 71 | OH | H | 2,4-dichlorophenyl |
| 72 | C(CH₃)₃ | H | 2,4-dichlorophenyl |
| 73 | CF₃ | H | 2,4-dichlorophenyl |
| 74 | CH(CH₃)₂ | H | 2,4-dichlorophenyl |
| 75 | 2-furyl | H | 2,4-dichlorophenyl |
| 76 | cyclohexyl | H | 2,4-dichlorophenyl |
| 77 | cyclobutyl | H | 2,4-dichlorophenyl |
| 78 | 4-methylphenyl | H | 2,4-dichlorophenyl |
| 79 | 2-methylphenyl | H | 2,4-dichlorophenyl |
| 80 | 2-fluorophenyl | H | 2,4-dichlorophenyl |
| 81 | 3-fluorophenyl | H | 2,4-dichlorophenyl |
| 82 | 4-fluorophenyl | H | 2,4-dichlorophenyl |
| 83 | OH | CH₃ | 2,4-dichlorophenyl |
| 84 | OH | CF₃ | 2,4-dichlorophenyl |
| 85 | OH | F | 2,4-dichlorophenyl |
| 86 | OH | CN | 2,4-dichlorophenyl |
| 87 | OH | Cl | 2,4-dichlorophenyl |
| 88 | OH | C₂H₅ | 2,4-dichlorophenyl |
| 89 | phenyl | H | 3,4-dichlorophenyl |
| 90 | phenyl | CH₃ | 3,4-dichlorophenyl |
| 91 | H | CH₃ | 3,4-dichlorophenyl |
| 92 | CH₃ | H | 3,4-dichlorophenyl |
| 93 | OH | H | 3,4-dichlorophenyl |
| 94 | C(CH₃)₃ | H | 3,4-dichlorophenyl |
| 95 | CF₃ | H | 3,4-dichlorophenyl |
| 96 | CH(CH₃)₂ | H | 3,4-dichlorophenyl |
| 97 | 2-furyl | H | 3,4-dichlorophenyl |
| 98 | cyclohexyl | H | 3,4-dichlorophenyl |
| 99 | cyclobutyl | H | 3,4-dichlorophenyl |
| 100 | 4-methylphenyl | H | 3,4-dichlorophenyl |
| 101 | 2-methylphenyl | H | 3,4-dichlorophenyl |
| 102 | 2-fluorophenyl | H | 3,4-dichlorophenyl |
| 103 | 3-fluorophenyl | H | 3,4-dichlorophenyl |
| 104 | 4-fluorophenyl | H | 3,4-dichlorophenyl |
| 105 | OH | CH₃ | 3,4-dichlorophenyl |
| 106 | OH | CF₃ | 3,4-dichlorophenyl |
| 107 | OH | F | 3,4-dichlorophenyl |
| 108 | OH | CN | 3,4-dichlorophenyl |
| 109 | OH | Cl | 3,4-dichlorophenyl |
| 110 | OH | C₂H₅ | 3,4-dichlorophenyl |
| 111 | phenyl | H | 2,4-dimethoxyphenyl |
| 112 | phenyl | CH₃ | 2,4-dimethoxyphenyl |
| 113 | H | CH₃ | 2,4-dimethoxyphenyl |
| 114 | CH₃ | H | 2,4-dimethoxyphenyl |
| 115 | OH | H | 2,4-dimethoxyphenyl |
| 116 | C(CH₃)₃ | H | 2,4-dimethoxyphenyl |
| 117 | CF₃ | H | 2,4-dimethoxyphenyl |
| 118 | CH(CH₃)₂ | H | 2,4-dimethoxyphenyl |
| 119 | 2-furyl | H | 2,4-dimethoxyphenyl |
| 120 | cyclohexyl | H | 2,4-dimethoxyphenyl |
| 121 | cyclobutyl | H | 2,4-dimethoxyphenyl |
| 122 | 4-methylphenyl | H | 2,4-dimethoxyphenyl |
| 123 | 2-methylphenyl | H | 2,4-dimethoxyphenyl |
| 124 | 2-fluorophenyl | H | 2,4-dimethoxyphenyl |
| 125 | 3-fluorophenyl | H | 2,4-dimethoxyphenyl |
| 126 | 4-fluorophenyl | H | 2,4-dimethoxyphenyl |
| 127 | OH | CH₃ | 2,4-dimethoxyphenyl |
| 128 | OH | CF₃ | 2,4-dimethoxyphenyl |
| 129 | OH | F | 2,4-dimethoxyphenyl |
| 130 | OH | CN | 2,4-dimethoxyphenyl |
| 131 | OH | Cl | 2,4-dimethoxyphenyl |
| 132 | OH | C₂H₅ | 2,4-dimethoxyphenyl |
| 133 | phenyl | H | 3,4-dimethoxyphenyl |
| 134 | phenyl | CH₃ | 3,4-dimethoxyphenyl |
| 135 | H | CH₃ | 3,4-dimethoxyphenyl |
| 136 | CH₃ | H | 3,4-dimethoxyphenyl |
| 137 | OH | H | 3,4-dimethoxyphenyl |
| 138 | C(CH₃)₃ | H | 3,4-dimethoxyphenyl |
| 139 | CF₃ | H | 3,4-dimethoxyphenyl |
| 140 | CH(CH₃)₂ | H | 3,4-dimethoxyphenyl |
| 141 | 2-furyl | H | 3,4-dimethoxyphenyl |
| 142 | cyclohexyl | H | 3,4-dimethoxyphenyl |
| 143 | cyclobutyl | H | 3,4-dimethoxyphenyl |
| 144 | 4-methylphenyl | H | 3,4-dimethoxyphenyl |
| 145 | 2-methylphenyl | H | 3,4-dimethoxyphenyl |
| 146 | 2-fluorophenyl | H | 3,4-dimethoxyphenyl |
| 147 | 3-fluorophenyl | H | 3,4-dimethoxyphenyl |
| 148 | 4-fluorophenyl | H | 3,4-dimethoxyphenyl |
| 149 | OH | CH₃ | 3,4-dimethoxyphenyl |
| 150 | OH | CF₃ | 3,4-dimethoxyphenyl |
| 151 | OH | F | 3,4-dimethoxyphenyl |
| 152 | OH | CN | 3,4-dimethoxyphenyl |
| 153 | OH | Cl | 3,4-dimethoxyphenyl |
| 154 | OH | C₂H₅ | 3,4-dimethoxyphenyl |
| 155 | phenyl | H | 2,4-dimethylphenyl |
| 156 | phenyl | CH₃ | 2,4-dimethylphenyl |
| 157 | H | CH₃ | 2,4-dimethylphenyl |
| 158 | CH₃ | H | 2,4-dimethylphenyl |
| 159 | OH | H | 2,4-dimethylphenyl |
| 160 | C(CH₃)₃ | H | 2,4-dimethylphenyl |
| 161 | CF₃ | H | 2,4-dimethylphenyl |
| 162 | CH(CH₃)₂ | H | 2,4-dimethylphenyl |
| 163 | 2-furyl | H | 2,4-dimethylphenyl |
| 164 | cyclohexyl | H | 2,4-dimethylphenyl |
| 165 | cyclobutyl | H | 2,4-dimethylphenyl |
| 166 | 4-methylphenyl | H | 2,4-dimethylphenyl |
| 167 | 2-methylphenyl | H | 2,4-dimethylphenyl |
| 168 | 2-fluorophenyl | H | 2,4-dimethylphenyl |
| 169 | 3-fluorophenyl | H | 2,4-dimethylphenyl |
| 170 | 4-fluorophenyl | H | 2,4-dimethylphenyl |
| 171 | OH | CH₃ | 2,4-dimethylphenyl |
| 172 | OH | CF₃ | 2,4-dimethylphenyl |
| 173 | OH | F | 2,4-dimethylphenyl |
| 174 | OH | CN | 2,4-dimethylphenyl |
| 175 | OH | Cl | 2,4-dimethylphenyl |
| 176 | OH | C₂H₅ | 2,4-dimethylphenyl |
| 177 | phenyl | H | 3,4-dimethylphenyl |
| 178 | phenyl | CH₃ | 3,4-dimethylphenyl |
| 179 | H | CH₃ | 3,4-dimethylphenyl |
| 180 | CH₃ | H | 3,4-dimethylphenyl |
| 181 | OH | H | 3,4-dimethylphenyl |
| 182 | C(CH₃)₃ | H | 3,4-dimethylphenyl |
| 183 | CF₃ | H | 3,4-dimethylphenyl |
| 184 | CH(CH₃)₂ | H | 3,4-dimethylphenyl |
| 185 | 2-furyl | H | 3,4-dimethylphenyl |
| 186 | cyclohexyl | H | 3,4-dimethylphenyl |
| 187 | cyclobutyl | H | 3,4-dimethylphenyl |
| 188 | 4-methylphenyl | H | 3,4-dimethylphenyl |
| 189 | 2-methylphenyl | H | 3,4-dimethylphenyl |
| 190 | 2-fluorophenyl | H | 3,4-dimethylphenyl |
| 191 | 3-fluorophenyl | H | 3,4-dimethylphenyl |
| 192 | 4-fluorophenyl | H | 3,4-dimethylphenyl |
| 193 | OH | CH₃ | 3,4-dimethylphenyl |
| 194 | OH | CF₃ | 3,4-dimethylphenyl |
| 195 | OH | F | 3,4-dimethylphenyl |
| 196 | OH | CN | 3,4-dimethylphenyl |
| 197 | OH | Cl | 3,4-dimethylphenyl |
| 198 | OH | C₂H₅ | 3,4-dimethylphenyl |
| 199 | phenyl | H | 2-chloro-4-methylphenyl |
| 200 | phenyl | CH₃ | 2-chloro-4-methylphenyl |
| 201 | H | CH₃ | 2-chloro-4-methylphenyl |
| 202 | CH₃ | H | 2-chloro-4-methylphenyl |
| 203 | OH | H | 2-chloro-4-methylphenyl |
| 204 | C(CH₃)₃ | H | 2-chloro-4-methylphenyl |
| 205 | CF₃ | H | 2-chloro-4-methylphenyl |
| 206 | CH(CH₃)₂ | H | 2-chloro-4-methylphenyl |
| 207 | 2-furyl | H | 2-chloro-4-methylphenyl |
| 208 | cyclohexyl | H | 2-chloro-4-methylphenyl |
| 209 | cyclobutyl | H | 2-chloro-4-methylphenyl |
| 210 | 4-methylphenyl | H | 2-chloro-4-methylphenyl |
| 211 | 2-methylphenyl | H | 2-chloro-4-methylphenyl |
| 212 | 2-fluorophenyl | H | 2-chloro-4-methylphenyl |
| 213 | 3-fluorophenyl | H | 2-chloro-4-methylphenyl |
| 214 | 4-fluorophenyl | H | 2-chloro-4-methylphenyl |
| 215 | OH | CH₃ | 2-chloro-4-methylphenyl |
| 216 | OH | CF₃ | 2-chloro-4-methylphenyl |
| 217 | OH | F | 2-chloro-4-methylphenyl |
| 218 | OH | CN | 2-chloro-4-methylphenyl |
| 219 | OH | Cl | 2-chloro-4-methylphenyl |
| 220 | OH | C₂H₅ | 2-chloro-4-methylphenyl |
| 221 | phenyl | H | 4-chloro-2-fluorophenyl |
| 222 | phenyl | CH₃ | 4-chloro-2-fluorophenyl |
| 223 | H | CH₃ | 4-chloro-2-fluorophenyl |

TABLE 1-continued

| | R¹ | R² | Q |
|---|---|---|---|
| 224 | CH₃ | H | 4-chloro-2-fluorophenyl |
| 225 | OH | H | 4-chloro-2-fluorophenyl |
| 226 | C(CH₃)₃ | H | 4-chloro-2-fluorophenyl |
| 227 | CF₃ | H | 4-chloro-2-fluorophenyl |
| 228 | CH(CH₃)₂ | H | 4-chloro-2-fluorophenyl |
| 229 | 2-furyl | H | 4-chloro-2-fluorophenyl |
| 230 | cyclohexyl | H | 4-chloro-2-fluorophenyl |
| 231 | cyclobutyl | H | 4-chloro-2-fluorophenyl |
| 232 | 4-methylphenyl | H | 4-chloro-2-fluorophenyl |
| 233 | 2-methylphenyl | H | 4-chloro-2-fluorophenyl |
| 234 | 2-fluorophenyl | H | 4-chloro-2-fluorophenyl |
| 235 | 3-fluorophenyl | H | 4-chloro-2-fluorophenyl |
| 236 | 4-fluorophenyl | H | 4-chloro-2-fluorophenyl |
| 237 | OH | CH₃ | 4-chloro-2-fluorophenyl |
| 238 | OH | CF₃ | 4-chloro-2-fluorophenyl |
| 239 | OH | F | 4-chloro-2-fluorophenyl |
| 240 | OH | CN | 4-chloro-2-fluorophenyl |
| 241 | OH | Cl | 4-chloro-2-fluorophenyl |
| 242 | OH | C₂H₅ | 4-chloro-2-fluorophenyl |
| 243 | phenyl | H | 4-chloro-3-fluorophenyl |
| 244 | phenyl | CH₃ | 4-chloro-3-fluorophenyl |
| 245 | H | CH₃ | 4-chloro-3-fluorophenyl |
| 246 | CH₃ | H | 4-chloro-3-fluorophenyl |
| 247 | OH | H | 4-chloro-3-fluorophenyl |
| 248 | C(CH₃)₃ | H | 4-chloro-3-fluorophenyl |
| 249 | CF₃ | H | 4-chloro-3-fluorophenyl |
| 250 | CH(CH₃)₂ | H | 4-chloro-3-fluorophenyl |
| 251 | 2-furyl | H | 4-chloro-3-fluorophenyl |
| 252 | cyclohexyl | H | 4-chloro-3-fluorophenyl |
| 253 | cyclobutyl | H | 4-chloro-3-fluorophenyl |
| 254 | 4-methylphenyl | H | 4-chloro-3-fluorophenyl |
| 255 | 2-methylphenyl | H | 4-chloro-3-fluorophenyl |
| 256 | 2-fluorophenyl | H | 4-chloro-3-fluorophenyl |
| 257 | 3-fluorophenyl | H | 4-chloro-3-fluorophenyl |
| 258 | 4-fluorophenyl | H | 4-chloro-3-fluorophenyl |
| 259 | OH | CH₃ | 4-chloro-3-fluorophenyl |
| 260 | OH | CF₃ | 4-chloro-3-fluorophenyl |
| 261 | OH | F | 4-chloro-3-fluorophenyl |
| 262 | OH | CN | 4-chloro-3-fluorophenyl |
| 263 | OH | Cl | 4-chloro-3-fluorophenyl |
| 264 | OH | C₂H₅ | 4-chloro-3-fluorophenyl |
| 265 | phenyl | H | 3-chloro-2-fluorophenyl |
| 266 | phenyl | CH₃ | 3-chloro-2-fluorophenyl |
| 267 | H | CH₃ | 3-chloro-2-fluorophenyl |
| 268 | CH₃ | H | 3-chloro-2-fluorophenyl |
| 269 | OH | H | 3-chloro-2-fluorophenyl |
| 270 | C(CH₃)₃ | H | 3-chloro-2-fluorophenyl |
| 271 | CF₃ | H | 3-chloro-2-fluorophenyl |
| 272 | CH(CH₃)₂ | H | 3-chloro-2-fluorophenyl |
| 273 | 2-furyl | H | 3-chloro-2-fluorophenyl |
| 274 | cyclohexyl | H | 3-chloro-2-fluorophenyl |
| 275 | cyclobutyl | H | 3-chloro-2-fluorophenyl |
| 276 | 4-methylphenyl | H | 3-chloro-2-fluorophenyl |
| 277 | 2-methylphenyl | H | 3-chloro-2-fluorophenyl |
| 278 | 2-fluorophenyl | H | 3-chloro-2-fluorophenyl |
| 279 | 3-fluorophenyl | H | 3-chloro-2-fluorophenyl |
| 280 | 4-fluorophenyl | H | 3-chloro-2-fluorophenyl |
| 281 | OH | CH₃ | 3-chloro-2-fluorophenyl |
| 282 | OH | CF₃ | 3-chloro-2-fluorophenyl |
| 283 | OH | F | 3-chloro-2-fluorophenyl |
| 284 | OH | CN | 3-chloro-2-fluorophenyl |
| 285 | OH | Cl | 3-chloro-2-fluorophenyl |
| 286 | OH | C₂H₅ | 3-chloro-2-fluorophenyl |
| 287 | phenyl | H | 2-chlorophenyl |
| 288 | phenyl | CH₃ | 2-chlorophenyl |
| 289 | H | CH₃ | 2-chlorophenyl |
| 290 | CH₃ | H | 2-chlorophenyl |
| 291 | OH | H | 2-chlorophenyl |
| 292 | C(CH₃)₃ | H | 2-chlorophenyl |
| 293 | CF₃ | H | 2-chlorophenyl |
| 294 | CH(CH₃)₂ | H | 2-chlorophenyl |
| 295 | 2-furyl | H | 2-chlorophenyl |
| 296 | cyclohexyl | H | 2-chlorophenyl |
| 297 | cyclobutyl | H | 2-chlorophenyl |
| 298 | 4-methylphenyl | H | 2-chlorophenyl |
| 299 | 2-methylphenyl | H | 2-chlorophenyl |
| 300 | 2-fluorophenyl | H | 2-chlorophenyl |
| 301 | 3-fluorophenyl | H | 2-chlorophenyl |
| 302 | 4-fluorophenyl | H | 2-chlorophenyl |
| 303 | OH | CH₃ | 2-chlorophenyl |
| 304 | OH | CF₃ | 2-chlorophenyl |
| 305 | OH | F | 2-chlorophenyl |
| 306 | OH | CN | 2-chlorophenyl |
| 307 | OH | Cl | 2-chlorophenyl |
| 308 | OH | C₂H₅ | 2-chlorophenyl |
| 309 | phenyl | H | 4-chlorophenyl |
| 310 | phenyl | CH₃ | 4-chlorophenyl |
| 311 | H | CH₃ | 4-chlorophenyl |
| 312 | CH₃ | H | 4-chlorophenyl |
| 313 | OH | H | 4-chlorophenyl |
| 314 | C(CH₃)₃ | H | 4-chlorophenyl |
| 315 | CF₃ | H | 4-chlorophenyl |
| 316 | CH(CH₃)₂ | H | 4-chlorophenyl |
| 317 | 2-furyl | H | 4-chlorophenyl |
| 318 | cyclohexyl | H | 4-chlorophenyl |
| 319 | cyclobutyl | H | 4-chlorophenyl |
| 320 | 4-methylphenyl | H | 4-chlorophenyl |
| 321 | 2-methylphenyl | H | 4-chlorophenyl |
| 322 | 2-fluorophenyl | H | 4-chlorophenyl |
| 323 | 3-fluorophenyl | H | 4-chlorophenyl |
| 324 | 4-fluorophenyl | H | 4-chlorophenyl |
| 325 | OH | CH₃ | 4-chlorophenyl |
| 326 | OH | CF₃ | 4-chlorophenyl |
| 327 | OH | F | 4-chlorophenyl |
| 328 | OH | CN | 4-chlorophenyl |
| 329 | OH | Cl | 4-chlorophenyl |
| 330 | OH | C₂H₅ | 4-chlorophenyl |
| 331 | phenyl | H | 3-chlorophenyl |
| 332 | phenyl | CH₃ | 3-chlorophenyl |
| 333 | H | CH₃ | 3-chlorophenyl |
| 334 | CH₃ | H | 3-chlorophenyl |
| 335 | OH | H | 3-chlorophenyl |
| 336 | C(CH₃)₃ | H | 3-chlorophenyl |
| 337 | CF₃ | H | 3-chlorophenyl |
| 338 | CH(CH₃)₂ | H | 3-chlorophenyl |
| 339 | 2-furyl | H | 3-chlorophenyl |
| 340 | cyclohexyl | H | 3-chlorophenyl |
| 341 | cyclobutyl | H | 3-chlorophenyl |
| 342 | 4-methylphenyl | H | 3-chlorophenyl |
| 343 | 2-methylphenyl | H | 3-chlorophenyl |
| 344 | 2-fluorophenyl | H | 3-chlorophenyl |
| 345 | 3-fluorophenyl | H | 3-chlorophenyl |
| 346 | 4-fluorophenyl | H | 3-chlorophenyl |
| 347 | OH | CH₃ | 3-chlorophenyl |
| 348 | OH | CF₃ | 3-chlorophenyl |
| 349 | OH | F | 3-chlorophenyl |
| 350 | OH | CN | 3-chlorophenyl |
| 351 | OH | Cl | 3-chlorophenyl |
| 352 | OH | C₂H₅ | 3-chlorophenyl |
| 353 | phenyl | H | 4-fluorophenyl |
| 354 | phenyl | CH₃ | 4-fluorophenyl |
| 355 | H | CH₃ | 4-fluorophenyl |
| 356 | CH₃ | H | 4-fluorophenyl |
| 357 | OH | H | 4-fluorophenyl |
| 358 | C(CH₃)₃ | H | 4-fluorophenyl |
| 359 | CF₃ | H | 4-fluorophenyl |
| 360 | CH(CH₃)₂ | H | 4-fluorophenyl |
| 361 | 2-furyl | H | 4-fluorophenyl |
| 362 | cyclohexyl | H | 4-fluorophenyl |
| 363 | cyclobutyl | H | 4-fluorophenyl |
| 364 | 4-methylphenyl | H | 4-fluorophenyl |
| 365 | 2-methylphenyl | H | 4-fluorophenyl |
| 366 | 2-fluorophenyl | H | 4-fluorophenyl |
| 367 | 3-fluorophenyl | H | 4-fluorophenyl |
| 368 | 4-fluorophenyl | H | 4-fluorophenyl |
| 369 | OH | CH₃ | 4-fluorophenyl |
| 370 | OH | CF₃ | 4-fluorophenyl |
| 371 | OH | F | 4-fluorophenyl |
| 372 | OH | CN | 4-fluorophenyl |
| 373 | OH | Cl | 4-fluorophenyl |
| 374 | OH | C₂H₅ | 4-fluorophenyl |
| 375 | phenyl | H | 2-fluorophenyl |
| 376 | phenyl | CH₃ | 2-fluorophenyl |
| 377 | H | CH₃ | 2-fluorophenyl |
| 378 | CH₃ | H | 2-fluorophenyl |
| 379 | OH | H | 2-fluorophenyl |

TABLE 1-continued

| | R¹ | R² | Q |
|---|---|---|---|
| 380 | C(CH$_3$)$_3$ | H | 2-fluorophenyl |
| 381 | CF$_3$ | H | 2-fluorophenyl |
| 382 | CH(CH$_3$)$_2$ | H | 2-fluorophenyl |
| 383 | 2-furyl | H | 2-fluorophenyl |
| 384 | cyclohexyl | H | 2-fluorophenyl |
| 385 | cyclobutyl | H | 2-fluorophenyl |
| 386 | 4-methylphenyl | H | 2-fluorophenyl |
| 387 | 2-methylphenyl | H | 2-fluorophenyl |
| 388 | 2-fluorophenyl | H | 2-fluorophenyl |
| 389 | 3-fluorophenyl | H | 2-fluorophenyl |
| 390 | 4-fluorophenyl | H | 2-fluorophenyl |
| 391 | OH | CH$_3$ | 2-fluorophenyl |
| 392 | OH | CF$_3$ | 2-fluorophenyl |
| 393 | OH | F | 2-fluorophenyl |
| 394 | OH | CN | 2-fluorophenyl |
| 395 | OH | Cl | 2-fluorophenyl |
| 396 | OH | C$_2$H$_5$ | 2-fluorophenyl |
| 397 | phenyl | H | 3-fluorophenyl |
| 398 | phenyl | CH$_3$ | 3-fluorophenyl |
| 399 | H | CH$_3$ | 3-fluorophenyl |
| 400 | CH$_3$ | H | 3-fluorophenyl |
| 401 | OH | H | 3-fluorophenyl |
| 402 | C(CH$_3$)$_3$ | H | 3-fluorophenyl |
| 403 | CF$_3$ | H | 3-fluorophenyl |
| 404 | CH(CH$_3$)$_2$ | H | 3-fluorophenyl |
| 405 | 2-furyl | H | 3-fluorophenyl |
| 406 | cyclohexyl | H | 3-fluorophenyl |
| 407 | cyclobutyl | H | 3-fluorophenyl |
| 408 | 4-methylphenyl | H | 3-fluorophenyl |
| 409 | 2-methylphenyl | H | 3-fluorophenyl |
| 410 | 2-fluorophenyl | H | 3-fluorophenyl |
| 411 | 3-fluorophenyl | H | 3-fluorophenyl |
| 412 | 4-fluorophenyl | H | 3-fluorophenyl |
| 413 | OH | CH$_3$ | 3-fluorophenyl |
| 414 | OH | CF$_3$ | 3-fluorophenyl |
| 415 | OH | F | 3-fluorophenyl |
| 416 | OH | CN | 3-fluorophenyl |
| 417 | OH | Cl | 3-fluorophenyl |
| 418 | OH | C$_2$H$_5$ | 3-fluorophenyl |
| 419 | phenyl | H | 2-chloro-3-methylphenyl |
| 420 | phenyl | CH$_3$ | 2-chloro-3-methylphenyl |
| 421 | H | CH$_3$ | 2-chloro-3-methylphenyl |
| 422 | CH$_3$ | H | 2-chloro-3-methylphenyl |
| 423 | OH | H | 2-chloro-3-methylphenyl |
| 424 | C(CH$_3$)$_3$ | H | 2-chloro-3-methylphenyl |
| 425 | CF$_3$ | H | 2-chloro-3-methylphenyl |
| 426 | CH(CH$_3$)$_2$ | H | 2-chloro-3-methylphenyl |
| 427 | 2-furyl | H | 2-chloro-3-methylphenyl |
| 428 | cyclohexyl | H | 2-chloro-3-methylphenyl |
| 429 | cyclobutyl | H | 2-chloro-3-methylphenyl |
| 430 | 4-methylphenyl | H | 2-chloro-3-methylphenyl |
| 431 | 2-methylphenyl | H | 2-chloro-3-methylphenyl |
| 432 | 2-fluorophenyl | H | 2-chloro-3-methylphenyl |
| 433 | 3-fluorophenyl | H | 2-chloro-3-methylphenyl |
| 434 | 4-fluorophenyl | H | 2-chloro-3-methylphenyl |
| 435 | OH | CH$_3$ | 2-chloro-3-methylphenyl |
| 436 | OH | CF$_3$ | 2-chloro-3-methylphenyl |
| 437 | OH | F | 2-chloro-3-methylphenyl |
| 438 | OH | CN | 2-chloro-3-methylphenyl |
| 439 | OH | Cl | 2-chloro-3-methylphenyl |
| 440 | OH | C$_2$H$_5$ | 2-chloro-3-methylphenyl |
| 441 | phenyl | H | 3-chloro-4-methylphenyl |
| 442 | phenyl | CH$_3$ | 3-chloro-4-methylphenyl |
| 443 | H | CH$_3$ | 3-chloro-4-methylphenyl |
| 444 | CH$_3$ | H | 3-chloro-4-methylphenyl |
| 445 | OH | H | 3-chloro-4-methylphenyl |
| 446 | C(CH$_3$)$_3$ | H | 3-chloro-4-methylphenyl |
| 447 | CF$_3$ | H | 3-chloro-4-methylphenyl |
| 448 | CH(CH$_3$)$_2$ | H | 3-chloro-4-methylphenyl |
| 449 | 2-furyl | H | 3-chloro-4-methylphenyl |
| 450 | cyclohexyl | H | 3-chloro-4-methylphenyl |
| 451 | cyclobutyl | H | 3-chloro-4-methylphenyl |
| 452 | 4-methylphenyl | H | 3-chloro-4-methylphenyl |
| 453 | 2-methylphenyl | H | 3-chloro-4-methylphenyl |
| 454 | 2-fluorophenyl | H | 3-chloro-4-methylphenyl |
| 455 | 3-fluorophenyl | H | 3-chloro-4-methylphenyl |
| 456 | 4-fluorophenyl | H | 3-chloro-4-methylphenyl |
| 457 | OH | CH$_3$ | 3-chloro-4-methylphenyl |
| 458 | OH | CF$_3$ | 3-chloro-4-methylphenyl |
| 459 | OH | F | 3-chloro-4-methylphenyl |
| 460 | OH | CN | 3-chloro-4-methylphenyl |
| 461 | OH | Cl | 3-chloro-4-methylphenyl |
| 462 | OH | C$_2$H$_5$ | 3-chloro-4-methylphenyl |
| 463 | phenyl | CH$_3$ | 3-chloro-2-methylphenyl |
| 464 | phenyl | CH$_3$ | 3-chloro-2-methylphenyl |
| 465 | H | CH$_3$ | 3-chloro-2-methylphenyl |
| 466 | CH$_3$ | H | 3-chloro-2-methylphenyl |
| 467 | OH | H | 3-chloro-2-methylphenyl |
| 468 | C(CH$_3$)$_3$ | H | 3-chloro-2-methylphenyl |
| 469 | CF$_3$ | H | 3-chloro-2-methylphenyl |
| 470 | CH(CH$_3$)$_2$ | H | 3-chloro-2-methylphenyl |
| 471 | 2-furyl | H | 3-chloro-2-methylphenyl |
| 472 | cyclohexyl | H | 3-chloro-2-methylphenyl |
| 473 | cyclobutyl | H | 3-chloro-2-methylphenyl |
| 474 | 4-methylphenyl | H | 3-chloro-2-methylphenyl |
| 475 | 2-methylphenyl | H | 3-chloro-2-methylphenyl |
| 476 | 2-fluorophenyl | H | 3-chloro-2-methylphenyl |
| 477 | 3-fluorophenyl | H | 3-chloro-2-methylphenyl |
| 478 | 4-fluorophenyl | H | 3-chloro-2-methylphenyl |
| 479 | OH | CH$_3$ | 3-chloro-2-methylphenyl |
| 480 | OH | CF$_3$ | 3-chloro-2-methylphenyl |
| 481 | OH | F | 3-chloro-2-methylphenyl |
| 482 | OH | CN | 3-chloro-2-methylphenyl |
| 483 | OH | Cl | 3-chloro-2-methylphenyl |
| 484 | OH | C$_2$H$_5$ | 3-chloro-2-methylphenyl |
| 485 | phenyl | H | 4-chloro-2-methylphenyl |
| 486 | phenyl | CH$_3$ | 4-chloro-2-methylphenyl |
| 487 | H | CH$_3$ | 4-chloro-2-methylphenyl |
| 488 | CH$_3$ | H | 4-chloro-2-methylphenyl |
| 489 | OH | H | 4-chloro-2-methylphenyl |
| 490 | C(CH$_3$)$_3$ | H | 4-chloro-2-methylphenyl |
| 491 | CF$_3$ | H | 4-chloro-2-methylphenyl |
| 492 | CH(CH$_3$)$_2$ | H | 4-chloro-2-methylphenyl |
| 493 | 2-furyl | H | 4-chloro-2-methylphenyl |
| 494 | cyclohexyl | H | 4-chloro-2-methylphenyl |
| 495 | cyclobutyl | H | 4-chloro-2-methylphenyl |
| 496 | 4-methylphenyl | H | 4-chloro-2-methylphenyl |
| 497 | 2-methylphenyl | H | 4-chloro-2-methylphenyl |
| 498 | 2-fluorophenyl | H | 4-chloro-2-methylphenyl |
| 499 | 3-fluorophenyl | H | 4-chloro-2-methylphenyl |
| 500 | 4-fluorophenyl | H | 4-chloro-2-methylphenyl |
| 501 | OH | CH$_3$ | 4-chloro-2-methylphenyl |
| 502 | OH | CF$_3$ | 4-chloro-2-methylphenyl |
| 503 | OH | F | 4-chloro-2-methylphenyl |
| 504 | OH | CN | 4-chloro-2-methylphenyl |
| 505 | OH | Cl | 4-chloro-2-methylphenyl |
| 506 | OH | C$_2$H$_5$ | 4-chloro-2-methylphenyl |
| 507 | phenyl | H | 4-chloro-3-methylphenyl |
| 508 | phenyl | CH$_3$ | 4-chloro-3-methylphenyl |
| 509 | H | CH$_3$ | 4-chloro-3-methylphenyl |
| 510 | CH$_3$ | H | 4-chloro-3-methylphenyl |
| 511 | OH | H | 4-chloro-3-methylphenyl |
| 512 | C(CH$_3$)$_3$ | H | 4-chloro-3-methylphenyl |
| 513 | CF$_3$ | H | 4-chloro-3-methylphenyl |
| 514 | CH(CH$_3$)$_2$ | H | 4-chloro-3-methylphenyl |
| 515 | 2-furyl | H | 4-chloro-3-methylphenyl |
| 516 | cyclohexyl | H | 4-chloro-3-methylphenyl |
| 517 | cyclobutyl | H | 4-chloro-3-methylphenyl |
| 518 | 4-methylphenyl | H | 4-chloro-3-methylphenyl |
| 519 | 2-methylphenyl | H | 4-chloro-3-methylphenyl |
| 520 | 2-fluorophenyl | H | 4-chloro-3-methylphenyl |
| 521 | 3-fluorophenyl | H | 4-chloro-3-methylphenyl |
| 522 | 4-fluorophenyl | H | 4-chloro-3-methylphenyl |
| 523 | OH | CH$_3$ | 4-chloro-3-methylphenyl |
| 524 | OH | CF$_3$ | 4-chloro-3-methylphenyl |
| 525 | OH | F | 4-chloro-3-methylphenyl |
| 526 | OH | CN | 4-chloro-3-methylphenyl |
| 527 | OH | Cl | 4-chloro-3-methylphenyl |
| 528 | OH | C$_2$H$_5$ | 4-chloro-3-methylphenyl |
| 529 | phenyl | H | 2-chloro-4-methoxyphenyl |
| 530 | phenyl | CH$_3$ | 2-chloro-4-methoxyphenyl |
| 531 | H | CH$_3$ | 2-chloro-4-methoxyphenyl |
| 532 | CH$_3$ | H | 2-chloro-4-methoxyphenyl |
| 533 | OH | H | 2-chloro-4-methoxyphenyl |
| 534 | C(CH$_3$)$_3$ | H | 2-chloro-4-methoxyphenyl |
| 535 | CF$_3$ | H | 2-chloro-4-methoxyphenyl |

TABLE 1-continued

| | R¹ | R² | Q |
|---|---|---|---|
| 536 | CH(CH₃)₂ | H | 2-chloro-4-methoxyphenyl |
| 537 | 2-furyl | H | 2-chloro-4-methoxyphenyl |
| 538 | cyclohexyl | H | 2-chloro-4-methoxyphenyl |
| 539 | cyclobutyl | H | 2-chloro-4-methoxyphenyl |
| 540 | 4-methylphenyl | H | 2-chloro-4-methoxyphenyl |
| 541 | 2-methylphenyl | H | 2-chloro-4-methoxyphenyl |
| 542 | 2-fluorophenyl | H | 2-chloro-4-methoxyphenyl |
| 543 | 3-fluorophenyl | H | 2-chloro-4-methoxyphenyl |
| 544 | 4-fluorophenyl | H | 2-chloro-4-methoxyphenyl |
| 545 | OH | CH₃ | 2-chloro-4-methoxyphenyl |
| 546 | OH | CF₃ | 2-chloro-4-methoxyphenyl |
| 547 | OH | F | 2-chloro-4-methoxyphenyl |
| 548 | OH | CN | 2-chloro-4-methoxyphenyl |
| 549 | OH | Cl | 2-chloro-4-methoxyphenyl |
| 550 | OH | C₂H₅ | 2-chloro-4-methoxyphenyl |
| 551 | phenyl | H | 2-chloro-3-methoxyphenyl |
| 552 | phenyl | CH₃ | 2-chloro-3-methoxyphenyl |
| 553 | H | CH₃ | 2-chloro-3-methoxyphenyl |
| 554 | CH₃ | H | 2-chloro-3-methoxyphenyl |
| 555 | OH | H | 2-chloro-3-methoxyphenyl |
| 556 | C(CH₃)₃ | H | 2-chloro-3-methoxyphenyl |
| 557 | CF₃ | H | 2-chloro-3-methoxyphenyl |
| 558 | CH(CH₃)₂ | H | 2-chloro-3-methoxyphenyl |
| 559 | 2-furyl | H | 2-chloro-3-methoxyphenyl |
| 560 | cyclohexyl | H | 2-chloro-3-methoxyphenyl |
| 561 | cyclobutyl | H | 2-chloro-3-methoxyphenyl |
| 562 | 4-methylphenyl | H | 2-chloro-3-methoxyphenyl |
| 563 | 2-methylphenyl | H | 2-chloro-3-methoxyphenyl |
| 564 | 2-fluorophenyl | H | 2-chloro-3-methoxyphenyl |
| 565 | 3-fluorophenyl | H | 2-chloro-3-methoxyphenyl |
| 566 | 4-fluorophenyl | H | 2-chloro-3-methoxyphenyl |
| 567 | OH | CH₃ | 2-chloro-3-methoxyphenyl |
| 568 | OH | CF₃ | 2-chloro-3-methoxyphenyl |
| 569 | OH | F | 2-chloro-3-methoxyphenyl |
| 570 | OH | CN | 2-chloro-3-methoxyphenyl |
| 571 | OH | Cl | 2-chloro-3-methoxyphenyl |
| 572 | OH | C₂H₅ | 2-chloro-3-methoxyphenyl |
| 573 | phenyl | H | 3-chloro-4-methoxyphenyl |
| 574 | phenyl | CH₃ | 3-chloro-4-methoxyphenyl |
| 575 | H | CH₃ | 3-chloro-4-methoxyphenyl |
| 576 | CH₃ | H | 3-chloro-4-methoxyphenyl |
| 577 | OH | H | 3-chloro-4-methoxyphenyl |
| 578 | C(CH₃)₃ | H | 3-chloro-4-methoxyphenyl |
| 579 | CF₃ | H | 3-chloro-4-methoxyphenyl |
| 580 | CH(CH₃)₂ | H | 3-chloro-4-methoxyphenyl |
| 581 | 2-furyl | H | 3-chloro-4-methoxyphenyl |
| 582 | cyclohexyl | H | 3-chloro-4-methoxyphenyl |
| 583 | cyclobutyl | H | 3-chloro-4-methoxyphenyl |
| 584 | 4-methylphenyl | H | 3-chloro-4-methoxyphenyl |
| 585 | 2-methylphenyl | H | 3-chloro-4-methoxyphenyl |
| 586 | 2-fluorophenyl | H | 3-chloro-4-methoxyphenyl |
| 587 | 3-fluorophenyl | H | 3-chloro-4-methoxyphenyl |
| 588 | 4-fluorophenyl | H | 3-chloro-4-methoxyphenyl |
| 589 | OH | CH₃ | 3-chloro-4-methoxyphenyl |
| 590 | OH | CF₃ | 3-chloro-4-methoxyphenyl |
| 591 | OH | F | 3-chloro-4-methoxyphenyl |
| 592 | OH | CN | 3-chloro-4-methoxyphenyl |
| 593 | OH | Cl | 3-chloro-4-methoxyphenyl |
| 594 | OH | C₂H₅ | 3-chloro-4-methoxyphenyl |
| 595 | phenyl | H | 4-chloro-3-methoxyphenyl |
| 596 | phenyl | CH₃ | 4-chloro-3-methoxyphenyl |
| 597 | H | CH₃ | 4-chloro-3-methoxyphenyl |
| 598 | CH₃ | H | 4-chloro-3-methoxyphenyl |
| 599 | OH | H | 4-chloro-3-methoxyphenyl |
| 600 | C(CH₃)₃ | H | 4-chloro-3-methoxyphenyl |
| 601 | CF₃ | H | 4-chloro-3-methoxyphenyl |
| 602 | CH(CH₃)₂ | H | 4-chloro-3-methoxyphenyl |
| 603 | 2-furyl | H | 4-chloro-3-methoxyphenyl |
| 604 | cyclohexyl | H | 4-chloro-3-methoxyphenyl |
| 605 | cyclobutyl | H | 4-chloro-3-methoxyphenyl |
| 606 | 4-methylphenyl | H | 4-chloro-3-methoxyphenyl |
| 607 | 2-methylphenyl | H | 4-chloro-3-methoxyphenyl |
| 608 | 2-fluorophenyl | H | 4-chloro-3-methoxyphenyl |
| 609 | 3-fluorophenyl | H | 4-chloro-3-methoxyphenyl |
| 610 | 4-fluorophenyl | H | 4-chloro-3-methoxyphenyl |
| 611 | OH | CH₃ | 4-chloro-3-methoxyphenyl |
| 612 | OH | CF₃ | 4-chloro-3-methoxyphenyl |
| 613 | OH | F | 4-chloro-3-methoxyphenyl |
| 614 | OH | CN | 4-chloro-3-methoxyphenyl |
| 615 | OH | Cl | 4-chloro-3-methoxyphenyl |
| 616 | OH | C₂H₅ | 4-chloro-3-methoxyphenyl |
| 617 | phenyl | H | 4-chloro-2-methoxyphenyl |
| 618 | phenyl | CH₃ | 4-chloro-2-methoxyphenyl |
| 619 | H | CH₃ | 4-chloro-2-methoxyphenyl |
| 620 | CH₃ | H | 4-chloro-2-methoxyphenyl |
| 621 | OH | H | 4-chloro-2-methoxyphenyl |
| 622 | C(CH₃)₃ | H | 4-chloro-2-methoxyphenyl |
| 623 | CF₃ | H | 4-chloro-2-methoxyphenyl |
| 624 | CH(CH₃)₂ | H | 4-chloro-2-methoxyphenyl |
| 625 | 2-furyl | H | 4-chloro-2-methoxyphenyl |
| 626 | cyclohexyl | H | 4-chloro-2-methoxyphenyl |
| 627 | cyclobutyl | H | 4-chloro-2-methoxyphenyl |
| 628 | 4-methylphenyl | H | 4-chloro-2-methoxyphenyl |
| 629 | 2-methylphenyl | H | 4-chloro-2-methoxyphenyl |
| 630 | 2-fluorophenyl | H | 4-chloro-2-methoxyphenyl |
| 631 | 3-fluorophenyl | H | 4-chloro-2-methoxyphenyl |
| 632 | 4-fluorophenyl | H | 4-chloro-2-methoxyphenyl |
| 633 | OH | CH₃ | 4-chloro-2-methoxyphenyl |
| 634 | OH | CF₃ | 4-chloro-2-methoxyphenyl |
| 635 | OH | F | 4-chloro-2-methoxyphenyl |
| 636 | OH | CN | 4-chloro-2-methoxyphenyl |
| 637 | OH | Cl | 4-chloro-2-methoxyphenyl |
| 638 | OH | C₂H₅ | 4-chloro-2-methoxyphenyl |
| 639 | phenyl | H | 2,4,5-trimethoxyphenyl |
| 640 | phenyl | CH₃ | 2,4,5-trimethoxyphenyl |
| 641 | H | CH₃ | 2,4,5-trimethoxyphenyl |
| 642 | CH₃ | H | 2,4,5-trimethoxyphenyl |
| 643 | OH | H | 2,4,5-trimethoxyphenyl |
| 644 | C(CH₃)₃ | H | 2,4,5-trimethoxyphenyl |
| 645 | CF₃ | H | 2,4,5-trimethoxyphenyl |
| 646 | CH(CH₃)₂ | H | 2,4,5-trimethoxyphenyl |
| 647 | 2-furyl | H | 2,4,5-trimethoxyphenyl |
| 648 | cyclohexyl | H | 2,4,5-trimethoxyphenyl |
| 649 | cyclobutyl | H | 2,4,5-trimethoxyphenyl |
| 650 | 4-methylphenyl | H | 2,4,5-trimethoxyphenyl |
| 651 | 2-methylphenyl | H | 2,4,5-trimethoxyphenyl |
| 652 | 2-fluorophenyl | H | 2,4,5-trimethoxyphenyl |
| 653 | 3-fluorophenyl | H | 2,4,5-trimethoxyphenyl |
| 654 | 4-fluorophenyl | H | 2,4,5-trimethoxyphenyl |
| 655 | OH | CH₃ | 2,4,5-trimethoxyphenyl |
| 656 | OH | CF₃ | 2,4,5-trimethoxyphenyl |
| 657 | OH | F | 2,4,5-trimethoxyphenyl |
| 658 | OH | CN | 2,4,5-trimethoxyphenyl |
| 659 | OH | Cl | 2,4,5-trimethoxyphenyl |
| 660 | OH | C₂H₅ | 2,4,5-trimethoxyphenyl |
| 661 | phenyl | H | 2,3,4-trimethoxyphenyl |
| 662 | phenyl | CH₃ | 2,3,4-trimethoxyphenyl |
| 663 | H | CH₃ | 2,3,4-trimethoxyphenyl |
| 664 | CH₃ | H | 2,3,4-trimethoxyphenyl |
| 665 | OH | H | 2,3,4-trimethoxyphenyl |
| 666 | C(CH₃)₃ | H | 2,3,4-trimethoxyphenyl |
| 667 | CF₃ | H | 2,3,4-trimethoxyphenyl |
| 668 | CH(CH₃)₂ | H | 2,3,4-trimethoxyphenyl |
| 669 | 2-furyl | H | 2,3,4-trimethoxyphenyl |
| 670 | cyclohexyl | H | 2,3,4-trimethoxyphenyl |
| 671 | cyclobutyl | H | 2,3,4-trimethoxyphenyl |
| 672 | 4-methylphenyl | H | 2,3,4-trimethoxyphenyl |
| 673 | 2-methylphenyl | H | 2,3,4-trimethoxyphenyl |
| 674 | 2-fluorophenyl | H | 2,3,4-trimethoxyphenyl |
| 675 | 3-fluorophenyl | H | 2,3,4-trimethoxyphenyl |
| 676 | 4-fluorophenyl | H | 2,3,4-trimethoxyphenyl |
| 677 | OH | CH₃ | 2,3,4-trimethoxyphenyl |
| 678 | OH | CF₃ | 2,3,4-trimethoxyphenyl |
| 679 | OH | F | 2,3,4-trimethoxyphenyl |
| 680 | OH | CN | 2,3,4-trimethoxyphenyl |
| 681 | OH | Cl | 2,3,4-trimethoxyphenyl |
| 682 | OH | C₂H₅ | 2,3,4-trimethoxyphenyl |
| 683 | phenyl | H | 4-tert-butylphenyl |
| 684 | phenyl | CH₃ | 4-tert-butylphenyl |
| 685 | H | CH₃ | 4-tert-butylphenyl |
| 686 | CH₃ | H | 4-tert-butylphenyl |
| 687 | OH | H | 4-tert-butylphenyl |
| 688 | C(CH₃)₃ | H | 4-tert-butylphenyl |
| 689 | CF₃ | H | 4-tert-butylphenyl |
| 690 | CH(CH₃)₂ | H | 4-tert-butylphenyl |
| 691 | 2-furyl | H | 4-tert-butylphenyl |

TABLE 1-continued

| | R¹ | R² | Q |
|---|---|---|---|
| 692 | cyclohexyl | H | 4-tert-butylphenyl |
| 693 | cyclobutyl | H | 4-tert-butylphenyl |
| 694 | 4-methylphenyl | H | 4-tert-butylphenyl |
| 695 | 2-methylphenyl | H | 4-tert-butylphenyl |
| 696 | 2-fluorophenyl | H | 4-tert-butylphenyl |
| 697 | 3-fluorophenyl | H | 4-tert-butylphenyl |
| 698 | 4-fluorophenyl | H | 4-tert-butylphenyl |
| 699 | OH | $CH_3$ | 4-tert-butylphenyl |
| 700 | OH | $CF_3$ | 4-tert-butylphenyl |
| 701 | OH | F | 4-tert-butylphenyl |
| 702 | OH | CN | 4-tert-butylphenyl |
| 703 | OH | Cl | 4-tert-butylphenyl |
| 704 | OH | $C_2H_5$ | 4-tert-butylphenyl |
| 705 | phenyl | H | 4-methylphenyl |
| 706 | phenyl | $CH_3$ | 4-methylphenyl |
| 707 | H | $CH_3$ | 4-methylphenyl |
| 708 | $CH_3$ | H | 4-methylphenyl |
| 709 | OH | H | 4-methylphenyl |
| 710 | $C(CH_3)_3$ | H | 4-methylphenyl |
| 711 | $CF_3$ | H | 4-methylphenyl |
| 712 | $CH(CH_3)_2$ | H | 4-methylphenyl |
| 713 | 2-furyl | H | 4-methylphenyl |
| 714 | cyclohexyl | H | 4-methylphenyl |
| 715 | cyclobutyl | H | 4-methylphenyl |
| 716 | 4-methylphenyl | H | 4-methylphenyl |
| 717 | 2-methylphenyl | H | 4-methylphenyl |
| 718 | 2-fluorophenyl | H | 4-methylphenyl |
| 719 | 3-fluorophenyl | H | 4-methylphenyl |
| 720 | 4-fluorophenyl | H | 4-methylphenyl |
| 721 | OH | $CH_3$ | 4-methylphenyl |
| 722 | OH | $CF_3$ | 4-methylphenyl |
| 723 | OH | F | 4-methylphenyl |
| 724 | OH | CN | 4-methylphenyl |
| 725 | OH | Cl | 4-methylphenyl |
| 726 | OH | $C_2H_5$ | 4-methylphenyl |
| 727 | phenyl | H | 3-methoxyphenyl |
| 728 | phenyl | $CH_3$ | 3-methoxyphenyl |
| 729 | H | $CH_3$ | 3-methoxyphenyl |
| 730 | $CH_3$ | H | 3-methoxyphenyl |
| 731 | OH | H | 3-methoxyphenyl |
| 732 | $C(CH_3)_3$ | H | 3-methoxyphenyl |
| 733 | $CF_3$ | H | 3-methoxyphenyl |
| 734 | $CH(CH_3)_2$ | H | 3-methoxyphenyl |
| 735 | 2-furyl | H | 3-methoxyphenyl |
| 736 | cyclohexyl | H | 3-methoxyphenyl |
| 737 | cyclobutyl | H | 3-methoxyphenyl |
| 738 | 4-methylphenyl | H | 3-methoxyphenyl |
| 739 | 2-methylphenyl | H | 3-methoxyphenyl |
| 740 | 2-fluorophenyl | H | 3-methoxyphenyl |
| 741 | 3-fluorophenyl | H | 3-methoxyphenyl |
| 742 | 4-fluorophenyl | H | 3-methoxyphenyl |
| 743 | OH | $CH_3$ | 3-methoxyphenyl |
| 744 | OH | $CF_3$ | 3-methoxyphenyl |
| 745 | OH | F | 3-methoxyphenyl |
| 746 | OH | CN | 3-methoxyphenyl |
| 747 | OH | Cl | 3-methoxyphenyl |
| 748 | OH | $C_2H_5$ | 3-methoxyphenyl |
| 749 | phenyl | H | 4-methoxyphenyl |
| 750 | phenyl | $CH_3$ | 4-methoxyphenyl |
| 751 | H | $CH_3$ | 4-methoxyphenyl |
| 752 | $CH_3$ | H | 4-methoxyphenyl |
| 753 | OH | H | 4-methoxyphenyl |
| 754 | $C(CH_3)_3$ | H | 4-methoxyphenyl |
| 755 | $CF_3$ | H | 4-methoxyphenyl |
| 756 | $CH(CH_3)_2$ | H | 4-methoxyphenyl |
| 757 | 2-furyl | H | 4-methoxyphenyl |
| 758 | cyclohexyl | H | 4-methoxyphenyl |
| 759 | cyclobutyl | H | 4-methoxyphenyl |
| 760 | 4-methylphenyl | H | 4-methoxyphenyl |
| 761 | 2-methylphenyl | H | 4-methoxyphenyl |
| 762 | 2-fluorophenyl | H | 4-methoxyphenyl |
| 763 | 3-fluorophenyl | H | 4-methoxyphenyl |
| 764 | 4-fluorophenyl | H | 4-methoxyphenyl |
| 765 | OH | $CH_3$ | 4-methoxyphenyl |
| 766 | OH | $CF_3$ | 4-methoxyphenyl |
| 767 | OH | F | 4-methoxyphenyl |
| 768 | OH | CN | 4-methoxyphenyl |
| 769 | OH | Cl | 4-methoxyphenyl |
| 770 | OH | $C_2H_5$ | 4-methoxyphenyl |
| 771 | phenyl | H | 4-trifluoromethylphenyl |
| 772 | phenyl | $CH_3$ | 4-trifluoromethylphenyl |
| 773 | H | $CH_3$ | 4-trifluoromethylphenyl |
| 774 | $CH_3$ | H | 4-trifluoromethylphenyl |
| 775 | OH | H | 4-trifluoromethylphenyl |
| 776 | $C(CH_3)_3$ | H | 4-trifluoromethylphenyl |
| 777 | $CF_3$ | H | 4-trifluoromethylphenyl |
| 778 | $CH(CH_3)_2$ | H | 4-trifluoromethylphenyl |
| 779 | 2-furyl | H | 4-trifluoromethylphenyl |
| 780 | cyclohexyl | H | 4-trifluoromethylphenyl |
| 781 | cyclobutyl | H | 4-trifluoromethylphenyl |
| 782 | 4-methylphenyl | H | 4-trifluoromethylphenyl |
| 783 | 2-methylphenyl | H | 4-trifluoromethylphenyl |
| 784 | 2-fluorophenyl | H | 4-trifluoromethylphenyl |
| 785 | 3-fluorophenyl | H | 4-trifluoromethylphenyl |
| 786 | 4-fluorophenyl | H | 4-trifluoromethylphenyl |
| 787 | OH | $CH_3$ | 4-trifluoromethylphenyl |
| 788 | OH | $CF_3$ | 4-trifluoromethylphenyl |
| 789 | OH | F | 4-trifluoromethylphenyl |
| 790 | OH | CN | 4-trifluoromethylphenyl |
| 791 | OH | Cl | 4-trifluoromethylphenyl |
| 792 | OH | $C_2H_5$ | 4-trifluoromethylphenyl |
| 793 | phenyl | H | 2-chloro-4-trifluoromethylphenyl |
| 794 | phenyl | $CH_3$ | 2-chloro-4-trifluoromethylphenyl |
| 795 | H | $CH_3$ | 2-chloro-4-trifluoromethylphenyl |
| 796 | $CH_3$ | H | 2-chloro-4-trifluoromethylphenyl |
| 797 | OH | H | 2-chloro-4-trifluoromethylphenyl |
| 798 | $C(CH_3)_3$ | H | 2-chloro-4-trifluoromethylphenyl |
| 799 | $CF_3$ | H | 2-chloro-4-trifluoromethylphenyl |
| 800 | $CH(CH_3)_2$ | H | 2-chloro-4-trifluoromethylphenyl |
| 801 | 2-furyl | H | 2-chloro-4-trifluoromethylphenyl |
| 802 | cyclohexyl | H | 2-chloro-4-trifluoromethylphenyl |
| 803 | cyclobutyl | H | 2-chloro-4-trifluoromethylphenyl |
| 804 | 4-methylphenyl | H | 2-chloro-4-trifluoromethylphenyl |
| 805 | 2-methylphenyl | H | 2-chloro-4-trifluoromethylphenyl |
| 806 | 2-fluorophenyl | H | 2-chloro-4-trifluoromethylphenyl |
| 807 | 3-fluorophenyl | H | 2-chloro-4-trifluoromethylphenyl |
| 808 | 4-fluorophenyl | H | 2-chloro-4-trifluoromethylphenyl |
| 809 | OH | $CH_3$ | 2-chloro-4-trifluoromethylphenyl |
| 810 | OH | $CF_3$ | 2-chloro-4-trifluoromethylphenyl |
| 811 | OH | F | 2-chloro-4-trifluoromethylphenyl |
| 812 | OH | CN | 2-chloro-4-trifluoromethylphenyl |
| 813 | OH | Cl | 2-chloro-4-trifluoromethylphenyl |
| 814 | OH | $C_2H_5$ | 2-chloro-4-trifluoromethylphenyl |
| 815 | phenyl | H | 3-chloro-4-trifluoromethylphenyl |
| 816 | phenyl | $CH_3$ | 3-chloro-4-trifluoromethylphenyl |
| 817 | H | $CH_3$ | 3-chloro-4-trifluoromethylphenyl |
| 818 | $CH_3$ | H | 3-chloro-4-trifluoromethylphenyl |
| 819 | OH | H | 3-chloro-4-trifluoromethylphenyl |
| 820 | $C(CH_3)_3$ | H | 3-chloro-4-trifluoromethylphenyl |
| 821 | $CF_3$ | H | 3-chloro-4-trifluoromethylphenyl |
| 822 | $CH(CH_3)_2$ | H | 3-chloro-4-trifluoromethylphenyl |
| 823 | 2-furyl | H | 3-chloro-4-trifluoromethylphenyl |
| 824 | cyclohexyl | H | 3-chloro-4-trifluoromethylphenyl |
| 825 | cyclobutyl | H | 3-chloro-4-trifluoromethylphenyl |
| 826 | 4-methylphenyl | H | 3-chloro-4-trifluoromethylphenyl |
| 827 | 2-methylphenyl | H | 3-chloro-4-trifluoromethylphenyl |
| 828 | 2-fluorophenyl | H | 3-chloro-4-trifluoromethylphenyl |
| 829 | 3-fluorophenyl | H | 3-chloro-4-trifluoromethylphenyl |
| 830 | 4-fluorophenyl | H | 3-chloro-4-trifluoromethylphenyl |
| 831 | OH | $CH_3$ | 3-chloro-4-trifluoromethylphenyl |
| 832 | OH | $CF_3$ | 3-chloro-4-trifluoromethylphenyl |
| 833 | OH | F | 3-chloro-4-trifluoromethylphenyl |
| 834 | OH | CN | 3-chloro-4-trifluoromethylphenyl |
| 835 | OH | Cl | 3-chloro-4-trifluoromethylphenyl |
| 836 | OH | $C_2H_5$ | 3-chloro-4-trifluoromethylphenyl |
| 837 | phenyl | H | 2-trifluoromethylphenyl |
| 838 | phenyl | $CH_3$ | 2-trifluoromethylphenyl |
| 839 | H | $CH_3$ | 2-trifluoromethylphenyl |
| 840 | $CH_3$ | H | 2-trifluoromethylphenyl |
| 841 | OH | H | 2-trifluoromethylphenyl |
| 842 | $C(CH_3)_3$ | H | 2-trifluoromethylphenyl |
| 843 | $CF_3$ | H | 2-trifluoromethylphenyl |
| 844 | $CH(CH_3)_2$ | H | 2-trifluoromethylphenyl |
| 845 | 2-furyl | H | 2-trifluoromethylphenyl |
| 846 | cyclohexyl | H | 2-trifluoromethylphenyl |
| 847 | cyclobutyl | H | 2-trifluoromethylphenyl |

TABLE 1-continued

| | R¹ | R² | Q |
|---|---|---|---|
| 848 | 4-methylphenyl | H | 2-trifluoromethylphenyl |
| 849 | 2-methylphenyl | H | 2-trifluoromethylphenyl |
| 850 | 2-fluorophenyl | H | 2-trifluoromethylphenyl |
| 851 | 3-fluorophenyl | H | 2-trifluoromethylphenyl |
| 852 | 4-fluorophenyl | H | 2-trifluoromethylphenyl |
| 853 | OH | CH₃ | 2-trifluoromethylphenyl |
| 854 | OH | CF₃ | 2-trifluoromethylphenyl |
| 855 | OH | F | 2-trifluoromethylphenyl |
| 856 | OH | CN | 2-trifluoromethylphenyl |
| 857 | OH | Cl | 2-trifluoromethylphenyl |
| 858 | OH | C₂H₅ | 2-trifluoromethylphenyl |
| 859 | phenyl | H | 4-trifluoromethoxyphenyl |
| 860 | phenyl | CH₃ | 4-trifluoromethoxyphenyl |
| 861 | H | CH₃ | 4-trifluoromethoxyphenyl |
| 862 | CH₃ | H | 4-trifluoromethoxyphenyl |
| 863 | OH | H | 4-trifluoromethoxyphenyl |
| 864 | C(CH₃)₃ | H | 4-trifluoromethoxyphenyl |
| 865 | CF₃ | H | 4-trifluoromethoxyphenyl |
| 866 | CH(CH₃)₂ | H | 4-trifluoromethoxyphenyl |
| 867 | 2-furyl | H | 4-trifluoromethoxyphenyl |
| 868 | cyclohexyl | H | 4-trifluoromethoxyphenyl |
| 869 | cyclobutyl | H | 4-trifluoromethoxyphenyl |
| 870 | 4-methylphenyl | H | 4-trifluoromethoxyphenyl |
| 871 | 2-methylphenyl | H | 4-trifluoromethoxyphenyl |
| 872 | 2-fluorophenyl | H | 4-trifluoromethoxyphenyl |
| 873 | 3-fluorophenyl | H | 4-trifluoromethoxyphenyl |
| 874 | 4-fluorophenyl | H | 4-trifluoromethoxyphenyl |
| 875 | OH | CH₃ | 4-trifluoromethoxyphenyl |
| 876 | OH | CF₃ | 4-trifluoromethoxyphenyl |
| 877 | OH | F | 4-trifluoromethoxyphenyl |
| 878 | OH | CN | 4-trifluoromethoxyphenyl |
| 879 | OH | Cl | 4-trifluoromethoxyphenyl |
| 880 | OH | C₂H₅ | 4-trifluoromethoxyphenyl |
| 881 | phenyl | H | 4-isopropylphenyl |
| 882 | phenyl | CH₃ | 4-isopropylphenyl |
| 883 | H | CH₃ | 4-isopropylphenyl |
| 884 | CH₃ | H | 4-isopropylphenyl |
| 885 | OH | H | 4-isopropylphenyl |
| 886 | C(CH₃)₃ | H | 4-isopropylphenyl |
| 887 | CF₃ | H | 4-isopropylphenyl |
| 888 | CH(CH₃)₂ | H | 4-isopropylphenyl |
| 889 | 2-furyl | H | 4-isopropylphenyl |
| 890 | cyclohexyl | H | 4-isopropylphenyl |
| 891 | cyclobutyl | H | 4-isopropylphenyl |
| 892 | 4-methylphenyl | H | 4-isopropylphenyl |
| 893 | 2-methylphenyl | H | 4-isopropylphenyl |
| 894 | 2-fluorophenyl | H | 4-isopropylphenyl |
| 895 | 3-fluorophenyl | H | 4-isopropylphenyl |
| 896 | 4-fluorophenyl | H | 4-isopropylphenyl |
| 897 | OH | CH₃ | 4-isopropylphenyl |
| 898 | OH | CF₃ | 4-isopropylphenyl |
| 899 | OH | F | 4-isopropylphenyl |
| 900 | OH | CN | 4-isopropylphenyl |
| 901 | OH | Cl | 4-isopropylphenyl |
| 902 | OH | C₂H₅ | 4-isopropylphenyl |
| 903 | phenyl | H | 4-cyclopropylphenyl |
| 904 | phenyl | CH₃ | 4-cyclopropylphenyl |
| 905 | H | CH₃ | 4-cyclopropylphenyl |
| 906 | CH₃ | H | 4-cyclopropylphenyl |
| 907 | OH | H | 4-cyclopropylphenyl |
| 908 | C(CH₃)₃ | H | 4-cyclopropylphenyl |
| 909 | CF₃ | H | 4-cyclopropylphenyl |
| 910 | CH(CH₃)₂ | H | 4-cyclopropylphenyl |
| 911 | 2-furyl | H | 4-cyclopropylphenyl |
| 912 | cyclohexyl | H | 4-cyclopropylphenyl |
| 913 | cyclobutyl | H | 4-cyclopropylphenyl |
| 914 | 4-methylphenyl | H | 4-cyclopropylphenyl |
| 915 | 2-methylphenyl | H | 4-cyclopropylphenyl |
| 916 | 2-fluorophenyl | H | 4-cyclopropylphenyl |
| 917 | 3-fluorophenyl | H | 4-cyclopropylphenyl |
| 918 | 4-fluorophenyl | H | 4-cyclopropylphenyl |
| 919 | OH | CH₃ | 4-cyclopropylphenyl |
| 920 | OH | CF₃ | 4-cyclopropylphenyl |
| 921 | OH | F | 4-cyclopropylphenyl |
| 922 | OH | CN | 4-cyclopropylphenyl |
| 923 | OH | Cl | 4-cyclopropylphenyl |
| 924 | OH | C₂H₅ | 4-cyclopropylphenyl |
| 925 | phenyl | H | 4-dimethylaminophenyl |
| 926 | phenyl | CH₃ | 4-dimethylaminophenyl |
| 927 | H | CH₃ | 4-dimethylaminophenyl |
| 928 | CH₃ | H | 4-dimethylaminophenyl |
| 929 | OH | H | 4-dimethylaminophenyl |
| 930 | C(CH₃)₃ | H | 4-dimethylaminophenyl |
| 931 | CF₃ | H | 4-dimethylaminophenyl |
| 932 | CH(CH₃)₂ | H | 4-dimethylaminophenyl |
| 933 | 2-furyl | H | 4-dimethylaminophenyl |
| 934 | cyclohexyl | H | 4-dimethylaminophenyl |
| 935 | cyclobutyl | H | 4-dimethylaminophenyl |
| 936 | 4-methylphenyl | H | 4-dimethylaminophenyl |
| 937 | 2-methylphenyl | H | 4-dimethylaminophenyl |
| 938 | 2-fluorophenyl | H | 4-dimethylaminophenyl |
| 939 | 3-fluorophenyl | H | 4-dimethylaminophenyl |
| 940 | 4-fluorophenyl | H | 4-dimethylaminophenyl |
| 941 | OH | CH₃ | 4-dimethylaminophenyl |
| 942 | OH | CF₃ | 4-dimethylaminophenyl |
| 943 | OH | F | 4-dimethylaminophenyl |
| 944 | OH | CN | 4-dimethylaminophenyl |
| 945 | OH | Cl | 4-dimethylaminophenyl |
| 946 | OH | C₂H₅ | 4-dimethylaminophenyl |
| 947 | phenyl | H | 2-pyridinyl |
| 948 | phenyl | CH₃ | 2-pyridinyl |
| 949 | H | CH₃ | 2-pyridinyl |
| 950 | CH₃ | H | 2-pyridinyl |
| 951 | OH | H | 2-pyridinyl |
| 952 | C(CH₃)₃ | H | 2-pyridinyl |
| 953 | CF₃ | H | 2-pyridinyl |
| 954 | CH(CH₃)₂ | H | 2-pyridinyl |
| 955 | 2-furyl | H | 2-pyridinyl |
| 956 | cyclohexyl | H | 2-pyridinyl |
| 957 | cyclobutyl | H | 2-pyridinyl |
| 958 | 4-methylphenyl | H | 2-pyridinyl |
| 959 | 2-methylphenyl | H | 2-pyridinyl |
| 960 | 2-fluorophenyl | H | 2-pyridinyl |
| 961 | 3-fluorophenyl | H | 2-pyridinyl |
| 962 | 4-fluorophenyl | H | 2-pyridinyl |
| 963 | OH | CH₃ | 2-pyridinyl |
| 964 | OH | CF₃ | 2-pyridinyl |
| 965 | OH | F | 2-pyridinyl |
| 966 | OH | CN | 2-pyridinyl |
| 967 | OH | Cl | 2-pyridinyl |
| 968 | OH | C₂H₅ | 2-pyridinyl |
| 969 | phenyl | H | 3-pyridinyl |
| 970 | phenyl | CH₃ | 3-pyridinyl |
| 971 | H | CH₃ | 3-pyridinyl |
| 972 | CH₃ | H | 3-pyridinyl |
| 973 | OH | H | 3-pyridinyl |
| 974 | C(CH₃)₃ | H | 3-pyridinyl |
| 975 | CF₃ | H | 3-pyridinyl |
| 976 | CH(CH₃)₂ | H | 3-pyridinyl |
| 977 | 2-furyl | H | 3-pyridinyl |
| 978 | cyclohexyl | H | 3-pyridinyl |
| 979 | cyclobutyl | H | 3-pyridinyl |
| 980 | 4-methylphenyl | H | 3-pyridinyl |
| 981 | 2-methylphenyl | H | 3-pyridinyl |
| 982 | 2-fluorophenyl | H | 3-pyridinyl |
| 983 | 3-fluorophenyl | H | 3-pyridinyl |
| 984 | 4-fluorophenyl | H | 3-pyridinyl |
| 985 | OH | CH₃ | 3-pyridinyl |
| 986 | OH | CF₃ | 3-pyridinyl |
| 987 | OH | F | 3-pyridinyl |
| 988 | OH | CN | 3-pyridinyl |
| 989 | OH | Cl | 3-pyridinyl |
| 990 | OH | C₂H₅ | 3-pyridinyl |
| 991 | phenyl | H | 4-pyridinyl |
| 992 | phenyl | CH₃ | 4-pyridinyl |
| 993 | H | CH₃ | 4-pyridinyl |
| 994 | CH₃ | H | 4-pyridinyl |
| 995 | OH | H | 4-pyridinyl |
| 996 | C(CH₃)₃ | H | 4-pyridinyl |
| 997 | CF₃ | H | 4-pyridinyl |
| 998 | CH(CH₃)₂ | H | 4-pyridinyl |
| 999 | 2-furyl | H | 4-pyridinyl |
| 1000 | cyclohexyl | H | 4-pyridinyl |
| 1001 | cyclobutyl | H | 4-pyridinyl |
| 1002 | 4-methylphenyl | H | 4-pyridinyl |
| 1003 | 2-methylphenyl | H | 4-pyridinyl |

TABLE 1-continued

| | R¹ | R² | Q |
|---|---|---|---|
| 1004 | 2-fluorophenyl | H | 4-pyridinyl |
| 1005 | 3-fluorophenyl | H | 4-pyridinyl |
| 1006 | 4-fluorophenyl | H | 4-pyridinyl |
| 1007 | OH | $CH_3$ | 4-pyridinyl |
| 1008 | OH | $CF_3$ | 4-pyridinyl |
| 1009 | OH | F | 4-pyridinyl |
| 1010 | OH | CN | 4-pyridinyl |
| 1011 | OH | Cl | 4-pyridinyl |
| 1012 | OH | $C_2H_5$ | 4-pyridinyl |
| 1013 | phenyl | H | 4,6-dimethoxypyrimidin-2-yl |
| 1014 | phenyl | $CH_3$ | 4,6-dimethoxypyrimidin-2-yl |
| 1015 | H | $CH_3$ | 4,6-dimethoxypyrimidin-2-yl |
| 1016 | $CH_3$ | H | 4,6-dimethoxypyrimidin-2-yl |
| 1017 | OH | H | 4,6-dimethoxypyrimidin-2-yl |
| 1018 | $C(CH_3)_3$ | H | 4,6-dimethoxypyrimidin-2-yl |
| 1019 | $CF_3$ | H | 4,6-dimethoxypyrimidin-2-yl |
| 1020 | $CH(CH_3)_2$ | H | 4,6-dimethoxypyrimidin-2-yl |
| 1021 | 2-furyl | H | 4,6-dimethoxypyrimidin-2-yl |
| 1022 | cyclohexyl | H | 4,6-dimethoxypyrimidin-2-yl |
| 1023 | cyclobutyl | H | 4,6-dimethoxypyrimidin-2-yl |
| 1024 | 4-methylphenyl | H | 4,6-dimethoxypyrimidin-2-yl |
| 1025 | 2-methylphenyl | H | 4,6-dimethoxypyrimidin-2-yl |
| 1026 | 2-fluorophenyl | H | 4,6-dimethoxypyrimidin-2-yl |
| 1027 | 3-fluorophenyl | H | 4,6-dimethoxypyrimidin-2-yl |
| 1028 | 4-fluorophenyl | H | 4,6-dimethoxypyrimidin-2-yl |
| 1029 | OH | $CH_3$ | 4,6-dimethoxypyrimidin-2-yl |
| 1030 | OH | $CF_3$ | 4,6-dimethoxypyrimidin-2-yl |
| 1031 | OH | F | 4,6-dimethoxypyrimidin-2-yl |
| 1032 | OH | CN | 4,6-dimethoxypyrimidin-2-yl |
| 1033 | OH | Cl | 4,6-dimethoxypyrimidin-2-yl |
| 1034 | OH | $C_2H_5$ | 4,6-dimethoxypyrimidin-2-yl |
| 1035 | phenyl | H | 2-thienyl |
| 1036 | phenyl | $CH_3$ | 2-thienyl |
| 1037 | H | $CH_3$ | 2-thienyl |
| 1038 | $CH_3$ | H | 2-thienyl |
| 1039 | OH | H | 2-thienyl |
| 1040 | $C(CH_3)_3$ | H | 2-thienyl |
| 1041 | $CF_3$ | H | 2-thienyl |
| 1042 | $CH(CH_3)_2$ | H | 2-thienyl |
| 1043 | 2-furyl | H | 2-thienyl |
| 1044 | cyclohexyl | H | 2-thienyl |
| 1045 | cyclobutyl | H | 2-thienyl |
| 1046 | 4-methylphenyl | H | 2-thienyl |
| 1047 | 2-methylphenyl | H | 2-thienyl |
| 1048 | 2-fluorophenyl | H | 2-thienyl |
| 1049 | 3-fluorophenyl | H | 2-thienyl |
| 1050 | 4-fluorophenyl | H | 2-thienyl |
| 1051 | OH | $CH_3$ | 2-thienyl |
| 1052 | OH | $CF_3$ | 2-thienyl |
| 1053 | OH | F | 2-thienyl |
| 1054 | OH | CN | 2-thienyl |
| 1055 | OH | Cl | 2-thienyl |
| 1056 | OH | $C_2H_5$ | 2-thienyl |
| 1057 | phenyl | H | 2-furyl |
| 1058 | phenyl | $CH_3$ | 2-furyl |
| 1059 | H | $CH_3$ | 2-furyl |
| 1060 | $CH_3$ | H | 2-furyl |
| 1061 | OH | H | 2-furyl |
| 1062 | $C(CH_3)_3$ | H | 2-furyl |
| 1063 | $CF_3$ | H | 2-furyl |
| 1064 | $CH(CH_3)_2$ | H | 2-furyl |
| 1065 | 2-furyl | H | 2-furyl |
| 1066 | cyclohexyl | H | 2-furyl |
| 1067 | cyclobutyl | H | 2-furyl |
| 1068 | 4-methylphenyl | H | 2-furyl |
| 1069 | 2-methylphenyl | H | 2-furyl |
| 1070 | 2-fluorophenyl | H | 2-furyl |
| 1071 | 3-fluorophenyl | H | 2-furyl |
| 1072 | 4-fluorophenyl | H | 2-furyl |
| 1073 | OH | $CH_3$ | 2-furyl |
| 1074 | OH | $CF_3$ | 2-furyl |
| 1075 | OH | F | 2-furyl |
| 1076 | OH | CN | 2-furyl |
| 1077 | OH | Cl | 2-furyl |
| 1078 | OH | $C_2H_5$ | 2-furyl |
| 1079 | phenyl | H | benzimidazol-2-yl |
| 1080 | phenyl | $CH_3$ | benzimidazol-2-yl |
| 1081 | H | $CH_3$ | benzimidazol-2-yl |
| 1082 | $CH_3$ | H | benzimidazol-2-yl |
| 1083 | OH | H | benzimidazol-2-yl |
| 1084 | $C(CH_3)_3$ | H | benzimidazol-2-yl |
| 1085 | $CF_3$ | H | benzimidazol-2-yl |
| 1086 | $CH(CH_3)_2$ | H | benzimidazol-2-yl |
| 1087 | 2-furyl | H | benzimidazol-2-yl |
| 1088 | cyclohexyl | H | benzimidazol-2-yl |
| 1089 | cyclobutyl | H | benzimidazol-2-yl |
| 1090 | 4-methylphenyl | H | benzimidazol-2-yl |
| 1091 | 2-methylphenyl | H | benzimidazol-2-yl |
| 1092 | 2-fluorophenyl | H | benzimidazol-2-yl |
| 1093 | 3-fluorophenyl | H | benzimidazol-2-yl |
| 1094 | 4-fluorophenyl | H | benzimidazol-2-yl |
| 1095 | OH | $CH_3$ | benzimidazol-2-yl |
| 1096 | OH | $CF_3$ | benzimidazol-2-yl |
| 1097 | OH | F | benzimidazol-2-yl |
| 1098 | OH | CN | benzimidazol-2-yl |
| 1099 | OH | Cl | benzimidazol-2-yl |
| 1100 | OH | $C_2H_5$ | benzimidazol-2-yl |
| 1101 | phenyl | H | benzoxazol-2-yl |
| 1102 | phenyl | $CH_3$ | benzoxazol-2-yl |
| 1103 | H | $CH_3$ | benzoxazol-2-yl |
| 1104 | $CH_3$ | H | benzoxazol-2-yl |
| 1105 | OH | H | benzoxazol-2-yl |
| 1106 | $C(CH_3)_3$ | H | benzoxazol-2-yl |
| 1107 | $CF_3$ | H | benzoxazol-2-yl |
| 1108 | $CH(CH_3)_2$ | H | benzoxazol-2-yl |
| 1109 | 2-furyl | H | benzoxazol-2-yl |
| 1110 | cyclohexyl | H | benzoxazol-2-yl |
| 1111 | cyclobutyl | H | benzoxazol-2-yl |
| 1112 | 4-methylphenyl | H | benzoxazol-2-yl |
| 1113 | 2-methylphenyl | H | benzoxazol-2-yl |
| 1114 | 2-fluorophenyl | H | benzoxazol-2-yl |
| 1115 | 3-fluorophenyl | H | benzoxazol-2-yl |
| 1116 | 4-fluorophenyl | H | benzoxazol-2-yl |
| 1117 | OH | $CH_3$ | benzoxazol-2-yl |
| 1118 | OH | $CF_3$ | benzoxazol-2-yl |
| 1119 | OH | F | benzoxazol-2-yl |
| 1120 | OH | CN | benzoxazol-2-yl |
| 1121 | OH | Cl | benzoxazol-2-yl |
| 1122 | OH | $C_2H_5$ | benzoxazol-2-yl |
| 1123 | phenyl | H | benzothiazol-2-yl |
| 1124 | phenyl | $CH_3$ | benzothiazol-2-yl |
| 1125 | H | $CH_3$ | benzothiazol-2-yl |
| 1126 | $CH_3$ | H | benzothiazol-2-yl |
| 1127 | OH | H | benzothiazol-2-yl |
| 1128 | $C(CH_3)_3$ | H | benzothiazol-2-yl |
| 1129 | $CF_3$ | H | benzothiazol-2-yl |
| 1130 | $CH(CH_3)_2$ | H | benzothiazol-2-yl |
| 1131 | 2-furyl | H | benzothiazol-2-yl |
| 1132 | cyclohexyl | H | benzothiazol-2-yl |
| 1133 | cyclobutyl | H | benzothiazol-2-yl |
| 1134 | 4-methylphenyl | H | benzothiazol-2-yl |
| 1135 | 2-methylphenyl | H | benzothiazol-2-yl |
| 1136 | 2-fluorophenyl | H | benzothiazol-2-yl |
| 1137 | 3-fluorophenyl | H | benzothiazol-2-yl |
| 1138 | 4-fluorophenyl | H | benzothiazol-2-yl |
| 1139 | OH | $CH_3$ | benzothiazol-2-yl |
| 1140 | OH | $CF_3$ | benzothiazol-2-yl |
| 1141 | OH | F | benzothiazol-2-yl |
| 1142 | OH | CN | benzothiazol-2-yl |
| 1143 | OH | Cl | benzothiazol-2-yl |
| 1144 | OH | $C_2H_5$ | benzothiazol-2-yl |
| 1145 | phenyl | H | 2-chlorothiazol-5-yl |
| 1146 | phenyl | $CH_3$ | 2-chlorothiazol-5-yl |
| 1147 | H | $CH_3$ | 2-chlorothiazol-5-yl |
| 1148 | $CH_3$ | H | 2-chlorothiazol-5-yl |
| 1149 | OH | H | 2-chlorothiazol-5-yl |
| 1150 | $C(CH_3)_3$ | H | 2-chlorothiazol-5-yl |
| 1151 | $CF_3$ | H | 2-chlorothiazol-5-yl |
| 1152 | $CH(CH_3)_2$ | H | 2-chlorothiazol-5-yl |
| 1153 | 2-furyl | H | 2-chlorothiazol-5-yl |
| 1154 | cyclohexyl | H | 2-chlorothiazol-5-yl |
| 1155 | cyclobutyl | H | 2-chlorothiazol-5-yl |
| 1156 | 4-methylphenyl | H | 2-chlorothiazol-5-yl |
| 1157 | 2-methylphenyl | H | 2-chlorothiazol-5-yl |
| 1158 | 2-fluorophenyl | H | 2-chlorothiazol-5-yl |
| 1159 | 3-fluorophenyl | H | 2-chlorothiazol-5-yl |

TABLE 1-continued

| | R¹ | R² | Q |
|---|---|---|---|
| 1160 | 4-fluorophenyl | H | 2-chlorothiazol-5-yl |
| 1161 | OH | CH₃ | 2-chlorothiazol-5-yl |
| 1162 | OH | CF₃ | 2-chlorothiazol-5-yl |
| 1163 | OH | F | 2-chlorothiazol-5-yl |
| 1164 | OH | CN | 2-chlorothiazol-5-yl |
| 1165 | OH | Cl | 2-chlorothiazol-5-yl |
| 1166 | OH | C₂H₅ | 2-chlorothiazol-5-yl |
| 1167 | phenyl | H | 6-chloropyridin-2-yl |
| 1168 | phenyl | CH₃ | 6-chloropyridin-2-yl |
| 1169 | H | CH₃ | 6-chloropyridin-2-yl |
| 1170 | CH₃ | H | 6-chloropyridin-2-yl |
| 1171 | OH | H | 6-chloropyridin-2-yl |
| 1172 | C(CH₃)₃ | H | 6-chloropyridin-2-yl |
| 1173 | CF₃ | H | 6-chloropyridin-2-yl |
| 1174 | CH(CH₃)₂ | H | 6-chloropyridin-2-yl |
| 1175 | 2-furyl | H | 6-chloropyridin-2-yl |
| 1176 | cyclohexyl | H | 6-chloropyridin-2-yl |
| 1177 | cyclobutyl | H | 6-chloropyridin-2-yl |
| 1178 | 4-methylphenyl | H | 6-chloropyridin-2-yl |
| 1179 | 2-methylphenyl | H | 6-chloropyridin-2-yl |
| 1180 | 2-fluorophenyl | H | 6-chloropyridin-2-yl |
| 1181 | 3-fluorophenyl | H | 6-chloropyridin-2-yl |
| 1182 | 4-fluorophenyl | H | 6-chloropyridin-2-yl |
| 1183 | OH | CH₃ | 6-chloropyridin-2-yl |
| 1184 | OH | CF₃ | 6-chloropyridin-2-yl |
| 1185 | OH | F | 6-chloropyridin-2-yl |
| 1186 | OH | CN | 6-chloropyridin-2-yl |
| 1187 | OH | Cl | 6-chloropyridin-2-yl |
| 1188 | OH | C₂H₅ | 6-chloropyridin-2-yl |
| 1189 | phenyl | H | 1-methylimidazol-2-yl |
| 1190 | phenyl | CH₃ | 1-methylimidazol-2-yl |
| 1191 | H | CH₃ | 1-methylimidazol-2-yl |
| 1192 | CH₃ | H | 1-methylimidazol-2-yl |
| 1193 | OH | H | 1-methylimidazol-2-yl |
| 1194 | C(CH₃)₃ | H | 1-methylimidazol-2-yl |
| 1195 | CF₃ | H | 1-methylimidazol-2-yl |
| 1196 | CH(CH₃)₂ | H | 1-methylimidazol-2-yl |
| 1197 | 2-furyl | H | 1-methylimidazol-2-yl |
| 1198 | cyclohexyl | H | 1-methylimidazol-2-yl |
| 1199 | cyclobutyl | H | 1-methylimidazol-2-yl |
| 1200 | 4-methylphenyl | H | 1-methylimidazol-2-yl |
| 1201 | 2-methylphenyl | H | 1-methylimidazol-2-yl |
| 1202 | 2-fluorophenyl | H | 1-methylimidazol-2-yl |
| 1203 | 3-fluorophenyl | H | 1-methylimidazol-2-yl |
| 1204 | 4-fluorophenyl | H | 1-methylimidazol-2-yl |
| 1205 | OH | CH₃ | 1-methylimidazol-2-yl |
| 1206 | OH | CF₃ | 1-methylimidazol-2-yl |
| 1207 | OH | F | 1-methylimidazol-2-yl |
| 1208 | OH | CN | 1-methylimidazol-2-yl |
| 1209 | OH | Cl | 1-methylimidazol-2-yl |
| 1210 | OH | C₂H₅ | 1-methylimidazol-2-yl |
| 1211 | phenyl | H | 2-methylthiazol-5-yl |
| 1212 | phenyl | CH₃ | 2-methylthiazol-5-yl |
| 1213 | H | CH₃ | 2-methylthiazol-5-yl |
| 1214 | CH₃ | H | 2-methylthiazol-5-yl |
| 1215 | OH | H | 2-methylthiazol-5-yl |
| 1216 | C(CH₃)₃ | H | 2-methylthiazol-5-yl |
| 1217 | CF₃ | H | 2-methylthiazol-5-yl |
| 1218 | CH(CH₃)₂ | H | 2-methylthiazol-5-yl |
| 1219 | 2-furyl | H | 2-methylthiazol-5-yl |
| 1220 | cyclohexyl | H | 2-methylthiazol-5-yl |
| 1221 | cyclobutyl | H | 2-methylthiazol-5-yl |
| 1222 | 4-methylphenyl | H | 2-methylthiazol-5-yl |
| 1223 | 2-methylphenyl | H | 2-methylthiazol-5-yl |
| 1224 | 2-fluorophenyl | H | 2-methylthiazol-5-yl |
| 1225 | 3-fluorophenyl | H | 2-methylthiazol-5-yl |
| 1226 | 4-fluorophenyl | H | 2-methylthiazol-5-yl |
| 1227 | OH | CH₃ | 2-methylthiazol-5-yl |
| 1228 | OH | CF₃ | 2-methylthiazol-5-yl |
| 1229 | OH | F | 2-methylthiazol-5-yl |
| 1230 | OH | CN | 2-methylthiazol-5-yl |
| 1231 | OH | Cl | 2-methylthiazol-5-yl |
| 1232 | OH | C₂H₅ | 2-methylthiazol-5-yl |
| 1233 | phenyl | H | 2-methyl-α-naphthyl |
| 1234 | phenyl | CH₃ | 2-methyl-α-naphthyl |
| 1235 | H | CH₃ | 2-methyl-α-naphthyl |
| 1236 | CH₃ | H | 2-methyl-α-naphthyl |
| 1237 | OH | H | 2-methyl-α-naphthyl |
| 1238 | C(CH₃)₃ | H | 2-methyl-α-naphthyl |
| 1239 | CF₃ | H | 2-methyl-α-naphthyl |
| 1240 | CH(CH₃)₂ | H | 2-methyl-α-naphthyl |
| 1241 | 2-furyl | H | 2-methyl-α-naphthyl |
| 1242 | cyclohexyl | H | 2-methyl-α-naphthyl |
| 1243 | cyclobutyl | H | 2-methyl-α-naphthyl |
| 1244 | 4-methylphenyl | H | 2-methyl-α-naphthyl |
| 1245 | 2-methylphenyl | H | 2-methyl-α-naphthyl |
| 1246 | 2-fluorophenyl | H | 2-methyl-α-naphthyl |
| 1247 | 3-fluorophenyl | H | 2-methyl-α-naphthyl |
| 1248 | 4-fluorophenyl | H | 2-methyl-α-naphthyl |
| 1249 | OH | CH₃ | 2-methyl-α-naphthyl |
| 1250 | OH | CF₃ | 2-methyl-α-naphthyl |
| 1251 | OH | F | 2-methyl-α-naphthyl |
| 1252 | OH | CN | 2-methyl-α-naphthyl |
| 1253 | OH | Cl | 2-methyl-α-naphthyl |
| 1254 | OH | C₂H₅ | 2-methyl-α-naphthyl |
| 1255 | phenyl | H | α-naphthyl |
| 1256 | phenyl | CH₃ | α-naphthyl |
| 1257 | H | CH₃ | α-naphthyl |
| 1258 | CH₃ | H | α-naphthyl |
| 1259 | OH | H | α-naphthyl |
| 1260 | C(CH₃)₃ | H | α-naphthyl |
| 1261 | CF₃ | H | α-naphthyl |
| 1262 | CH(CH₃)₂ | H | α-naphthyl |
| 1263 | 2-furyl | H | α-naphthyl |
| 1264 | cyclohexyl | H | α-naphthyl |
| 1265 | cyclobutyl | H | α-naphthyl |
| 1266 | 4-methylphenyl | H | α-naphthyl |
| 1267 | 2-methylphenyl | H | α-naphthyl |
| 1268 | 2-fluorophenyl | H | α-naphthyl |
| 1269 | 3-fluorophenyl | H | α-naphthyl |
| 1270 | 4-fluorophenyl | H | α-naphthyl |
| 1271 | OH | CH₃ | α-naphthyl |
| 1272 | OH | CF₃ | α-naphthyl |
| 1273 | OH | F | α-naphthyl |
| 1274 | OH | CN | α-naphthyl |
| 1275 | OH | Cl | α-naphthyl |
| 1276 | OH | C₂H₅ | α-naphthyl |
| 1277 | phenyl | H | benzo-1,3-dioxol-5-yl |
| 1278 | phenyl | CH₃ | benzo-1,3-dioxol-5-yl |
| 1279 | H | CH₃ | benzo-1,3-dioxol-5-yl |
| 1280 | CH₃ | H | benzo-1,3-dioxol-5-yl |
| 1281 | OH | H | benzo-1,3-dioxol-5-yl |
| 1282 | C(CH₃)₃ | H | benzo-1,3-dioxol-5-yl |
| 1283 | CF₃ | H | benzo-1,3-dioxol-5-yl |
| 1284 | CH(CH₃)₂ | H | benzo-1,3-dioxol-5-yl |
| 1285 | 2-furyl | H | benzo-1,3-dioxol-5-yl |
| 1286 | cyclohexyl | H | benzo-1,3-dioxol-5-yl |
| 1287 | cyclobutyl | H | benzo-1,3-dioxol-5-yl |
| 1288 | 4-methylphenyl | H | benzo-1,3-dioxol-5-yl |
| 1289 | 2-methylphenyl | H | benzo-1,3-dioxol-5-yl |
| 1290 | 2-fluorophenyl | H | benzo-1,3-dioxol-5-yl |
| 1291 | 3-fluorophenyl | H | benzo-1,3-dioxol-5-yl |
| 1292 | 4-fluorophenyl | H | benzo-1,3-dioxol-5-yl |
| 1293 | OH | CH₃ | benzo-1,3-dioxol-5-yl |
| 1294 | OH | CF₃ | benzo-1,3-dioxol-5-yl |
| 1295 | OH | F | benzo-1,3-dioxol-5-yl |
| 1296 | OH | CN | benzo-1,3-dioxol-5-yl |
| 1297 | OH | Cl | benzo-1,3-dioxol-5-yl |
| 1298 | OH | C₂H₅ | benzo-1,3-dioxol-5-yl |
| 1299 | phenyl | H | 2-cyanophenyl |
| 1300 | phenyl | CH₃ | 2-cyanophenyl |
| 1301 | H | CH₃ | 2-cyanophenyl |
| 1302 | CH₃ | H | 2-cyanophenyl |
| 1303 | OH | H | 2-cyanophenyl |
| 1304 | C(CH₃)₃ | H | 2-cyanophenyl |
| 1305 | CF₃ | H | 2-cyanophenyl |
| 1306 | CH(CH₃)₂ | H | 2-cyanophenyl |
| 1307 | 2-furyl | H | 2-cyanophenyl |
| 1308 | cyclohexyl | H | 2-cyanophenyl |
| 1309 | cyclobutyl | H | 2-cyanophenyl |
| 1310 | 4-methylphenyl | H | 2-cyanophenyl |
| 1311 | 2-methylphenyl | H | 2-cyanophenyl |
| 1312 | 2-fluorophenyl | H | 2-cyanophenyl |
| 1313 | 3-fluorophenyl | H | 2-cyanophenyl |
| 1314 | 4-fluorophenyl | H | 2-cyanophenyl |
| 1315 | OH | CH₃ | 2-cyanophenyl |

TABLE 1-continued

| | R¹ | R² | Q |
|---|---|---|---|
| 1316 | OH | CF₃ | 2-cyanophenyl |
| 1317 | OH | F | 2-cyanophenyl |
| 1318 | OH | CN | 2-cyanophenyl |
| 1319 | OH | Cl | 2-cyanophenyl |
| 1320 | OH | C₂H₅ | 2-cyanophenyl |
| 1321 | phenyl | H | 4-cyanophenyl |
| 1322 | phenyl | CH₃ | 4-cyanophenyl |
| 1323 | H | CH₃ | 4-cyanophenyl |
| 1324 | CH₃ | H | 4-cyanophenyl |
| 1325 | OH | H | 4-cyanophenyl |
| 1326 | C(CH₃)₃ | H | 4-cyanophenyl |
| 1327 | CF₃ | H | 4-cyanophenyl |
| 1328 | CH(CH₃)₂ | H | 4-cyanophenyl |
| 1329 | 2-furyl | H | 4-cyanophenyl |
| 1330 | cyclohexyl | H | 4-cyanophenyl |
| 1331 | cyclobutyl | H | 4-cyanophenyl |
| 1332 | 4-methylphenyl | H | 4-cyanophenyl |
| 1333 | 2-methylphenyl | H | 4-cyanophenyl |
| 1334 | 2-fluorophenyl | H | 4-cyanophenyl |
| 1335 | 3-fluorophenyl | H | 4-cyanophenyl |
| 1336 | 4-fluorophenyl | H | 4-cyanophenyl |
| 1337 | OH | CH₃ | 4-cyanophenyl |
| 1338 | OH | CF₃ | 4-cyanophenyl |
| 1339 | OH | F | 4-cyanophenyl |
| 1340 | OH | CN | 4-cyanophenyl |
| 1341 | OH | Cl | 4-cyanophenyl |
| 1342 | OH | C₂H₅ | 4-cyanophenyl |
| 1343 | phenyl | H | 3-trifluoromethylphenyl |
| 1344 | phenyl | CH₃ | 3-trifluoromethylphenyl |
| 1345 | H | CH₃ | 3-trifluoromethylphenyl |
| 1346 | CH₃ | H | 3-trifluoromethylphenyl |
| 1347 | OH | H | 3-trifluoromethylphenyl |
| 1348 | C(CH₃)₃ | H | 3-trifluoromethylphenyl |
| 1349 | CF₃ | H | 3-trifluoromethylphenyl |
| 1350 | CH(CH₃)₂ | H | 3-trifluoromethylphenyl |
| 1351 | 2-furyl | H | 3-trifluoromethylphenyl |
| 1352 | cyclohexyl | H | 3-trifluoromethylphenyl |
| 1353 | cyclobutyl | H | 3-trifluoromethylphenyl |
| 1354 | 4-methylphenyl | H | 3-trifluoromethylphenyl |
| 1355 | 2-methylphenyl | H | 3-trifluoromethylphenyl |
| 1356 | 2-fluorophenyl | H | 3-trifluoromethylphenyl |
| 1357 | 3-fluorophenyl | H | 3-trifluoromethylphenyl |
| 1358 | 4-fluorophenyl | H | 3-trifluoromethylphenyl |
| 1359 | OH | CH₃ | 3-trifluoromethylphenyl |
| 1360 | OH | CF₃ | 3-trifluoromethylphenyl |
| 1361 | OH | F | 3-trifluoromethylphenyl |
| 1362 | OH | CN | 3-trifluoromethylphenyl |
| 1363 | OH | Cl | 3-trifluoromethylphenyl |
| 1364 | OH | C₂H₅ | 3-trifluoromethylphenyl |
| 1365 | phenyl | H | 4-methoxycarbonylphenyl |
| 1366 | phenyl | CH₃ | 4-methoxycarbonylphenyl |
| 1367 | H | CH₃ | 4-methoxycarbonylphenyl |
| 1368 | CH₃ | H | 4-methoxycarbonylphenyl |
| 1369 | OH | H | 4-methoxycarbonylphenyl |
| 1370 | C(CH₃)₃ | H | 4-methoxycarbonylphenyl |
| 1371 | CF₃ | H | 4-methoxycarbonylphenyl |
| 1372 | CH(CH₃)₂ | H | 4-methoxycarbonylphenyl |
| 1373 | 2-furyl | H | 4-methoxycarbonylphenyl |
| 1374 | cyclohexyl | H | 4-methoxycarbonylphenyl |
| 1375 | cyclobutyl | H | 4-methoxycarbonylphenyl |
| 1376 | 4-methylphenyl | H | 4-methoxycarbonylphenyl |
| 1377 | 2-methylphenyl | H | 4-methoxycarbonylphenyl |
| 1378 | 2-fluorophenyl | H | 4-methoxycarbonylphenyl |
| 1379 | 3-fluorophenyl | H | 4-methoxycarbonylphenyl |
| 1380 | 4-fluorophenyl | H | 4-methoxycarbonylphenyl |
| 1381 | OH | CH₃ | 4-methoxycarbonylphenyl |
| 1382 | OH | CF₃ | 4-methoxycarbonylphenyl |
| 1383 | OH | F | 4-methoxycarbonylphenyl |
| 1384 | OH | CN | 4-methoxycarbonylphenyl |
| 1385 | OH | Cl | 4-methoxycarbonylphenyl |
| 1386 | OH | C₂H₅ | 4-methoxycarbonylphenyl |

Examples of further compounds of the general formula I.A are the compounds of the general formulae I.A-1a, I.A-2, I.A-2a, I.A-3, I.A-3a, I.A-4, I.A-4-a, I.A-5 and I.A-5a:

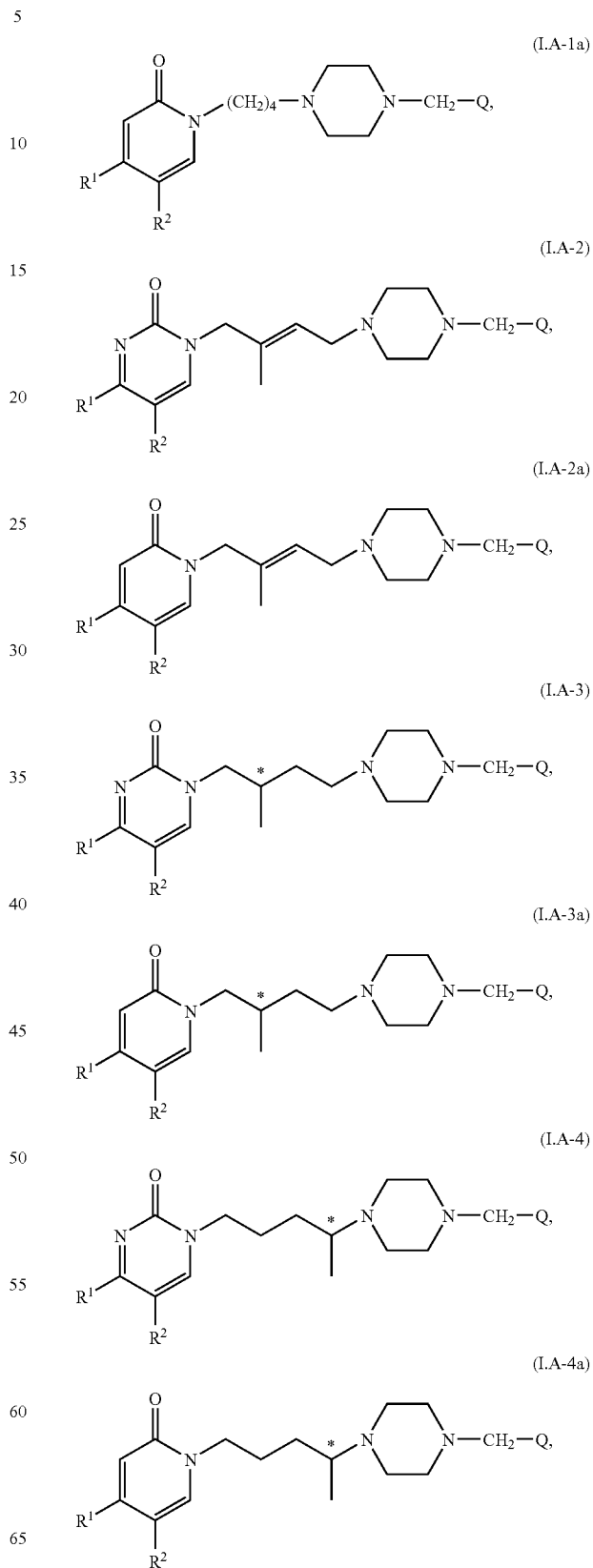

-continued

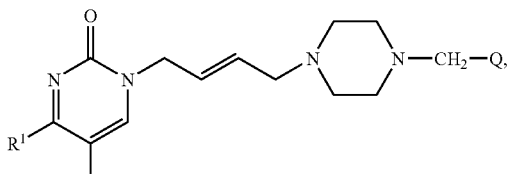
(I.A-5)

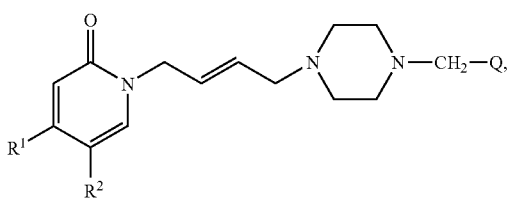
(I.A-5a)

in which $R^1$, $R^2$ and Q have the aforementioned meanings, in particular the meanings indicated as preferred. Examples of such compounds are the compounds I.A-1a.1 to I.A-1a.1386, I.A-2.1 to I.A-2.1386, I.A-2a.1 to I.A-2a.1386, .A-3.1 to I.A-3.1386, I.A-3a. to I.A-3a.1386, A-4.1 to I.A-4.1386, I.A-4-a1. to I.A-4-a.1386, A-5.1 to I.A-5.1386, I.A-5a.1 to I.A-5a.1386, where the variables $R^1$, $R^2$ and Q in each case together have the meaning indicated in one line of Table 1, and for $R^1$=OH the tautomers of these compounds. In the formulae I.A-3, I.A-3a, I.A-4 and I.A-4-a, * indicates a center of asymmetry. In this case, these formulae include both the R and the S enantiomer, and mixtures thereof, e.g. the racemates.

Further examples of compounds of the general formula I.A are the compounds of the general formula I.A-6

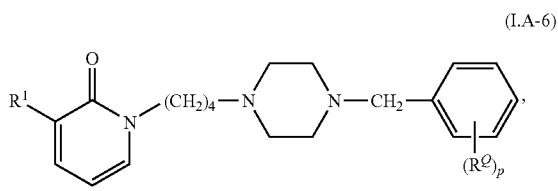
(I.A-6)

in which $R^1$ and $R^a$ have the meanings indicated above, in particular the meanings indicated as preferred, and p is 1, 2 or 3. The groups $R^Q$ may in each case be identical or different and also be connected together. Examples of such compounds are the compounds I.A-6.1 to I.A-6.225, where the variables $R^1$ and $R^a$ in each case together have the meanings indicated in one line of Table 2.

TABLE 2

|  | $R^1$ | $R^Q$ |
|---|---|---|
| 1. | methyl | 2,3-dichloro |
| 2. | methyl | 2,4-dichloro |
| 3. | methyl | 3,4-dichloro |
| 4. | methyl | 2-chloro-3-fluoro |
| 5. | methyl | 2-chloro-4-fluoro |
| 6. | methyl | 3-chloro-4-luoro |
| 7. | methyl | 2-fluoro-3-chloro |
| 8. | methyl | 2-fluoro-4-chloro |
| 9. | methyl | 3-fluoro-4-chloro |
| 10. | methyl | 2-chloro-3-methyl |
| 11. | methyl | 2-chloro-4-methyl |

TABLE 2-continued

|  | $R^1$ | $R^Q$ |
|---|---|---|
| 12. | methyl | 3-chloro-4-methyl |
| 13. | methyl | 2-methyl-3-chloro |
| 14. | methyl | 2-methyl-4-chloro |
| 15. | methyl | 3-methyl-4-chloro |
| 16. | methyl | 2-chloro-3-methoxy |
| 17. | methyl | 2-chloro-4-methoxy |
| 18. | methyl | 3-chloro-4-methoxy |
| 19. | methyl | 2-methoxy-3-chloro |
| 20. | methyl | 2-methoxy-4-chloro |
| 21. | methyl | 3-methoxy-4-chloro |
| 22. | methyl | 2-chloro-3-trifluoromethyl |
| 23. | methyl | 2-chloro-4-trifluoromethyl |
| 24. | methyl | 3-chloro-4-trifluoromethyl |
| 25. | methyl | 2-trifluoromethyl-3-chloro |
| 26. | methyl | 2-trifluoromethyl-4-chloro |
| 27. | methyl | 3-trifluoromethyl-4-chloro |
| 28. | methyl | 2-chloro-3-trifluoromethoxy |
| 29. | methyl | 2-chloro-4-trifluoromethoxy |
| 30. | methyl | 3-chloro-4-trifluoromethoxy |
| 31. | methyl | 2-trifluoromethoxy-3-chloro |
| 32. | methyl | 2-trifluoromethoxy-4-chloro |
| 33. | methyl | 3-trifluoromethoxy-4-chloro |
| 34. | methyl | 2-chloro-3-hydroxy |
| 35. | methyl | 2-chloro-4-hydroxy |
| 36. | methyl | 3-chloro-4-hydroxy |
| 37. | methyl | 2-hydroxy-3-chloro |
| 38. | methyl | 2-hydroxy-4-chloro |
| 39. | methyl | 3-hydroxy-4-chloro |
| 40. | methyl | 2-chloro-3-cyano |
| 41. | methyl | 2-chloro-4-cyano |
| 42. | methyl | 3-chloro-4-cyano |
| 43. | methyl | 2-cyano-3-chloro |
| 44. | methyl | 2-cyano-4-chloro |
| 45. | methyl | 3-cyano-4-chloro |
| 46. | methyl | 2-chloro-3-dimethylamino |
| 47. | methyl | 2-chloro-4-dimethylamino |
| 48. | methyl | 3-chloro-4-dimethylamino |
| 49. | methyl | 2-dimethylamino-3-chloro |
| 50. | methyl | 2-dimethylamino-4-chloro |
| 51. | methyl | 3-dimethylamino-4-chloro |
| 52. | methyl | 2-chloro-3-cyclopropyl |
| 53. | methyl | 2-chloro-4-cyclopropyl |
| 54. | methyl | 3-chloro-4-cyclopropyl |
| 55. | methyl | 2-cyclopropyl-3-chloro |
| 56. | methyl | 2-cyclopropyl-4-chloro |
| 57. | methyl | 3-cyclopropyl-4-chloro |
| 58. | methyl | 2,3-dimethyl |
| 59. | methyl | 2,4-dimethyl |
| 60. | methyl | 3,4-dimethyl |
| 61. | methyl | 2,3-dimethoxy |
| 62. | methyl | 2,4-dimethoxy |
| 63. | methyl | 3,4-dimethoxy |
| 64. | methyl | 2-methyl-3-methoxy |
| 65. | methyl | 2-methyl-4-methoxy |
| 66. | methyl | 3-methyl-4-methoxy |
| 67. | methyl | 2-methoxy-3-methyl |
| 68. | methyl | 2-methoxy-4-methyl |
| 69. | methyl | 3-methoxy-4-methyl |
| 70. | methyl | 2-trifluoromethoxy-3-methoxy |
| 71. | methyl | 2-trifluoromethoxy-4-methoxy |
| 72. | methyl | 3-trifluoromethoxy-4-methoxy |
| 73. | methyl | 2-methoxy-3-trifluoromethoxy |
| 74. | methyl | 2-methoxy-4-trifluoromethoxy |
| 75. | methyl | 3-methoxy-4-trifluoromethoxy |
| 76. | methoxy | 2,3-dichloro |
| 77. | methoxy | 2,4-dichloro |
| 78. | methoxy | 3,4-dichloro |
| 79. | methoxy | 2-chloro-3-fluoro |
| 80. | methoxy | 2-chloro-4-fluoro |
| 81. | methoxy | 3-chloro-4-fluoro |
| 82. | methoxy | 2-fluoro-3-chloro |
| 83. | methoxy | 2-fluoro-4-chloro |
| 84. | methoxy | 3-fluoro-4-chloro |
| 85. | methoxy | 2-chloro-3-methyl |
| 86. | methoxy | 2-chloro-4-methyl |
| 87. | methoxy | 3-chloro-4-methyl |
| 88. | methoxy | 2-methyl-3-chloro |
| 89. | methoxy | 2-methyl-4-chloro |

TABLE 2-continued

| | R¹ | R^Q |
|---|---|---|
| 90. | methoxy | 3-methyl-4-chloro |
| 91. | methoxy | 2-chloro-3-methoxy |
| 92. | methoxy | 2-chloro-4-methoxy |
| 93. | methoxy | 3-chloro-4-methoxy |
| 94. | methoxy | 2-methoxy-3-chloro |
| 95. | methoxy | 2-methoxy-4-chloro |
| 96. | methoxy | 3-methoxy-4-chloro |
| 97. | methoxy | 2-chloro-3-trifluoromethyl |
| 98. | methoxy | 2-chloro-4-trifluoromethyl |
| 99. | methoxy | 3-chloro-4-trifluoromethyl |
| 100. | methoxy | 2-trifluoromethyl-3-chloro |
| 101. | methoxy | 2-trifluoromethyl-4-chloro |
| 102. | methoxy | 3-trifluoromethyl-4-chloro |
| 103. | methoxy | 2-chloro-3-trifluoromethoxy |
| 104. | methoxy | 2-chloro-4-trifluoromethoxy |
| 105. | methoxy | 3-chloro-4-trifluoromethoxy |
| 106. | methoxy | 2-trifluoromethoxy-3-chloro |
| 107. | methoxy | 2-trifluoromethoxy-4-chloro |
| 108. | methoxy | 3-trifluoromethoxy-4-chloro |
| 109. | methoxy | 2-chloro-3-hydroxy |
| 110. | methoxy | 2-chloro-4-hydroxy |
| 111. | methoxy | 3-chloro-4-hydroxy |
| 112. | methoxy | 2-hydroxy-3-chloro |
| 113. | methoxy | 2-hydroxy-4-chloro |
| 114. | methoxy | 3-hydroxy-4-chloro |
| 115. | methoxy | 2-chloro-3-cyano |
| 116. | methoxy | 2-chloro-4-cyano |
| 117. | methoxy | 3-chloro-4-cyano |
| 118. | methoxy | 2-cyano-3-chloro |
| 119. | methoxy | 2-cyano-4-chloro |
| 120. | methoxy | 3-cyano-4-chloro |
| 121. | methoxy | 2-chloro-3-dimethylamino |
| 122. | methoxy | 2-chloro-4-dimethylamino |
| 123. | methoxy | 3-chloro-4-dimethylamino |
| 124. | methoxy | 2-dimethylamino-3-chloro |
| 125. | methoxy | 2-dimethylamino-4-chloro |
| 126. | methoxy | 3-dimethylamino-4-chloro |
| 127. | methoxy | 2-chloro-3-cyclopropyl |
| 128. | methoxy | 2-chloro-4-cyclopropyl |
| 129. | methoxy | 3-chloro-4-cyclopropyl |
| 130. | methoxy | 2-cyclopropyl-3-chloro |
| 131. | methoxy | 2-cyclopropyl-4-chloro |
| 132. | methoxy | 3-cyclopropyl-4-chloro |
| 133. | methoxy | 2,3-dimethyl |
| 134. | methoxy | 2,4-dimethyl |
| 135. | methoxy | 3,4-dimethyl |
| 136. | methoxy | 2,3-dimethoxy |
| 137. | methoxy | 2,4-dimethoxy |
| 138. | methoxy | 3,4-dimethoxy |
| 139. | methoxy | 2-methyl-3-methoxy |
| 140. | methoxy | 2-methyl-4-methoxy |
| 141. | methoxy | 3-methyl-4-methoxy |
| 142. | methoxy | 2-methoxy-3-methyl |
| 143. | methoxy | 2-methoxy-4-methyl |
| 144. | methoxy | 3-methoxy-4-methyl |
| 145. | methoxy | 2-trifluoromethoxy-3-methoxy |
| 146. | methoxy | 2-trifluoromethoxy-4-methoxy |
| 147. | methoxy | 3-trifluoromethoxy-4-methoxy |
| 148. | methoxy | 2-methoxy-3-trifluoromethoxy |
| 149. | methoxy | 2-methoxy-4-trifluoromethoxy |
| 150. | methoxy | 3-methoxy-4-trifluoromethoxy |
| 151. | trifluoromethyl | 2,3-dichloro |
| 152. | trifluoromethyl | 2,4-dichloro |
| 153. | trifluoromethyl | 3,4-dichloro |
| 154. | trifluoromethyl | 2-chloro-3-fluoro |
| 155. | trifluoromethyl | 2-chloro-4-fluoro |
| 156. | trifluoromethyl | 3-chloro-4-fluoro |
| 157. | trifluoromethyl | 2-fluoro-3-chloro |
| 158. | trifluoromethyl | 2-fluoro-4-chloro |
| 159. | trifluoromethyl | 3-fluoro-4-chloro |
| 160. | trifluoromethyl | 2-chloro-3-methyl |
| 161. | trifluoromethyl | 2-chloro-4-methyl |
| 162. | trifluoromethyl | 3-chloro-4-methyl |
| 163. | trifluoromethyl | 2-methyl-3-chloro |
| 164. | trifluoromethyl | 2-methyl-4-chloro |
| 165. | trifluoromethyl | 3-methyl-4-chloro |
| 166. | trifluoromethyl | 2-chloro-3-methoxy |
| 167. | trifluoromethyl | 2-chloro-4-methoxy |
| 168. | trifluoromethyl | 3-chloro-4-methoxy |
| 169. | trifluoromethyl | 2-methoxy-3-chloro |
| 170. | trifluoromethyl | 2-methoxy-4-chloro |
| 171. | trifluoromethyl | 3-methoxy-4-chloro |
| 172. | trifluoromethyl | 2-chloro-3-trifluoromethyl |
| 173. | trifluoromethyl | 2-chloro-4-trifluoromethyl |
| 174. | trifluoromethyl | 3-chloro-4-trifluoromethyl |
| 175. | trifluoromethyl | 2-trifluoromethyl-3-chloro |
| 176. | trifluoromethyl | 2-trifluoromethyl-4-chloro |
| 177. | trifluoromethyl | 3-trifluoromethyl-4-chloro |
| 178. | trifluoromethyl | 2-chloro-3-trifluoromethoxy |
| 179. | trifluoromethyl | 2-chloro-4-trifluoromethoxy |
| 180. | trifluoromethyl | 3-chloro-4-trifluoromethoxy |
| 181. | trifluoromethyl | 2-trifluoromethoxy-3-chloro |
| 182. | trifluoromethyl | 2-trifluoromethoxy-4-chloro |
| 183. | trifluoromethyl | 3-trifluoromethoxy-4-chloro |
| 184. | trifluoromethyl | 2-chloro-3-hydroxy |
| 185. | trifluoromethyl | 2-chloro-4-hydroxy |
| 186. | trifluoromethyl | 3-chloro-4-hydroxy |
| 187. | trifluoromethyl | 2-hydroxy-3-chloro |
| 188. | trifluoromethyl | 2-hydroxy-4-chloro |
| 189. | trifluoromethyl | 3-hydroxy-4-chloro |
| 190. | trifluoromethyl | 2-chloro-3-cyano |
| 191. | trifluoromethyl | 2-chloro-4-cyano |
| 192. | trifluoromethyl | 3-chloro-4-cyano |
| 193. | trifluoromethyl | 2-cyano-3-chloro |
| 194. | trifluoromethyl | 2-cyano-4-chloro |
| 195. | trifluoromethyl | 3-cyano-4-chloro |
| 196. | trifluoromethyl | 2-chloro-3-dimethylamino |
| 197. | trifluoromethyl | 2-chloro-4-dimethylamino |
| 198. | trifluoromethyl | 3-chloro-4-dimethylamino |
| 199. | trifluoromethyl | 2-dimethylamino-3-chloro |
| 200. | trifluoromethyl | 2-dimethylamino-4-chloro |
| 201. | trifluoromethyl | 3-dimethylamino-4-chloro |
| 202. | trifluoromethyl | 2-chloro-3-cyclopropyl |
| 203. | trifluoromethyl | 2-chloro-4-cyclopropyl |
| 204. | trifluoromethyl | 3-chloro-4-cyclopropyl |
| 205. | trifluoromethyl | 2-cyclopropyl-3-chloro |
| 206. | trifluoromethyl | 2-cyclopropyl-4-chloro |
| 207. | trifluoromethyl | 3-cyclopropyl-4-chloro |
| 208. | trifluoromethyl | 2,3-dimethyl |
| 209. | trifluoromethyl | 2,4-dimethyl |
| 210. | trifluoromethyl | 3,4-dimethyl |
| 211. | trifluoromethyl | 2,3-dimethoxy |
| 212. | trifluoromethyl | 2,4-dimethoxy |
| 213. | trifluoromethyl | 3,4-dimethoxy |
| 214. | trifluoromethyl | 2-methyl-3-methoxy |
| 215. | trifluoromethyl | 2-methyl-4-methoxy |
| 216. | trifluoromethyl | 3-methyl-4-methoxy |
| 217. | trifluoromethyl | 2-methoxy-3-methyl |
| 218. | trifluoromethyl | 2-methoxy-4-methyl |
| 219. | trifluoromethyl | 3-methoxy-4-methyl |
| 220. | trifluoromethyl | 2-trifluoromethoxy-3-methoxy |
| 221. | trifluoromethyl | 2-trifluoromethoxy-4-methoxy |
| 222. | trifluoromethyl | 3-trifluoromethoxy-4-methoxy |
| 223. | trifluoromethyl | 2-methoxy-3-trifluoromethoxy |
| 224. | trifluoromethyl | 2-methoxy-4-trifluoromethoxy |
| 225. | trifluoromethyl | 3-methoxy-4-trifluoromethoxy |

The substituted N-heterocyclic compounds I of the invention are prepared in analogy to methods disclosed in the literature. One important route to the compounds I.A of the invention is shown in Scheme 1.

Scheme 1:

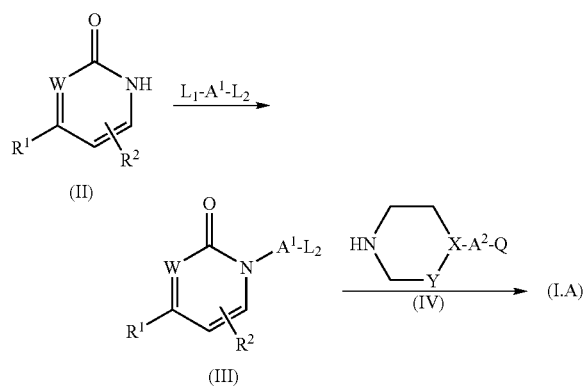

In Scheme 1, W, $R^1$, $R^2$, $A^1$, X, Y and Q have the aforementioned meanings. $L_1$ and $L_2$ are nucleophilically displaceable leaving groups. Examples of suitable nucleophilically displaceable leaving groups are halogen, especially chlorine, bromine or iodine, alkyl- and arylsulfonate such as mesylate, tosylate. $L_1$ and $L_2$ are preferably different from one another and show different reactivity. For example, $L_1$ is bromine or iodine and $L_2$ is chlorine. The reaction conditions necessary for the reaction correspond to the reaction conditions usual for nucleophilic substitutions.

Compounds of the general formula IV are in some cases commercially available and/or disclosed in the literature, e.g. in Chem. Pharm. Bull. 1987, 35 (7), 2782-91; Bioorganical and Medicinal Chemistry Letters (BOMCL) 2002, 12 (8), 1149-52; J. Med. Chem. 1998, 33 (5), 339-47; J. Med. Chem. 1989, 32 (3), 593-7; JCS. Perkin Trans 1: Org. and Bioorg. Chem. 1998, 15, 2239-42; Chem. Pharm. Bull. 1988, 36 (12), 4825-33.

The pyrimidinone compounds of the formulae II (with W=N) are known and in some cases commercially available or can be prepared by known methods of pyrimidinone synthesis as described for example in Austr. J. Chem. 1968, 221, pp. 243-255; J. Med. Chem. 1978, 21, pp. 623-628; Tetrahedron Lett. 1986, 27, pp. 2611-2612; Chemiker Ztg. 1977, 6, p. 305.

The pyridinone compounds of the formulae II (with W=CH or $CR^1$) are known and in some cases commercially available or can be prepared by known methods of pyridinone synthesis as described for example in J. Med. Chem. 16(5), 1973, pp. 524-528, J. Org. Chem., 67, 2002, pp. 4304-4308, Bioorg. Med. Chem. Lett, 12, 2002, pp. 3537-3541.

The compounds II can also be prepared by methods indicated in Schemes 2, 3 and 4.

Thus, the compounds of the formula II if $R^1$ is optionally substituted alkenyl, optionally substituted phenyl or optionally substituted C-linked heteroaryl can be prepared by the route shown in Scheme 2 by Suzuki coupling.

Scheme 2:

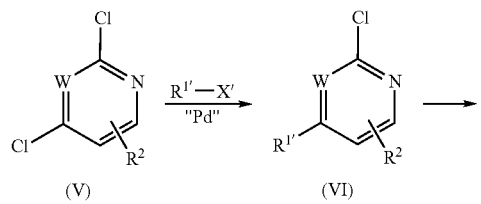

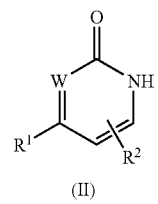

In Scheme 2, W has the meanings indicated above. $R^{1'}$ is optionally substituted alkenyl, optionally substituted phenyl or optionally substituted, C-linked heteroaryl. X' is a group $B(OH)_2$, $B(OR)_2$ or is the residue $(BO)_3/3$ derived from the corresponding boronic anhydride. "Pd" stands for a palladium(0) complex which preferably has 4 trialkylphosphine or triarylphosphine ligands. $R^2$ has the meanings indicated above and is in particular hydrogen or $C_1$-$C_4$-alkyl.

The coupling of V with the compound R'-X' takes place under the conditions of a Suzuki coupling (for review, see A. Suzuki et al. in Chem. Rev. 1995, 95, pp. 2457-2483). The reaction conditions necessary for the Suzuki coupling of 2,4-dichloropyrimidines V with $R^1$—X' are disclosed in the literature, e.g. in J. Org. Chem. 66(21) (2001), pp. 7124-7128. The 2-chloropyrimidine VI obtained in this way can be converted in a manner known per se, e.g. under the conditions indicated in Acta Chem. Scand. B, 1984, 38, pp. 505-508, into the corresponding 2-pyrimidinone II.

A further possibility is for the compounds of the formula II in which W=N and $R^1$ is optionally substituted $C_1$-$C_6$-alkyl or $C_3$-$C_6$-cycloalkyl, in particular is ethyl, isopropyl, cyclopropyl, cyclobutyl, cyclohexyl, and $R^2$ is H, to be prepared for example by the method shown in Scheme 3.

Scheme 3:

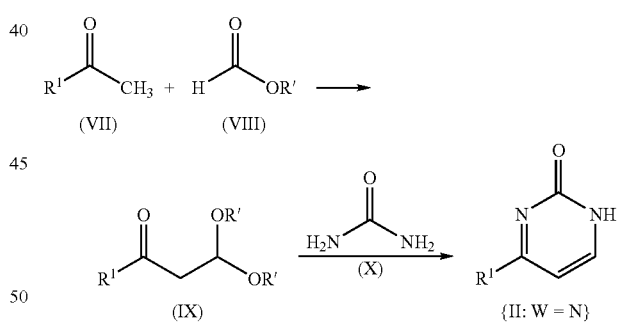

In Scheme 3, R' is for example $C_1$-$C_4$-alkyl. In Scheme 3, firstly a ketone VII is converted into the ketal IX using a formic ester VIII, e.g. methyl formate, in a manner known per se (see Helv. Chim. Acta 2002, 85, 2926-2929, Ex. 6). The reaction is normally carried out in the presence of a base such as an alcoholate in an inert solvent such as an ether. The reaction of the resulting ketal IX with urea X to form the corresponding 2-pyrimidinone II takes place under conditions disclosed in the literature, e.g. as in Aust. J. Chem. 1968, 21, 243-55 (especially p. 252).

The 2-pyri(mi)dinones II in which $R^1$ is hydrogen, and $R^2$ is optionally substituted phenyl, can be prepared for example by the method shown in Scheme 4.

Scheme 4:

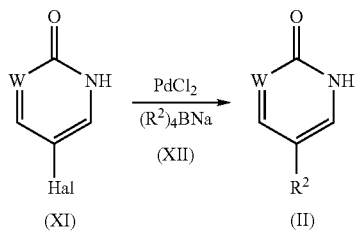

In Scheme 4, W has the meanings indicated above. Hal is halogen, especially bromine or chlorine. The coupling of the halopyrimidinone XI with the borate XII takes place under Suzuki conditions (see Tetrahedron 1997, 53, 14437-50). The modified Suzuki cross-coupling between the pyridinone XI and the borate XII normally takes place in aqueous solvents in the presence of a phosphine-free Pd catalyst such as palladium(II) chloride and in the presence of a base. Examples of suitable bases are alkali metal hydroxides such as sodium hydroxide. The pyridinones XI and the borates XII are disclosed in the literature and commercially available.

The pyri(mi)dinone compounds I.A of the invention, in which $R^1$ is $NR^4R^5$, can be prepared for example by the method shown in Scheme 5.

Scheme 5:

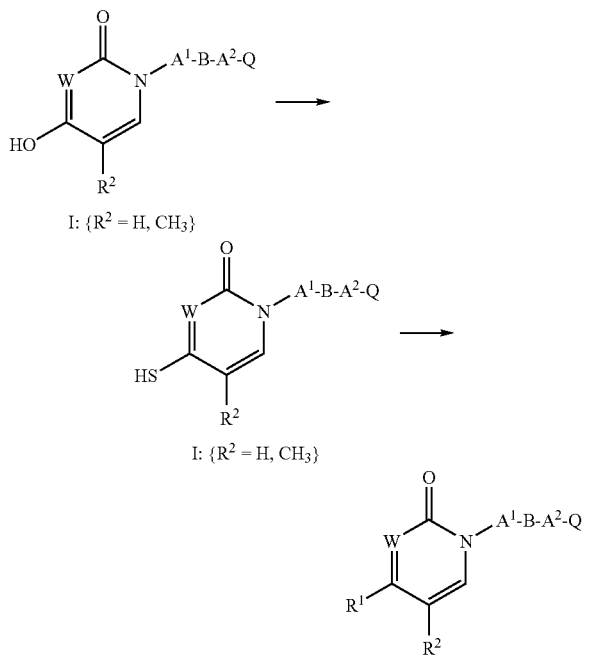

In Scheme 5, W, $A^1$, B, $A^2$ and Q have the meanings indicated above. As shown in Scheme 5, firstly the compound I.A in which $R^1$ is OH is converted into the corresponding thiol I with $R^1$=SH. Examples of suitable sulfurizing agents are organophosphorus sulfides such as Lawesson's reagent, organotin sulfides or phosphorus(V) sulfide. A preferred sulfurizing agent is phosphorus pentasulfide ($P_4S_{10}$). The conditions necessary for the thionation are known to the skilled worker, e.g. from J. Med. Chem. 1984, 27, 1470-80 (especially p. 1478, Example 8b). The thiol I with $R^1$=SH which is obtained in this case can be converted into other compounds I.A with $R^1$=$NR^4R^5$ by reaction with a compound of the formula $HNR^4R^5$ in which $R^4$ and $R^5$ have the abovementioned meanings. The reaction normally takes place in an inert solvent. The energy of activation necessary for the reaction can be introduced into the reaction mixture by means of microwaves (for reaction employing microwaves, see Tetrahedron 2001, 57, pp. 9199 et seq., pp. 9225 et seq. and generally "Microwaves in Organic Synthesis", André Loupy (ed.), Wiley-VCH 2002).

The thiol group in the compounds I.A with $R^1$=SH can be converted into other radicals $R^1$ by standard methods of organic chemistry. Scheme 6 gives an overview.

Scheme 6:

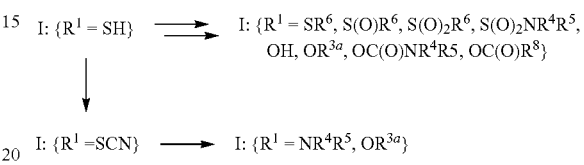

Methods for this are known to the skilled worker and include the conversion of SH into $SR^6$ by alkylation, the oxidation of $SR^6$ to give the corresponding $SOR^6$ and $SO_2R^6$ groups, the oxidative degradation of SH to OH with, where appropriate, subsequent alkylation or esterification to give the groups $OR^{3a}$, $OC(O)NR^4R^5$ or $OC(O)R^8$.

Pyrimidinone compounds II in which W=N and $R^1$ is $NR^4R^5$ can be prepared for example in analogy to Scheme 5 above. The preparation is outlined in Scheme 7.

Scheme 7:

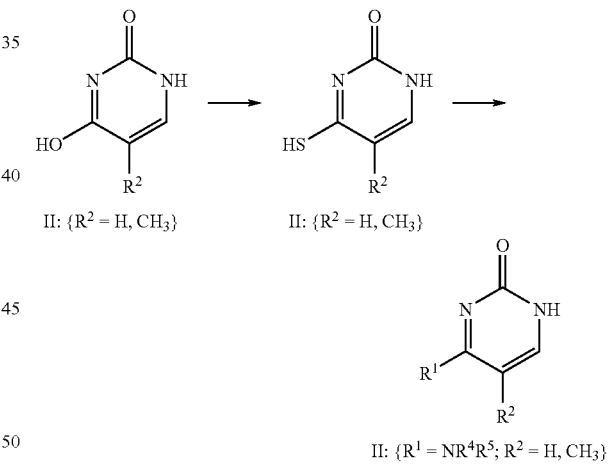

Tautomers of the formula I.A can be prepared in a manner analogous to the preparation described herein of the compound I.A. For example, the tautomeric derivatives I.A-a

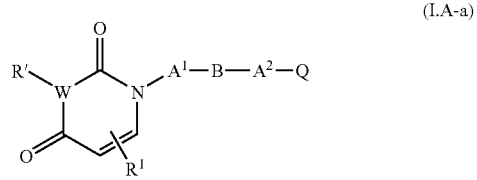

(I.A-a)

in which R' is H or $C_1$-$C_4$-alkyl, can be prepared in analogy to the synthetic route shown in Scheme 1.

In addition, tautomers of the formula I.A-a with R'=methyl can also be obtained by treating the H-analogous compound with an excess of, for example, 5 molar equivalents of MeI/KOH in DMSO at room temperature for several hours, as shown in Scheme 8.

Scheme 8:

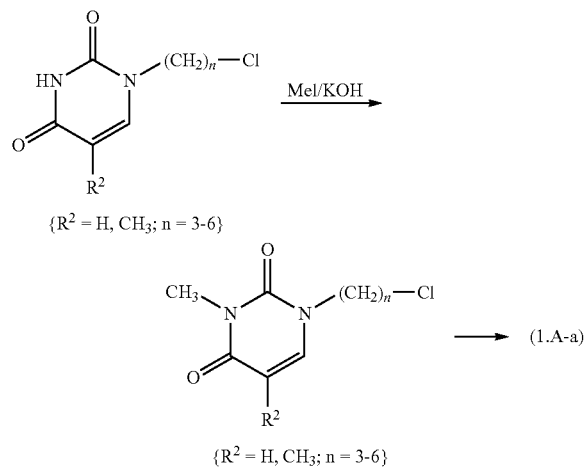

In addition, the compound I.A can be converted into its tautomers I.A-b

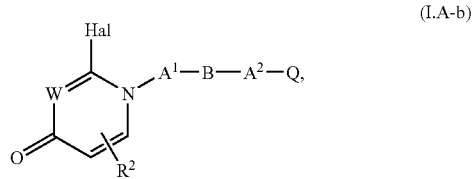

in which Hal is halogen by treating it with a suitable halogenating agent such as $PCl_3$ or $POCl_3$.

Unless indicated otherwise, the reactions described above generally take place in a solvent at temperatures between room temperature and the boiling point of the solvent used. Examples of solvents which can be used are ethers such as diethyl ether, diisopropyl ether, methyl-tert-butyl ether or tetrahydrofuran, dimethylformamide, dimethyl sulfoxide, dimethoxyethane, toluene, xylene, acetonitrile, ketones such as acetone or methyl ethyl ketone, or alcohols such as methanol, ethanol or butanol.

The energy of activation necessary for the reaction can be introduced into the reaction mixture by means of microwaves (for reaction employing microwaves, see Tetrahedron 2001, 57, pp. 9199 et seq., pp. 9225 et seq., and generally "Microwaves in Organic Synthesis", André Loupy (ed.), Wiley-VCH 2002).

If desired, a base is present to neutralize protons liberated during the reactions. Suitable bases include inorganic bases such as sodium or potassium carbonate, sodium or potassium bicarbonate, in addition alcoholates such as sodium methoxide, sodium ethoxide, alkali metal hydrides such as sodium hydride, organometallic compounds such as butyllithium or alkylmagnesium compounds, or organic nitrogen bases such as triethylamine or pyridine. The latter may serve simultaneously as solvents.

The crude product is isolated in a conventional way, for example by filtration, removal of the solvent by distillation or extraction from the reaction mixture etc. The resulting compounds can be purified in a conventional way, for example by recrystallization from a solvent, chromatography or by conversion into an acid addition salt.

The acid addition salts are prepared in a conventional way by mixing the free base with the appropriate acid, where appropriate in solution in an organic solvent, for example a low molecular weight alcohol such as methanol, ethanol or propanol, an ether such as methyl t-butyl ether or diisopropyl ether, a ketone such as acetone or methyl ethyl ketone or an ester such as ethyl acetate.

The compounds of the invention of the formula I are highly selective dopamine $D_3$ receptor ligands which, because of their low affinity for other receptors, in particular for dopamine $D_2$ receptors, have fewer side effects than classical neuroleptics which comprise $D_2$ receptor antagonists.

The high affinity of the compounds of the invention for $D_3$ receptors is reflected in very low in vitro $K_i$ values of ordinarily less than 100 nM (nmol/l) and especially of less than 50 nM. Binding affinities for $D_3$ receptors can for example be determined via the displacement of [$^{125}$I]-iodosulpride in receptor-binding studies.

Particularly important according to the invention are compounds whose selectivity $K_i(D_2)/K_i(D_3)$ is preferably at least 10, even better at least 30 and particularly advantageously at least 50. Receptor-binding studies on $D_1$, $D_2$ and $D_4$ receptors can be carried out for example via the displacement of [$^3$H] SCH23390, [$^{125}$I]iodosulpride and [$^{125}$I]spiperone.

The compounds can, because of their binding profile, be used for the treatment of conditions which respond to dopamine $D_3$ ligands, i.e. they are effective for the treatment of those disorders or conditions where an influencing (modulation) of dopamine $D_3$ receptors leads to an improvement in the clinical condition or to cure of the disease. Examples of such conditions are disorders or conditions of the central nervous system.

Disorders or conditions of the central nervous system mean disorders affecting the spinal cord and, in particular, the brain. The term "disorder" in the sense according to the invention refers to abnormalities which are usually regarded as pathological states or functions and may reveal themselves in the form of particular signs, symptoms and/or dysfunctions. The inventive treatment may be directed at individual disorders, i.e. abnormalities or pathological states, but it is also possible for a plurality of abnormalities, which are causally connected together where appropriate, to be combined into patterns, i.e. syndromes, which can be treated according to the invention.

The disorders which can be treated according to the invention include in particular psychiatric and neurological disorders. These comprise in particular organic disorders, symptomatic disorders included, such as psychoses of the acute exogenous type or associated psychoses with an organic or exogenous cause, e.g. associated with metabolic disorders, infections and endocrinopathies; endogenous psychoses such as schizophrenia and schizotypal and delusional disorders; affective disorders such as depressions, mania and manic/depressive states; and combined forms of the disorders described above; neurotic and somatoform disorders, and disorders associated with stress; dissociative disorders, e.g. deficits, clouding and splitting of consciousness and personality disorders; disorders of attention and waking/sleeping behavior, such as behavioral disorders and emotional disorders starting in childhood and adolescence, e.g. hyperactivity in children, intellectual deficits, especially attention deficit disorders, disorders of memory and cognition, e.g. learning and memory impairment (impaired cognitive function), dementia, narcolepsy and sleeping disorders, e.g. restless legs syndrome; developmental disorders; anxiety states; delirium; disorders of the sex life, e.g. male impotence; eating disorders, e.g. anorexia or bulimia; addiction; and other undefined psychiatric disorders.

The disorders which can be treated according to the invention also include parkinsonism and epilepsy and, in particular, the affective disorders associated therewith. Addictive disorders include the psychological disorders and behavioral disorders caused by the abuse of psychotropic substances such as pharmaceuticals or drugs, and other addictive disorders such as, for example, compulsive gambling (impulse control disorders not elsewhere classified). Examples of addictive substances are: opioids (e.g. morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methylamphetamine (Ecstasy); amphetamine and amphetamine-like substances such as methylphenidate or other stimulants, including caffeine. Addictive substances requiring particular attention are opioids, cocaine, amphetamine or amphetamine-like substances, nicotine and alcohol. With a view to the treatment of addictive disorders, the compounds of the invention of the formula I which are particularly preferred are those which themselves have no psychotropic effect. This can also be observed in a test on rats which reduce the selfadministration of psychotropic substances, for example cocaine, after administration of compounds which can be used according to the invention.

According to a further aspect of the present invention, the compounds of the invention are suitable for the treatment of disorders, the causes of which can at least in part be attributed to an abnormal activity of dopamine $D_3$ receptors.

According to another aspect of the present invention, the treatment is directed in particular at those disorders which can be influenced by a binding of, preferably exogenously added, binding partners (ligands) to dopamine $D_3$ receptors in the sense of an expedient medical treatment.

The conditions which can be treated with the compounds of the invention are frequently characterized by a progressive development, i.e. the states described above change over the course of time, the severity usually increasing and, where appropriate, states possibly interchanging or other states being added to previously existing states.

The compounds of the invention can be used to treat a large number of signs, symptoms and/or dysfunctions associated with the disorders of the central nervous system and in particular the aforementioned states. These include for example a distorted relation to reality, lack of insight and the ability to comply with the usual social norms and demands of life, changes in behavior, changes in individual urges such as hunger, sleep, thirst etc. and in mood, disorders of memory and association, personality changes, especially emotional liability, hallucinations, ego disturbances, incoherence of thought, ambivalence, autism, depersonalization or hallucinations, delusional ideas, staccato speech, absence of associated movement, small-step gait, bent posture of trunk and limbs, tremor, mask-like face, monotonous speech, depression, apathy, deficient spontaneity and irresolution, reduced association ability, anxiety, nervous agitation, stammering, social phobia, panic disorders, withdrawal syndromes associated with dependence, expansive syndromes, states of agitation and confusion, dysphoria, dyskinetic syndromes and tic disorders, e.g. Huntington's chorea, Gilles de la Tourette syndrome, vertigo syndromes, e.g. peripheral postural, rotational and vestibular vertigo, melancholia, hysteria, hypochondria and the like. A treatment in the sense according to the invention includes not only the treatment of acute or chronic signs, symptoms and/or dysfunctions but also a preventive treatment (prophylaxis), in particular as recurrence or episode prophylaxis. The treatment may be symptomatic, for example directed at suppression of symptom. It may take place short-term, be directed at the medium term or may also be a long-term treatment, for example as part of maintenance therapy.

The compounds of the invention are preferably suitable for the treatment of disorders of the central nervous system, especially for the treatment of affective disorders; neurotic disorders, stress disorders and somatoform disorders and psychoses and specifically for the treatment of schizophrenia and depression. Owing to their high selectivity in relation to the $D_3$ receptor, the compounds I of the invention are also for the treatment of renal function disorders, especially of renal function disorders caused by diabetes mellitus (see WO 00/67847).

The inventive use of the described compounds comprises a method within the scope of the treatment. This entails the individual to be treated, preferably a mammal, in particular a human or agricultural or domestic animal, being given an effective amount of one or more compounds, usually formulated in accordance with pharmaceutical and veterinary practice. Whether such a treatment is indicated, and the form it is to take, depends on the individual case and is subject to a medical assessment (diagnosis) which takes account of the signs, symptoms and/or dysfunctions present, the risks of developing certain signs, symptoms and/or dysfunctions, and other factors. The treatment usually takes place by administration once or more than once a day, where appropriate together or alternately with other active ingredients or active ingredient containing products, so that an individual to be treated is given a daily dose preferably of about 0.1 to 1000 mg/kg of body weight on oral administration or of about 0.1 to 100 mg/kg of body weight on parenteral administration. The invention also relates to the production of pharmaceutical compositions for the treatment of an individual, preferably a mammal, in particular a human or agricultural or domestic animal. Thus, the ligands are usually administered in the form of pharmaceutical compositions which comprise a pharmaceutically acceptable excipient with at least one ligand of the invention and, where appropriate, further active ingredients. These compositions can be administered for example by the oral, rectal, transdermal, subcutaneous, intravenous, intramuscular or intranasal route.

Examples of suitable pharmaceutical formulations are solid pharmaceutical forms such as oral powders, dusting powders, granules, tablets, especially film-coated tablets, pastilles, sachets, cachets, sugar-coated tablets, capsules such as hard and soft gelatin capsules, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops. Implanted delivery devices can also be used to administer compounds of the invention. A further possibility is also to use liposomes or microspheres. The compositions are produced by mixing or diluting inhibitors of the invention usually with an excipient. Excipients may be solid, semisolid or liquid materials which serve as vehicle, carrier or medium for the active ingredient.

Suitable excipients are listed in the relevant pharmaceutical monographs. The formulations may additionally comprise pharmaceutically acceptable carriers or conventional excipients such as lubricants; wetting agents; emulsifying and suspending agents; preservatives; antioxidants; antiirritants; chelating agents; tablet-coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients, such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Kantor-Verlag, 1996.

The following examples serve to illustrate the invention without limiting it.

The nuclear magnetic resonance spectral properties (NMR) relate to chemical shifts ($\delta$) expressed in parts per million (ppm). The relative area for the shifts in the $^1$H NMR spectrum corresponds to the number of hydrogen atoms for a particular functional type in the molecule. The nature of the shift in terms of multiplicity is indicated as singlet (s), broad singlet (s. br.), doublet (d), broad doublet (d br.), triplet (t), broad triplet (t br.), quartet (q), quintet (quint.), multiplet (m).

PREPARATION EXAMPLES

Precursors a.
1-(4-Chlorobutyl)-5-methyl-1H-pyrimidine-2,4-dione 10.1 g (80.0 mmol) of 4-hydroxy-5-methylpyrimidin-2 (1H)-one (thymine) in 300 ml of dimethyl sulfoxide (DMSO) and 11.1 g (80.0 mmol) of $K_2CO_3$ were stirred at room temperature for 1 hour. Then 13.7 g (80.0 mmol) of 1-bromo-4-chlorobutane were added dropwise to the mixture, and the reaction mixture was then stirred at room temperature for 5 hours. Water was added to the reaction mixture, and it was then extracted with ethyl acetate. The aqueous phase was then neutralized and extracted with methylene chloride. Drying of the organic phase, removal of the desiccant by filtration and evaporation of the solvent to dryness in vacuo resulted in 7.1 g of the title compound
ESI-MS: 219.1, [M+H$^+$]=217.1;
$^1$H NMR (500 MHz, CDCl$_3$) $\delta$(ppm): 9.97 (1H, s.), 7.02 (1H, s.), 3.74 (2H, t), 3.55 (2H, t), 1.93 (3H, s), 2.02-1.75 (4H, m).

b. 1-(4-Chlorobutyl)-1H-pyrimidine-2,4-dione

The title compound was prepared in analogy to the procedure described in J. Am. Chem. Soc. 1993, 115, 7636 for preparing 1-(4-bromobutyl)pyrimidine-2,4(1H,3H)dione.

c. 1-(4-Chlorobutyl)-4-phenyl-1H-pyrimidin-2-one c.1 2-Chloro-4-phenylpyrimidin 2.78 g (20.14 mmol) of $K_2CO_3$, 0.21 g (0.18 mmol) of tetrakis(triphenylphosphine)Pd(0) were added to 1.00 g (6.71 mmol) of 2,4-dichloropyrimidine and 0.82 g (6.71 mmol) of benzeneboronic acid in 29 ml of toluene and 7 ml of methanol, and the reaction mixture was stirred at room temperature for 3 hours. The residue after concentration of the reaction mixture was taken up in water/methyl tert-butyl ether. The aqueous phase was then extracted twice with methyl tert-butyl ether. The combined organic phase was then washed with water and with a saturated aqueous NaCl solution, and the organic phase was dried, filtered to remove the desiccant and concentrated. The solid brown residue was purified by flash chromatography on silica gel (mobile phase: ethyl acetate/cyclohexane: 10:90); yield: 0.90 g.
$^1$H NMR (400 MHz, CDCl$_3$) $\delta$ (ppm): 8.64 (1H, d), 8.10 (2H, d), 7.650 (1H, d), 7.58-7.48 (3H, m).

c.2 4-Phenylpyrimidin-2-ol 0.80 g (4.20 mmol) of 2-chloro-4-phenylpyrimidine from c.1 was heated in 3.20 ml of conc. HCl at 10° C. for 1 hour. The mixture was then concentrated, suspended in methylene chloride and again concentrated. Yield: 0.83 g.
ESI-MS: 174.3, [M+H$^+$]=173.2.

c.3 1-(4-Chlorobutyl)-4-phenylpyrimidin-2(1H)-one 0.84 g (4.20 mmol) of 4-phenylpyrimidin-2-ol from Example c.2 was stirred in 8.4 ml of N,N-dimethylformamide (DMF) and 0.58 g (4.20 mmol) of $K_2CO_3$ at room temperature for 1 hour. Then, 0.72 g (4.20 mmol) of 1-bromo-4-chlorobutane was added dropwise, the reaction mixture was stirred at room temperature for 12 hours, and the reaction mixture was filtered and concentrated. The residue was then taken up in toluene and concentrated, and the residue was again taken up in toluene and concentrated. The resulting residue was stirred with pentane and filtered. Yield: 0.74 g.
$^1$H NMR (400 MHz, CDCl$_3$) $\delta$ (ppm): 8.10 (2H, d), 7.71 (1H, d), 7.63-7.40 (3H, m), 6.82 (1H, d), 3.98 (2H, t), 3.58 (2H, t), 2.00 (2H, quint.), 1.90 (2H, quint.).

d. 1-(4-Chlorobutyl)-4-methyl-1H-pyrimidin-2-one d.1 4-Methylpyrimidin-2(1H)-one (in analogy to Aust. J. Chem. 1968, 21, 243-55)

20.0 ml of conc. HCl were added dropwise to 26.4 g (0.2 mol) of 4,4-dimethoxybutan-2-one in 40 ml of ethanol and 12.0 g (0.2 mol) of urea. A clear brown solution resulted after a short time, and after a further 10 minutes, a yellow precipitate separated out. The reaction mixture was heated to reflux for 1.5 hours and then allowed to cool (ice-water bath). The crystals which had separated out were then filtered off with suction and washed with ethanol, and the crystals were dried in vacuo at 40° C.; yield: 22.0 g.

d.2 1-(4-Chlorobutyl)-4-methyl-1H-pyrimidin-2-one 0.1 mol of 4-methylpyrimidin-2(1H)-one from d.1, 0.1 mol of 1-bromo-4-chlorobutane and 0.3 mol of $K_2CO_3$ were stirred in 200 ml of dimethyl sulfoxide at room temperature for 12 hours. The reaction mixture was added to ice-water, and the aqueous mixture was extracted twice with diethyl ether. The aqueous phase was extracted twice with methylene chloride. The methylene chloride phase was dried over $Na_2SO_4$, the desiccant was removed by filtration, and the solvent was evaporated to dryness in vacuo. The resulting solid residue was stirred with diethyl ether, and the precipitate was filtered off with suction, washed with diethyl ether and dried.

¹H NMR (400 MHz, CDCl₃) δ (ppm): 8.46 (1H, d), 7.46 (1H, d), 3.90 (2H, t), 3.57 (2H, t), 2.11 (3H, s.), 1.95 (2H, quint.), 1.88-1.78 (2H, quint.).

e.
1-(4-Chlorobutyl)-5-fluoro-1H-pyrimidine-2,4-dione 2.6 g (15.0 mmol) of 1-bromo-4-chlorobutane were added dropwise to a solution of 1.95 g (15.0 mmol) of 2,4-dihydroxy-5-fluoropyrimidine in 50 ml of dimethyl sulfoxide and 20.0 ml of N,N-dimethylformamide (DMF) at 0° C. 2.07 g (15.0 mmol) of K₂CO₃ were added in portions over the course of 1 hour, and the mixture was stirred at 20° C. for 1 hour (dialkylated product already identifiable). Water was then added to the reaction mixture, and the aqueous mixture was extracted twice with diethyl ether and twice with methylene chloride. The aqueous phase was adjusted to pH 3-4 with hydrochloric acid and then the aqueous phase was extracted with methylene chloride. The organic phase was then dried, the desiccant was removed by filtration, and the solvent was evaporated to dryness in vacuo; yield: 0.6 g.

Example 1

1-{4-[4-(2,4-Dichlorobenzyl)piperazin-1-yl]butyl}-5-methyl-1H-pyrimidine-2,4-dione 1-(4-Chlorobutyl)-5-methyl-1H-pyrimidine-2,4-dione (0.69 mmol, 0.15 g), 1-(2,4-dichlorobenzyl)piperazine (0.62 mmol, 0.15 g), sodium bromide (3.46 mmol, 0.36 g) and diisopropylethylamine (6.92 mmol, 0.89 g) were heated in N-methylpyrrolidinone (0.6 ml) at 120° C. for 5 hours. The reaction mixture was then allowed to cool, the suspension was filtered with suction, and the filtrate was concentrated. The residue was then then taken up in ethyl acetate and washed with saturated brine. The organic layer was dried, filtered to remove the desiccant and evaporated in vacuo. The resulting residue was purified by chromatography on silica gel (eluent: methyl tert-butyl ether/methanol (0-100%), resulting in 88.0 mg of the title compound.
ESI-MS: [M+H⁺]=425.0;
¹H NMR (400 MHz, DMSO-d₆) δ (ppm): 11.19 (1H, s br.), 7.60-7.36 (4H, m), 3.59 (2H, t), 3.52 (2H, s), 2.41 (8H, s br.), 2.33 (2H, t), 1.74 (3H, s), 1.55 (2H, quint.), 1.38 (2H, quint.).
The free base was then converted into its fumaric acid salt.

Example 2

1-{4-[4-(2,4-Dichlorobenzyl)piperazin-1-yl]butyl}-1H-pyrimidine-2,4-dione 0.17 g of the title compound was obtained in analogy to Example 1 from 1-(4-chlorobutyl)-1H-pyrimidine-2,4-dione (0.49 mmol, 0.10 g) and 1-(2,4-dichlorobenzyl)piperazine (0.44 mmol, 0.119).
ESI-MS: 413.05, 411.15;
¹H NMR (500 MHz, DMSO-d₆) δ (ppm): 11.18 (1H, s br.), 7.63 (1H, d), 7.57 (1 H, s), 7.48 (1H, m), 7.41 (1H, m), 5.52 (1H, d), 3.64 (2H, t), 3.55 (2H, s), 2.46 (8H, s br.), 2.38 (2H, t), 1.55 (2H, quint.), 1.41 (2H, quint.).
The free base was then converted into its fumaric acid salt.

Example 3

1-{4-[4-(2,4-Dichlorobenzyl)piperazin-1-yl]butyl}-4-phenyl-1H-pyrimidin-2-one 0.20 g of the title compound was obtained in analogy to Example 1 by reacting 1-(4-chlorobutyl)-4-phenyl-1H-pyrimidin-2-one (0.76 mmol, 0.20 g) with 1-(2,4-dichlorobenzyl)piperazine (0.69 mmol, 0.17 g).
ESI-MS: [M+Na⁺]=493.1, 473.15, 471.15, 236.1.
The free base was then converted into its fumaric acid salt.

Example 4

1-{4-[4-(2,4-Dichlorobenzyl)piperazin-1-yl]butyl}-4-methyl-1H-pyrimidin-2-one 21.0 mg of the title compound were obtained in analogy to Example 1 by reacting 1-(4-chlorobutyl)-4-methyl-1H-pyrimidin-2-one (0.37 mmol, 75.0 mg) with 1-(2,4-dichlorobenzyl)piperazine (0.36 mmol, 87.0 mg).
ESI-MS: 411.15, 409.15, 205.1.

Example 5

1-{4-[4-(2,4-Dichlorobenzyl)piperazin-1-yl]butyl}-5-fluoro-1H-pyrimidine-2,4-dione 22.0 mg of the title compound were obtained in analogy to Example 1 by reacting 1-(4-chlorobutyl)-5-fluoro-1H-pyrimidine-2,4-dione (0.45 mmol, 0.10 g) with 1-(2,4-dichlorobenzyl)piperazine (0.41 mmol, 0.10 mg).
ESI-MS: 431.15, 429.15, 243.1.
The free base was then converted into its fumaric acid salt.

Example 6

1-{4-[4-(2-Fluorobenzyl)piperazin-1-yl]butyl}-5-methyl-1H-pyrimidine-2,4-dione

The title compound was obtained in analogy to Example 1 by reacting 1-(4-chlorobutyl)-5-methyl-1H-pyrimidine-2,4-dione with 1-(2-fluorobenzyl)piperazine.
ESI-MS: [M+H⁺]=375.0.

Example 7

1-{4-[4-(2-Methoxybenzyl)piperazin-1-yl]butyl}-5-methyl-1H-pyrimidine-2,4-dione

The title compound was obtained in analogy to Example 1 by reacting 1-(4-chlorobutyl)-5-methyl-1H-pyrimidine-2,4-dione with 1-(2-methoxybenzyl)piperazine.
ESI-MS: [M+Na⁺]=409.0, [M+H⁺]=387.2, 264.9, 120.9.

Example 8

1-{4-[4-(2-Chlorobenzyl)piperazin-1-yl]butyl}-5-methyl-1H-pyrimidine-2,4-dione
The title compound was obtained in analogy to Example 1 by reacting 1-(4-chlorobutyl)-5-methyl-1H-pyrimidine-2,4-dione with 1-(2-chlorobenzyl)piperazine.
ESI-MS: [M+H⁺]=390.9.

Example 9

5-Methyl-1-{4-[4-(2-methylbenzyl)piperazin-1-yl]butyl}-1H-pyrimidine-2,4-dione

The title compound was obtained in analogy to Example 1 by reacting 1-(4-chlorobutyl)-5-methyl-1H-pyrimidine-2,4-dione with 1-(2-methylbenzyl)piperazine.
ESI-MS: 371.6, [M+H⁺]=371.0.

Example 10

1-{4-[4-(3,4-Dichlorobenzyl)piperazin-1-yl]butyl}-5-methyl-1H-pyrimidine-2,4-dione The title compound was obtained in analogy to Example 1 by reacting 1-(4-chlorobutyl)-5-methyl-1H-pyrimidine-2,4-dione with 1-(3,4-dichlorobenzyl)piperazine.
ESI-MS: [M+H$^+$]=425.0.

Example 11

1-{4-[4-(2-Chloro-4-fluorobenzyl)piperazin-1-yl]butyl}-5-methyl-1H-pyrimidine-2,4-dione The title compound was obtained in analogy to Example 1 by reacting 1-(4-chlorobutyl)-5-methyl-1H-pyrimidine-2,4-dione with 1-(2-chloro-4-fluorobenzyl)piperazine.
ESI-MS: [M+H$^+$]=409.0.

Example 12

1-[4-(4-Benzylpiperazin-1-yl)butyl]-5-methyl-1H-pyrimidine-2,4-dione

The title compound was obtained in analogy to Example 1 by reacting 1-(4-chlorobutyl)-5-methyl-1H-pyrimidine-2,4-dione with N-benzylpiperazine.
ESI-MS: [M+H$^+$]=357.2.

Example 13

5-Methyl-1-{4-[4-(4-methylbenzyl)piperazin-1-yl]butyl}-1H-pyrimidine-2,4-dione

The title compound was obtained in analogy to Example 1 by reacting 1-(4-chlorobutyl)-5-methyl-1H-pyrimidine-2,4-dione with 1-(4-methylbenzyl)piperazine.
ESI-MS: [M+H$^+$]=371.2.

Example 14

5-Methyl-1-{4-[4-(3-methylbenzyl)piperazin-1-yl]butyl}-1H-pyrimidine-2,4-dione

The title compound was obtained in analogy to Example 1 by reacting 1-(4-chlorobutyl)-5-methyl-1H-pyrimidine-2,4-dione with 1-(3-methylbenzyl)piperazine,
ESI-MS: 551.2, [M+H$^+$]=371.1.

Example 15

1-{4-[4-(4-Fluorobenzyl)piperazin-1-yl]butyl}-5-methyl-1H-pyrimidine-2,4-dione

The title compound was obtained in analogy to Example 1 by reacting 1-(4-chlorobutyl)-5-methyl-1H-pyrimidine-2,4-dione with 1-(4-fluorobenzyl)piperazine.
ESI-MS: [M+H$^+$]=375.1.

Example 16

1-{4-[4-(3,4-Dimethylbenzyl)piperazin-1-yl]butyl}-5-methyl-1H-pyrimidine-2,4-dione The title compound was obtained in analogy to Example 1 by reacting 1-(4-chlorobutyl)-5-methyl-1H-pyrimidine-2,4-dione with 1-(3,4-dimethylbenzyl)piperazine.
ESI-MS: [M+H$^+$]=385.3.

Example 17

1-{4-[4-(4-Methoxybenzyl)piperazin-1-yl]butyl}-5-methyl-1H-pyrimidine-2,4-dione

The title compound was obtained in analogy to Example 1 by reacting 1-(4-chlorobutyl)-5-methyl-1H-pyrimidine-2,4-dione with 1-(4-methoxybenzyl)piperazine.
ESI-MS: [M+H$^+$]=387.1, 120.9.

Example 18

5-Methyl-1-{4-[4-(2,4,6-trimethylbenzyl)piperazin-1-yl]butyl}-1H-pyrimidine-2,4-dione The title compound was obtained in analogy to Example 1 by reacting 1-(4-chlorobutyl)-5-methyl-1H-pyrimidine-2,4-dione with 1-(2,4,6-trimethylbenzyl)piperazine.
ESI-MS: [M+H$^+$]=399.3, 133.0.

Example 19

1-[4-(4-Benzo[1,3]dioxol-5-ylmethylpiperazin-1-yl)butyl]-5-methyl-1H-pyrimidine-2,4-dione The title compound was obtained in analogy to Example 1 by reacting 1-(4-chlorobutyl)-5-methyl-1H-pyrimidine-2,4-dione with 1-(benzo[1,3]dioxol-5-ylmethyl)piperazine.
ESI-MS: [M+H$^+$]=401.1, 134.9.

Example 20

5-Methyl-1-[4-(4-naphthalen-2-ylmethylpiperazin-1-yl)butyl]-1H-pyrimidine-2,4-dione The title compound was obtained in analogy to Example 1 by reacting 1-(4-chlorobutyl)-5-methyl-1H-pyrimidine-2,4-dione with 1-(naphthalen-2-ylmethyl)piperazine.
ESI-MS: [2M+H$^+$]=813.4, 587.3, [M+H$^+$]=407.1, 140.9.

Example 21

1-{4-[4-(2-Chloro-6-fluorobenzyl)piperazin-1-yl]butyl}-5-methyl-1H-pyrimidine-2,4-dione The title compound was obtained in analogy to Example 1 by reacting 1-(4-chlorobutyl)-5-methyl-1H-pyrimidine-2,4-dione with 1-(2-chloro-6-fluorobenzyl)piperazine.
ESI-MS: [M+H$^+$]=409.0.

Example 22

1-{4-[4-(4-tert-Butylbenzyl)piperazin-1-yl]butyl}-5-methyl-1H-pyrimidine-2,4-dione The title compound was obtained in analogy to Example 1 by reacting 1-(4-chlorobutyl)-5-methyl-1H-pyrimidine-2,4-dione with 1-(4-tertbutylbenzyl)piperazine.
ESI-MS: 593.2, [M+H$^+$]=413.1.

Example 23

5-Methyl-1-[4-(4-pyridin-4-ylmethylpiperazin-1-yl)butyl]-1H-pyrimidine-2,4-dione The title compound was obtained in analogy to Example 1 by reacting 1-(4-chlorobutyl)-5-methyl-1H-pyrimidine-2,4-dione with 1-(pyridin-4-ylmethyl)piperazine.
ESI-MS: [M+H$^+$]=357.7, 130.0.

Example 24

5-Methyl-1-[4-(4-pyridin-2-ylmethylpiperazin-1-yl)butyl]-1H-pyrimidine-2,4-dione The title compound was obtained in analogy to Example 1 by reacting 1-(4-chlorobutyl)-5-methyl-1H-pyrimidine-2,4-dione with 1-(pyridin-2-ylmethyl)piperazine.
ESI-MS: [2M+H$^+$]=715.3, [M+H$^+$]=358.1, 130.0.

Example 25

5-Methyl-1-[4-(4-pyridin-3-ylmethylpiperazin-1-yl)butyl]-1H-pyrimidine-2,4-dione The title compound was obtained in analogy to Example 1 by reacting 1-(4-chlorobutyl)-5-methyl-1H-pyrimidine-2,4-dione with 1-(pyridin-3-ylmethyl)piperazine.
ESI-MS: [2M+H$^+$]=715.2, [M+H$^+$]=358.0, 264.8, 130.0.

Example 26

1-[4-(4-Benzylpiperidin-1-yl)butyl]-5-methyl-1H-pyrimidine-2,4-dione

The title compound was obtained in analogy to Example 1 by reacting 1-(4-chlorobutyl)-5-methyl-1H-pyrimidine-2,4-dione with 4-benzylpiperidine.
ESI-MS: 536.5, [M+H$^+$]=356.1.

Example 27

5-Methyl-1-{4-[4-(tetrahydrofuran-2-ylmethyl)piperazin-1-yl]butyl}-1H-pyrimidine-2,4-dione The title compound was obtained in analogy to Example 1 by reacting 1-(4-chlorobutyl)-5-methyl-1H-pyrimidine-2,4-dione with 1-(tetrahydrofuran-2-ylmethyl)piperazine.
ESI-MS: [M+H$^+$]=351.1, 130.0.

Example 28

5-Methyl-1-{4-[4-(2-pyrrol-1-yl-ethyl)piperazin-1-yl]butyl}-1H-pyrimidine-2,4-dione The title compound was obtained in analogy to Example 1 by reacting 1-(4-chlorobutyl)-5-methyl-1H-pyrimidine-2,4-dione with 1-(2-pyrrol-1-ylethyl)piperazine.
ESI-MS: [M+H$^+$]=360.2.

Example 29

1-{4-[4-(Furan-2-carbonyl)piperazin-1-yl]butyl}-5-methyl-1H-pyrimidine-2,4-dione The title compound was obtained in analogy to Example 1 by reacting 1-(4-chlorobutyl)-5-methyl-1H-pyrimidine-2,4-dione with furan-2-ylpiperazin-1-ylmethanone.

Example 30

1-{4-[4-(2-Imidazol-1-ylethyl)piperazin-1-yl]butyl-5-methyl-1H-pyrimidine-2,4-dione The title compound was obtained in analogy to Example 1 by reacting 1-(4-chlorobutyl)-5-methyl-1H-pyrimidine-2,4-dione with 1-(2-imidazol-1-ylethyl)piperazine.
ESI-MS: [2M+H$^+$]=721.3, [M+H$^+$]=361.3, 293.0, 130.0.

Example 31

1-[4-(4-Cyclohexylmethylpiperazin-1-yl)butyl]-5-methyl-1H-pyrimidine-2,4-dione

The title compound was obtained in analogy to Example 1 by reacting 1-(4-chlorobutyl)-5-methyl-1H-pyrimidine-2,4-dione with 1-(cyclohexylmethyl)piperazine.
ESI-MS: [M+H$^+$]=363.3.

Example 32

5-Methyl-1-{4-[4-(tetrahydrofuran-2-carbonyl)piperazin-1-yl]butyl}-1H-pyrimidine-2,4-dione The title compound was obtained in analogy to Example 1 by reacting 1-(4-chlorobutyl)-5-methyl-1H-pyrimidine-2,4-dione with piperazin-1-yltetrahydrofuran-2-ylmethanone.
ESI-MS: [2M+H$^+$]=729.3, [M+H$^+$]=365.4, 267.0, 130.0.

Example 33

5-Methyl-1-{4-[4-(2-thiophen-2-ylethyl)piperazin-1-yl]butyl}-1H-pyrimidine-2,4-dione The title compound was obtained in analogy to Example 1 by reacting 1-(4-chlorobutyl)-5-methyl-1H-pyrimidine-2,4-dione with 1-(2-thiophen-2-ylethyl)piperazine.
ESI-MS: [M+H$^+$]=377.0.

Example 34

1-{4-[4-(2-Cyclohexylethyl)piperazin-1-yl]butyl}-5-methyl-1H-pyrimidine-2,4-dione The title compound was obtained in analogy to Example 1 by reacting 1-(4-chlorobutyl)-5-methyl-1H-pyrimidine-2,4-dione with 1-(2-cyclohexyl)piperazine.
ESI-MS: 557.5, [M+H$^+$]=377.1.

Example 35

5-Methyl-1-{4-[4-(2-oxo-2-pyrrolidin-1-ylethyl)piperazin-1-yl]butyl}-1H-pyrimidine-2,4-dione The title compound was obtained in analogy to Example 1 by reacting 1-(4-chlorobutyl)-5-methyl-1H-pyrimidine-2,4-dione with 2-piperazin-1-yl-1-pyrrolidin-1-ylethanone.
ESI-MS: [2M+H$^+$]=755.3, [M+H$^+$]=378.5, 130.0.

Example 36

5-Methyl-1-{4-[4-(2-oxo-2-piperidin-1-ylethyl)piperazin-1-yl]butyl}-1H-pyrimidine-2,4-dione The title compound was obtained in analogy to Example 1 by reacting 1-(4-chlorobutyl)-5-methyl-1H-pyrimidine-2,4-dione with 2-piperazin-1-yl-1-piperidin-1-ylethanone.
ESI-MS: [M+H$^+$]=392.2.

Examples of Pharmaceutical Administration Forms
A) Tablets
Tablets of the following composition are compressed in a tablet press in a conventional way:

---
40 mg of substance of Example 1
120 mg of corn starch
13.5 mg of gelatin
45 mg of lactose
2.25 mg of Aerosil ® (chemically pure silica in submicroscopically fine distribution)
6.75 mg of potato starch (as 6% strength paste)
---

B) Sugar-Coated Tablets
20 mg of substance of Example 1
60 mg of core composition
70 mg of sugar-coating composition The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The sugar-coated tablets produced in this way are subsequently provided with an enteric coating.

Biological Investigations—Receptor Binding Studies:

The substance to be tested was dissolved either in methanol/Chremophor® (BASFAG) or in dimethyl sulfoxide and then diluted with water to the desired concentration.

Dopamine $D_3$ Receptor:

The mixture (0.250 ml) was composed of membranes from ~106 HEK-293 cells with stably expressed human dopamine $D_3$ receptors, 0.1 nM [$^{125}$I]-iodosulpride and incubation buffer (total binding) or with additional test substance (inhibition plot) or 1 µM spiperone (nonspecific binding). Triplicate mixtures were carried out.

The incubation buffer contained 50 mM Tris, 120 mM NaCl, 5 mM KCl, 2 mM $CaCl_2$, 2 mM $MgCl_2$ and 0.1% bovine serum albumin, 10 µM quinolone, 0.1% ascorbic acid (prepared fresh each day). The buffer was adjusted to pH 7.4 with HCl.

Dopamine $D_{2L}$ Receptor

The mixture (1 ml) was composed of membranes from ~$10^6$ HEK-293 cells with stably expressed human dopamine $D_{2L}$ receptors (long isoform) and 0.01 nM [$^{125}$I]-iodospiperone and incubation buffer (total binding) or with additional test substance (inhibition plot) or 1 µM haloperidol (nonspecific binding). Triplicate mixtures were carried out.

The incubation buffer contained 50 mM Tris, 120 mM NaCl, 5 mM KCl, 2 mM $CaCl_2$, 2 mM $MgCl_2$ and 0.1% bovine serum albumin. The buffer was adjusted to pH 7.4 with HCl.

Measurement and Evaluation:

After incubation at 25° C. for 60 minutes, the mixtures were filtered under vacuum through Whatman GF/B glass fiber filters using a cell harvester. The filters were transferred by a filter transfer system into scintillation vials. After addition of 4 ml of Ultima Gold® (Packard), the samples were shaken for one hour and then the radioactivity was counted in a beta counter (Packard, Tricarb 2000 or 2200CA). The cp values were converted into dpm by means of a standard quench series with the aid of the instrument's own program.

Evaluation of the inhibition plots took place by iterative nonlinear regression analysis using the Statistical Analysis System (SAS) similar to the "LIGAND" program described by Munson and Rodbard.

In these assays, the compounds of the invention show very good affinities for the $D_3$ receptor (<100 nM, frequently <50 nM) and bind selectively to the $D_3$ receptor. The results of the binding assays are indicated in table 3.

TABLE 3

| Example | $K_i$ ($D_3$) [nM] | Selectivity $D_3$ vs. $D_2L$* |
|---|---|---|
| 1 | 8.9 | 98 |
| 2 | 4.6 | 94 |
| 3 | 3.16 | 204 |
| 4 | 17.0 | 31 |
| 5 | 10.6 | 99 |
| 10 | 18.1 | 51 |
| 11 | 22.3 | 48 |

*$K_i(D_3)/K_i(D_{2L})$

The invention claimed is:

1. A substituted N-heterocyclic compound of the formula (I.A)

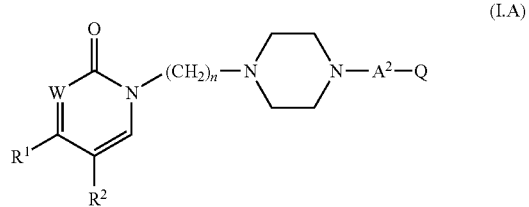

in which
W is N;
$R^1$ is OH, methyl, isopropyl, tertbutyl, $CF_3$, cyclobutyl, cyclohexyl, phenyl, p-fluorophenyl, m-fluorophenyl, o-fluorophenyl, p-methylphenyl, m-methylphenyl, o-methylphenyl or 2-furyl;
$R^2$ is H, $C_1$-$C_4$-alkyl, $CF_3$, halogen or cyano;
N is 4;
$A^2$ is a 1- to 2-membered hydrocarbon chain which may have 1 or 2 methyl groups as substituents, in which 1 carbon atom may be replaced by a carbonyl group;
Q is phenyl which optionally has 1, 2, or 3 substituents $R^Q$ which are selected independently of one another from methyl, ethyl, n-propyl, isopropyl, tert-butyl, cyclopropyl, cyclobutyl, hydroxyl, methoxy, ethoxy, trifluoromethyl, trifluoromethoxy, fluorine, chlorine, cyano, and dimethylamino;
and the tautomers of the compound I.A., the physiologically acceptable salts of the compound I.A and the physiologically acceptable salts of the tautomers of the compound I.A.

2. The compound as claimed in claim 1, in which $A^2$ is $CH_2$, $CH_2CH_2$, CO, $CH_2CO$, or $COCH_2$.

3. The compound as claimed in claim 2, in which $A^2$ is $CH_2$.

4. The compound as claimed in claim 1, in which Q is phenyl which has two substituents $R^Q$.

5. The compound as claimed in claim 4, in which the two substituents $R^Q$ are located in position 2,3 on the phenyl ring.

6. The compound as claimed in claim 4, in which the two substituents $R^Q$ are located in position 2,4 on the phenyl ring.

7. The compound as claimed in claim 4, in which the two substituents $R^Q$ are located in position 3,4 on the phenyl ring.

8. A pharmaceutical composition comprising the compound of claim 1 and/or salt thereof, together with physiologically acceptable carriers and/or excipients.

9. A method for treating schizophrenia, or parkinsonism, the method comprising administering the compound of claim 1 or a pharmacologically acceptable salt thereof or a tautomer of the at least one compound as defined in claim 1.

* * * * *